United States Patent
Bardor et al.

(10) Patent No.: US 9,587,245 B2
(45) Date of Patent: Mar. 7, 2017

(54) **N-GLYCOSYLATION IN TRANSFORMED *PHAEODACTYLUM TRICORNUTUM***

(75) Inventors: Muriel Bardor, Isneauville (FR); Romain Louvet, Evreux (FR); Bruno Saint-Jean, Nantes (FR); Carole Burel, Bourdainville (FR); Bérangère Baiet, Rouen (FR); Jean-Paul Cadoret, Basse Goulaine (FR); Patrice Lerouge, Grand Couronne (FR); Rémy Michel, Nantes (FR); Aude Carlier, Nantes (FR)

(73) Assignees: UNIVERSITE DE ROUEN, Mont-Saint-Aignan (FR); L'INSTITUT FRANCAIS DE RECHERCHE POUR L'EXPLOITATION DE LA MER (IFREMER), Issy-les-Moulineaux (FR); ALGENICS, Saint Herblain (FR)

( * ) Notice: Subject to any disclaimer, the term of this patent is extended or adjusted under 35 U.S.C. 154(b) by 196 days.

(21) Appl. No.: 13/812,605

(22) PCT Filed: Jul. 27, 2011

(86) PCT No.: PCT/EP2011/003756
§ 371 (c)(1),
(2), (4) Date: Apr. 3, 2013

(87) PCT Pub. No.: WO2012/013337
PCT Pub. Date: Feb. 2, 2012

(65) Prior Publication Data
US 2014/0154707 A1 Jun. 5, 2014

(30) Foreign Application Priority Data
Jul. 27, 2010 (FR) .................... 10 007813

(51) Int. Cl.
| C07K 14/505 | (2006.01) |
| C12N 15/82 | (2006.01) |
| C12N 9/10 | (2006.01) |
| C12P 21/00 | (2006.01) |
| C12N 9/24 | (2006.01) |

(52) U.S. Cl.
CPC ........ *C12N 15/8243* (2013.01); *C07K 14/505* (2013.01); *C12N 9/1051* (2013.01); *C12N 9/2402* (2013.01); *C12P 21/005* (2013.01); *C12Y 302/01096* (2013.01); *Y02P 20/52* (2015.11)

(58) Field of Classification Search
CPC combination set(s) only.
See application file for complete search history.

(56) References Cited

FOREIGN PATENT DOCUMENTS

| WO | 00/52135 | 9/2000 |
| WO | 2009/101160 | 8/2009 |

OTHER PUBLICATIONS

Devos et al., ("Practical Limits of Function Prediction": I., Proteins: Structure, Function and Genetics, 2000, vol. 41: 98-107.*
Fujita et al (A remodeling system for the oligosaccharide chains on glycoproteins with microbial endo-β-N-acetylglucosaminidases, Biochim Biophys Acta. Nov. 2006;1760(11):1631-5. Epub Sep. 12, 2006.*
International Search Report dated Dec. 28, 2011 in corresponding PCT application.
UniProt Consortium, Feb. 10, 2009 (Feb. 10, 2009), "The Phaeodactylum genome reveals the evolutionary history of diatom genomes" "SubName: Full=Predicted protein;", XP002613790, retrieved from EBI accession No. UNIPROT: B7GB18 Database accession No. B7GB18 the whole document.
UniProt Consortium, Feb. 10, 2009 (Feb. 10, 2009), "The Phaeodactylum genome reveals the evolutionary history of diatom genomes" "SubName: Full=Predicted protein;", XP002613791, retrieved from EBI accession No. UN I PROT: B7 FWD5 Database accession No. B7FWD5 the whole document.
UniProt Consortium,Feb. 10, 2009 (Feb. 10, 2009), "SubName: Full=Alpha-1,3-mannosyl-glycoprotein beta-1,2-N-acetylglucosaminyltransferase; Flags: Fragment;", XP002665954, retrieved from EBI accession No. UNIPROT:B7G5V7 Database accession No. B7G5V7 sequence.

* cited by examiner

*Primary Examiner* — Kagnew H Gebreyesus
(74) *Attorney, Agent, or Firm* — Young & Thompson

(57) ABSTRACT

Transformed *Phaeodactylum tricornutum* including a nucleic acid sequence operatively linked to a promoter, wherein the nucleic acid sequence encodes an N-acetylglucosaminyltransferase I and/or an α-Mannosidase II and wherein at least one β-N-acetylglucosaminidase of the transformed *Phaeodactylum tricornutum* has been inactivated. A method for producing a glycosylated polypeptide includes the steps of (i) culturing a transformed *P. tricornutum* as defined previously and (ii) purifying the polypeptide that is expressed and glycosylated in the transformed *P. Tricornutum*. The use of such a transformed *P. tricornutum* for producing a glycosylated polypeptide is also described.

8 Claims, 12 Drawing Sheets

Arabidopsis GnT1 sequence expressed in *Phaeodactylum tricornutum*

| 2x35S | GnT1 | eGFP | Terminator |
|---|---|---|---|

| 2x35S | GnT1 | Terminator |
|---|---|---|

Human GnT1 sequence expressed in *Phaeodactylum tricornutum*

| 2x35S | GnT1 | eGFP | Terminator |
|---|---|---|---|

| 2x35S | GnT1 | Terminator |
|---|---|---|

| pfcpA | GnT1 | eGFP | Terminator |
|---|---|---|---|

Endogenous GnT1 sequence expressed in *Phaeodactylum tricornutum*

| 2x35S | GnT1 | eGFP | Terminator |
|---|---|---|---|

| 2x35S | GnT1 | Terminator |
|---|---|---|

| 2x35S | PS | GnT1 | Terminator |
|---|---|---|---|

| 2x35S | PS | GnT1 | eGFP | Terminator |
|---|---|---|---|---|

| pfcpA | GnT1 | eGFP | Terminator |
|---|---|---|---|

| pfcpA | GnT1 | Terminator |
|---|---|---|

Figure 12

Mass (m/z)

SEQUENCE LISTING

<160> NUMBER OF SEQ ID NOS: 81

<210> SEQ ID NO 1
<211> LENGTH: 444
<212> TYPE: PRT
<213> ORGANISM: Phaeodactylum tricornutum

<400> SEQUENCE: 1

```
Met Arg Leu Trp Lys Arg Thr Thr Ser Gly Val Pro Pro Arg Arg
1               5                   10                  15

Arg Arg Arg Gly Gly Arg Glu Glu Arg Leu Ala Ile Gly Leu Leu Leu
                20                  25                  30

Thr Leu Ala Val Val Trp Gly Thr Val Leu Val Gly Thr Leu Val Ala
            35                  40                  45

Leu Val Ala Ser Pro Thr Lys Ser Val Pro Thr Phe Pro Thr Val Pro
    50                  55                  60

Thr Asp Ser Arg Pro Ser Ala Ala Phe Val Val Ser Asp Ala Pro Gly
65                  70                  75                  80

Ala Tyr Glu Ser Pro Leu Leu Val Phe Thr Cys Arg Arg Asp Gln Tyr
                85                  90                  95

Leu Arg Glu Thr Leu Arg Asp Ile Trp Asn Tyr Ile Pro Thr Asp Cys
            100                 105                 110

Ser Val Gly Cys Pro Leu Val Ile Ser Gln Asp Gly Asn Asp Pro Ala
        115                 120                 125

Val Arg Arg Val Val Arg Glu Phe Thr Asp Glu Phe Ala Thr Lys Asn
    130                 135                 140

Val Pro Val Ile His Trp Thr His Thr Ser Ala Leu Arg Gly Ser Thr
145                 150                 155                 160

Asn Gly Tyr Gln Ala Leu Ala Ile His Tyr Gly Trp Ala Leu Arg Arg
                165                 170                 175

Val Phe Asp Gly Gln Thr Leu Ser Gly Ser Val His Gly Ala Lys His
            180                 185                 190

Gly Thr Pro Gln Arg Val Ile Ile Leu Glu Glu Asp Leu His Val Ala
        195                 200                 205

Pro Asp Phe Phe Asp Tyr Phe Ala Ala Thr Ala Pro Leu Leu Asp His
    210                 215                 220

Asp Ser Ser Leu Leu Ala Val Ser Ala Phe His Asp Asn Gly Phe Ala
225                 230                 235                 240

His Asn Val Arg Asn Ala Ser Arg Ile Leu Arg Ser Asp Phe Phe Pro
                245                 250                 255

Gly Leu Gly Trp Met Met Asn Arg Arg Leu Trp Val Asp Glu Leu Gln
            260                 265                 270

Ser Lys Trp Pro Gly Gly Tyr Trp Asp Asp Trp Leu Arg Glu Pro Ala
        275                 280                 285
```

```
Gln Arg Gln Asp Arg Ala Ile Leu Arg Pro Glu Ile Ser Arg Thr Tyr
    290                 295                 300

His Phe Gly Thr Glu Gly Gly Thr Ser Ser Asn Gln Phe Gly Ser His
305                 310                 315                 320

Leu Ser Lys Ile Leu Leu Asn Arg Glu Thr Val Asp Trp Ser Lys Ala
            325                 330                 335

Ala Asp Leu Glu Ala Gln Leu Arg Pro Glu Val Tyr Asp Pro Ala Tyr
        340                 345                 350

Trp Ala Met Val Gln Ala Ser Thr Leu Thr Tyr Thr Ile Pro Asp Ala
    355                 360                 365

Leu Glu Gln Ala Lys Lys Ser Asn Ala Arg Leu Gln Tyr Thr Thr Ile
370                 375                 380

Glu Gln Phe Lys Tyr Leu Ala His Lys Leu Lys Leu Met Ala Asp Glu
385                 390                 395                 400

Lys Ala Asn Val Pro Arg Thr Ala Tyr Lys Gly Ile Val Glu Thr Arg
            405                 410                 415

Pro His Gly Ala Asp Tyr Phe Leu Phe Leu Thr Pro Pro Leu Ala Glu
        420                 425                 430

Leu Gln Lys Glu Phe Asp Ile Pro Ser Pro Lys Arg
    435                 440

<210> SEQ ID NO 2
<211> LENGTH: 1332
<212> TYPE: DNA
<213> ORGANISM: Phaeodactylum tricornutum

<400> SEQUENCE: 2
atgcggttgt ggaaacgtac gacgtcgggt gtgccaccac cacgccgtag acgccgtggt      60
ggacgggagg agcgtctagc gataggacta ctgctcacgc tggccgtcgt gtggggtacg     120
gtactcgtcg gtaccctcgt ggccctcgtc gcgtccccca ccaaatccgt cccgacgttt     180
cccacggtac cgaccgattc acgaccgtcc gccgccttcg tcgtctcgga cgcacccggg     240
gcgtacgaat cgcccttact cgtctttacc tgtcgacgag atcaatattt gcgcgaaaca     300
ttgcgggata tttggaacta cattccgacg gattgttcgg taggttgtcc cttggtaatt     360
tcacaagacg gcaacgaccc cgctgtccga cgtgtggtac gcgagtttac cgacgaattc     420
gccaccaaga acgtccccgt aattcactgg acgcatacga gtgccttgcg cggcagcacg     480
aacggctacc aagccttggc cattcactac ggttgggcct tgcgaagagt ctttgacgga     540
caaacgctgt ccgggagcgt tcacggtgcg aagcacggga cgccgcaacg ggtcattatc     600
ctcgaagaag atttgcacgt ggcaccggac ttttcgact actttgccgc accgcgcccc     660
cttttggacc acgattcgtc cctcctggcc gtttcggcct tcacgacaa cggctttgca     720 cacaacgttc ggaacgcatc cagaatactg cggtccgact tttccccgg tctcggatgg     780 atgatgaacc gacggttatg ggtggatgag ctccagtcca atggcccgg cggatactgg     840 gacgactggt tgcgggaacc ggcacaacgg caagatcgcg caattctaag acccgaaatc     900
tcccgcacct accactttgg caccgagggt ggcacgagta gtaaccagtt tgggtcccat     960
ttatcgaaaa tactgctcaa ccgtgaaaca gtggattgga gcaaggcagc agatctggaa    1020
gcccaactgc gacccgaagt gtacgacccg gcctactggg ccatggtgca agcctccacg    1080
ttgacgtaca ccatcccaga cgcactcgag caggccaaaa aaagtaacgc gagattacag    1140
tacaccacca ttgagcagtt caagtacctc gctcataaac tgaaactcat ggccgacgaa    1200
```

```
aaggccaatg taccacggac ggcatacaag ggaattgtgg aaacgcgccc gcacggtgcc    1260
gattactttc tattcctgac gccgcccctc gcagagctgc agaaggaatt cgacattccg    1320
tcaccgaaaa ga                                                        1332

<210> SEQ ID NO 3
<211> LENGTH: 1047
<212> TYPE: DNA
<213> ORGANISM: Phaeodactylum tricornutum

<400> SEQUENCE: 3
cgtgttgaag caaaccgccg tctgtgacga attcgatatc gattacgact gttgggagga      60
agcgacttgg gagtttctgc aggacgacgc gcaccccggg gtcctccagg ccgtgacgca     120
gttgcagaag ttctgggagc acgctacgga tgagcccgtg acgggatggc ggcccggaca     180
agccgcccaa gaggaagaag ccttgctcac ggccgaacgg gtcctcgaag tggcggcacg     240
gtactttgac gcgcacgctc aggcctttgc cgaactggtc aacagtacc aagcggacgg      300 tagggatacg accgaagccg cgacgcaaca agcactgcaa cgggactttg cgccgccat      360 gagccaacag gatgccggag aagccgcgct cgagatggaa gacgtctcca tgaagtgttt     420
cgaaaaatcc gtcgccgcgc atcagaacaa tcccgtggtg ggacgagcac tcggtatgat     480
gcagatgaaa cagcaacagg atatccaaaa cgccatggcc atggtggatt aatggacagt     540
aatactgtaa attgttaacc gccccaccgt tcctactgta aggattgtcg actcgcgttc     600
gtaccttatc ggtgtgtgta actaacataa actgtacacc tcaacccaac aagagcgact     660
tgtcggcatc gtctcgggga ctaggttttc gagaggcggt ctcgttgccc tttgacccaa     720
ccctaccact gtttagggta tcacgagatt tttcgtgccg tcgaccactg cagtgcacta     780
acgtaatgtt agctctactg tagctagcgc gaatctcggt ctcgtccttg ggcacttca      840 ccatggcgca ttggtcggtc gggtaccgag gggcacattt ggttcgttgg agtgtccaac     900
gtaaacacgt tcgtgctttc ttctgaggat acgcccgtct ggggaagcaa cattcgcatc     960
gttccaagca caacagcaca ccttaacacc acacaacaag ctccacaatc cacagcccta    1020
cggcaacgaa tcttccggac cttcgcc                                        1047

<210> SEQ ID NO 4
<211> LENGTH: 363
<212> TYPE: PRT
<213> ORGANISM: Phaeodactylum tricornutum

<400> SEQUENCE: 4

Tyr Glu Ser Pro Leu Leu Val Phe Thr Cys Arg Arg Asp Gln Tyr Leu
1               5                   10                  15

Arg Glu Thr Leu Arg Asp Ile Trp Asn Tyr Ile Pro Thr Asp Cys Ser
            20                  25                  30

Val Gly Cys Pro Leu Val Ile Ser Gln Asp Gly Asn Asp Pro Ala Val
        35                  40                  45

Gln Arg Val Val Arg Glu Phe Thr Asp Glu Phe Ala Thr Lys Asn Val
    50                  55                  60

Pro Val Val His Trp Thr His Thr Ser Ala Leu Arg Gly Gly Thr Asn
65                  70                  75                  80

Gly Tyr Gln Ala Leu Ala Ile His Tyr Gly Trp Ala Leu Arg Arg Val
                85                  90                  95

Phe Asp Gly Gln Thr Leu Ser Gly Ser Val His Gly Ala Lys His Gly
            100                 105                 110
```

Thr Pro Lys Arg Val Ile Ile Leu Glu Glu Asp Leu His Val Ala Pro
            115                 120                 125

Asp Phe Phe Asp Tyr Phe Ala Ala Thr Ala Pro Leu Leu Asp His Asp
    130                 135                 140

Ser Ser Leu Leu Ala Val Ser Ala Phe His Asp Asn Gly Phe Ala His
145                 150                 155                 160

Asn Val Arg Asn Ala Ser Arg Ile Leu Arg Ser Asp Phe Phe Pro Gly
                165                 170                 175

Leu Gly Trp Met Met Asn Arg Arg Leu Trp Val Asp Glu Leu Gln Ser
            180                 185                 190

Lys Trp Pro Gly Gly Tyr Trp Asp Asp Trp Leu Arg Glu Pro Ala Gln
        195                 200                 205

Arg Gln Asp Arg Ala Ile Leu Arg Pro Glu Ile Ser Arg Thr Tyr His
    210                 215                 220

Phe Gly Thr Glu Gly Gly Thr Ser Ser Asn Gln Phe Gly Ser His Leu
225                 230                 235                 240

Ser Lys Ile Leu Leu Asn Arg Glu Thr Val Asp Trp Ser Lys Ala Val
                245                 250                 255

Asp Leu Glu Ala Gln Leu Arg Pro Glu Val Tyr Asp Pro Ala Tyr Trp
            260                 265                 270

Ala Met Val Gln Ala Ser Thr Leu Thr Tyr Thr Ile Pro Asp Ala Leu
        275                 280                 285

Glu Gln Ala Lys Lys Ser Asn Ala Arg Leu Gln Tyr Thr Thr Ile Glu
    290                 295                 300

Gln Phe Lys Tyr Leu Ala His Lys Leu Lys Leu Met Ala Asp Glu Lys
305                 310                 315                 320

Ala Asn Val Pro Arg Thr Ala Tyr Lys Gly Ile Val Glu Thr Arg Pro
                325                 330                 335

His Gly Ala Asp Asn Phe Leu Phe Leu Thr Pro Pro Leu Ala Glu Leu
            340                 345                 350

Gln Lys Glu Phe Asp Ile Pro Ser Pro Lys Arg
        355                 360

<210> SEQ ID NO 5
<211> LENGTH: 1256
<212> TYPE: PRT
<213> ORGANISM: Phaeodactylum tricornutum

<400> SEQUENCE: 5

Met Arg Gln Leu Val Arg Thr Leu Ser Phe Asp Asn Pro Asp Gly Gly
1               5                   10                  15

Val Trp Lys Gln Gly Trp Asn Val Thr Ala Arg Asp Asp Phe Thr Asn
            20                  25                  30

Ala Gln Pro Leu Gln Val Phe Val Pro His Ser His Cys Asp Pro
        35                  40                  45

Gly Trp Ile Lys Thr Phe Asp Asp Tyr Phe Gln Ser Gln Thr Arg Gln
    50                  55                  60

Ile Leu Thr Thr Val Val Gln Ala Leu Gln Arg Asp Gln Arg Arg Lys
65                  70                  75                  80

Phe Ile Trp Ala Glu Ile Ser Tyr Phe Glu Trp Trp Tyr Arg Glu Gln
                85                  90                  95

Lys Asp Asp Thr Arg Lys Val Val Gln Thr Leu Leu Asp Asn Lys Gln
            100                 105                 110

Leu Gln Phe Val Thr Gly Gly Trp Val Gln Pro Asp Glu Ala Asn Ser
        115                 120                 125

```
Glu Leu Tyr Ala Met Glu Ile Gln Leu Gln Glu Gly His Asp Trp Ile
    130                 135                 140

Arg Gln Thr Phe Gly Asp Ala His Val Pro Lys His Gly Trp Ser Ile
145                 150                 155                 160

Asp Pro Phe Gly Tyr Ser Pro Thr Met Ala Tyr Leu Leu Gln Lys Tyr
                165                 170                 175

Gly Phe Lys Ala Met Leu Ile Gln Arg Val His Tyr Ala Val Lys Lys
                180                 185                 190

Glu Leu Ala Gln Arg Arg His Leu Glu Phe Tyr Trp Arg Gln Thr Trp
            195                 200                 205

Glu Asp Ala Thr Thr Ala Gly Thr His Asp Ile Phe Thr His Val Met
210                 215                 220

Pro Phe Phe Ser Tyr Asp Val Pro His Thr Cys Gly Pro Asp Pro Ser
225                 230                 235                 240

Val Cys Cys Gln Phe Asp Phe Gln Arg Thr Thr Cys Pro Trp Leu Lys
                245                 250                 255

Ala Pro Gln Thr Ile Thr Ser Lys Asn Val Ala Glu Arg Ala Met Leu
                260                 265                 270

Leu Leu Asp Gln Tyr Arg Lys Lys Ala Ala Leu Tyr Arg Ser Asn Val
            275                 280                 285

Val Leu Ala Pro Leu Gly Asp Asp Phe Arg Tyr Leu Thr Ala Gln Glu
290                 295                 300

Ala Glu Ala Gln Tyr Thr Asn Tyr Gln Ala Ile Phe Asp Tyr Val Asn
305                 310                 315                 320

Ala Asn Leu Pro Asn Val Lys Met Gln Phe Gly Thr Leu Ser Asp Tyr
                325                 330                 335

Phe Asp Ala Val Val Gly Ser Phe Asp Thr Pro Ile Leu Gln Gly Ser
            340                 345                 350

Phe Phe Thr Tyr Ser Asp Ile Asp Gln Asp Tyr Trp Ser Gly Tyr Phe
            355                 360                 365

Thr Ser Arg Val Ser Asp Lys Ala Leu Gly Arg Trp Leu Glu Arg Val
370                 375                 380

Leu Tyr Ser Ala Thr Gln Met Gly Ala Ser Lys Gln Asp Leu Gln Ala
385                 390                 395                 400

Pro Arg Arg Ala Leu Ser Leu Phe Gln His His Asp Gly Val Thr Gly
                405                 410                 415

Thr Ala Lys Thr His Val His Glu Asp Tyr Ala Arg Gln Met Met Asp
                420                 425                 430

Ala Ile His Thr Thr Glu Asp Trp Met Leu Arg Ala Ile His Gln Gln
            435                 440                 445

Tyr Gly Thr Glu Leu Gln Pro Leu Leu Thr Ala Asp Thr Thr Ala Gly
450                 455                 460

Ala Ile Gln Pro Cys Trp Val Ala Pro Glu Pro Arg Thr Met Pro Glu
465                 470                 475                 480

Asn Ala Cys Glu Ser Glu Tyr Thr Val Asp Ser Ala Ala Ser Ser Pro
                485                 490                 495

Pro Ala Leu Val Ala Val Tyr Asn Pro Leu Ser Thr Ser Gln His Cys
                500                 505                 510

Gly Asn Val Val Val Pro Gly Gln Lys Leu Arg Thr Ala Thr Leu Pro
            515                 520                 525

Cys Glu Leu Pro Gly Pro Thr Ser Val Ser Gln Thr Lys Phe Val Phe
530                 535                 540
```

-continued

```
His Pro Glu Thr Gly Leu Met Leu Glu Pro Val Lys Glu Glu Trp Lys
545                 550                 555                 560

Val Trp Lys Val Lys Lys Gly Gly Ala Tyr Leu Phe Phe Pro Gly Gln
                565                 570                 575

Leu Arg Ser Tyr Glu Leu Thr Lys His Asp Val Ile Ile Glu Asp Gly
            580                 585                 590

Gly Tyr Val Val Ser Thr Glu Ser Trp Lys Arg Thr Val Val Glu Arg
        595                 600                 605

Glu Ile Pro Thr Asp Phe Gly Ile Ser Ser Thr Val Ile Asp Phe Val
    610                 615                 620

Tyr Glu Thr Thr Leu Ile Glu Gly Asn Arg Glu Trp Phe Val Arg Phe
625                 630                 635                 640

Ser Gly Asn Val Ala Asn Asn Gly Ile Phe His Thr Asp Leu Asn Gly
                645                 650                 655

Phe Asn Phe Asp Thr His Tyr Phe Arg Ala Asp Met Pro Ile Gln Ser
            660                 665                 670

Gln Val Phe Pro Met Pro Thr Met Ser Ala Ile Gln Asp Asp Gln Thr
        675                 680                 685

Arg Leu Thr Val Leu Ser Glu His Ala Gln Gly Ala Ala Ser Leu Gln
    690                 695                 700

Asp Gly Ala Ile Asp Val Trp Leu Asp Arg Arg Leu Asp Gln Asp Asp
705                 710                 715                 720

Asp Arg Gly Leu Gly Gln Gly Ile Ser Asp Asn Arg Pro Thr Arg Thr
                725                 730                 735

Arg Leu Arg Val Val Glu Arg Glu Thr Phe Asn Val Gln Lys Glu
            740                 745                 750

Phe Asp Val Thr Pro Leu Val Arg Arg Thr Trp Asp Glu Leu Gln His
        755                 760                 765

Pro Leu Val Leu Phe Gly Lys His Val Lys Lys Ser Ile Asp Leu Val
    770                 775                 780

Ala Asp Pro Trp Lys His Arg Ser Asp Ser Glu Ala Arg Gln Ala Arg
785                 790                 795                 800

Arg Glu Arg Gln Arg Gln Gln Arg Ala Arg Glu Arg Gln Arg Gln Leu
                805                 810                 815

Gln Glu Lys Glu Glu Lys Arg Gly Ala Gly Asp Gln Gln Leu Phe Val
            820                 825                 830

Asn Asp Lys Pro Lys Glu Ser Ala Leu Lys Gly Phe Trp Asn Thr Gly
        835                 840                 845

Ile Ile Thr Ser Asp Phe Phe Gly Phe Phe Arg Lys Ala Ser Glu Thr
    850                 855                 860

Leu Pro Lys Asp Gln Gly His Glu Asp Gly Lys Gln Leu Gln Lys Met
865                 870                 875                 880

Pro Gly Lys Thr Arg Val Ser Lys Gly Asn Arg Arg His Arg His Pro
                885                 890                 895

Pro Val Asp Ser Phe Gln Arg Lys Phe Leu Val Asn Asp Ala Asp Trp
            900                 905                 910

Met Asn Gly Gly Arg Ser Tyr Ala Ser Arg Lys Thr Arg Glu Ile Lys
        915                 920                 925

Asn Arg Arg Phe Thr Met Lys Asn Thr Asp Ile Pro Phe Val Leu Met
    930                 935                 940

Val Tyr Lys Arg Val Asp Tyr Leu Lys Lys Ala Ile Asp Ser Val Arg
945                 950                 955                 960

Arg Ser Asp Phe Pro Lys Ser Arg Val Pro Leu Ile Ile Ser His Asp
```

|  |  |  | 965 |  |  | 970 |  |  | 975 |  |  |
|---|---|---|---|---|---|---|---|---|---|---|---|
| Gly | Arg | Val | Pro | Glu | Val | Val | Glu | Tyr | Val | Glu | Ser | Leu | Lys | Asp | Glu |
|  |  |  | 980 |  |  | 985 |  |  | 990 |  |  |

Gly Arg Val Pro Glu Val Val Glu Tyr Val Glu Ser Leu Lys Asp Glu
            980               985               990

Phe Lys Ile Ile Gln Leu Ile His  Pro His Ser Cys Tyr  Glu His Pro
        995              1000              1005

Asn Glu  Phe Pro Gly Asp Asp  Pro Thr Leu Asn Glu  Gly Phe Ala
   1010              1015              1020

Gly Asp  Ser Tyr Gly Asn Pro  Arg Ser Ala Trp Ile  Thr Cys Cys
   1025              1030              1035

Lys His  His Phe Thr Trp Met  Leu His Thr Val Phe  Arg Arg Asp
   1040              1045              1050

Phe Thr  Asp Pro Ala Val Asp  Thr Phe Leu Phe Leu  Glu Glu Asp
   1055              1060              1065

Tyr Ile  Val Ala Pro Thr Ile  Tyr Ser Ala Val Ile  Ala Gly Leu
   1070              1075              1080

Asn Val  Met Glu Asp Met Asp  Lys Glu Ile Pro Gly  Gly Phe Phe
   1085              1090              1095

Gly Leu  Gly Met Asp Pro Ser  Met Ala Asn Thr Ala  Phe Glu Pro
   1100              1105              1110

Tyr Tyr  Lys Lys Ala Thr Trp  Tyr Val Glu Ala Phe  Lys Ser Gly
   1115              1120              1125

Pro Met  Thr Met Asn Arg Asp  Met Phe Lys Lys Leu  Gln Gln His
   1130              1135              1140

Ala Lys  Glu Tyr Cys Thr Phe  Asp Asp Tyr Asn Trp  Asp Trp Ser
   1145              1150              1155

Ile Val  His Leu Gln Ser Lys  Lys Leu Leu Pro Arg  Thr Leu Leu
   1160              1165              1170

Met Pro  Ser Lys Val Leu Ala  Lys His Ile Gly Val  Lys Glu Gly
   1175              1180              1185

Met His  Thr Asn Lys Ser Phe  Gly Lys Asp Phe Ser  Asp Leu Phe
   1190              1195              1200

Pro Asn  Tyr Ala Pro Arg Arg  Glu Gln Leu Thr Thr  His Phe Ala
   1205              1210              1215

Glu Tyr  Arg Phe Thr Gly Asn  Thr Ala Ala Ala Leu  His Thr Glu
   1220              1225              1230

Phe Asn  Pro Gly Tyr Gly Gly  Trp Gly His Pro Lys  Asp His Glu
   1235              1240              1245

His Cys  Met Lys Val Leu Gln  Ser
   1250              1255

<210> SEQ ID NO 6
<211> LENGTH: 3771
<212> TYPE: DNA
<213> ORGANISM: Phaeodactylum tricornutum

<400> SEQUENCE: 6

```
atgcgccaat tggttcggac cttgagcttt gacaatcccg atggaggcgt ctggaaacag    60
ggatggaacg tcacggcacg ggacgacttt accaacgctc agccgctaca ggtattcgtc   120
gtcccgcact cccactgtga tccgggatgg atcaagacct tgacgattta cttccaatcg   180
cagactcgcc aaatccttac caccgtcgtc caggctctcc aacgagacca acgccgcaaa   240
ttcatctggg ccgaaatttc ctactttgaa tggtggtacc gcgaacaaaa ggacgacact   300
cgaaaagtgg tccaaacgct ccttgataat aagcagctgc aattcgtcac gggcggatgg   360
```

-continued

```
gtacaaccgg acgaggccaa ttcggaatta tacgctatgg aaattcaact gcaggaaggg      420
catgattgga ttcgacaaac gttcggggac gcccatgtcc ccaaacacgg atggtccatt      480
gatccctttg gctattcccc cactatggcc taccttttgc aaaaatacgg attcaaggcc      540
atgctcattc aacgggtaca ctacgccgtc aagaaggaac tcgcgcaacg ccgtcacttg      600
gaattttatt ggcggcaaac ctgggaggac gccaccacgg cgggcactca cgatattttc      660
acccacgtca tgccgttctt ttcctacgac gtaccgcata cgtgcggacc agatccctcg      720
gtctgctgtc aatttgactt ccaacgcact acgtgtccgt ggctcaaggc gccgcaaacc      780
atcacctcca aaaacgtggc cgaacgagca atgctcttgt tggatcagta tcgaaaaaag      840
gcggctctct accggtccaa cgtagtcctg gcaccactgg gagatgactt tcgctacctg      900
acggctcagg aagccgaggc ccagtacacc aattaccaag caatctttga ttacgtcaac      960
gccaacctgc cgaatgttaa aatgcaattt ggaactttgt cggactattt tgatgccgtg      1020
gtgggttcgt ttgacacacc catactacaa ggatccttct ttacctactc cgacattgat      1080
caagactact ggtcggggta ttttacttcc cgtgtttccg acaaggcctt gggtcgttgg      1140
ttggaacgcg tcttgtactc tgcaacgcag atgggtgcat cgaaacaaga cctccaggct      1200
ccccgacggg ccctgtccct ctttcagcat catgacggcg tcactgggac cgccaaaact      1260
catgtacacg aagattacgc ccgccaaatg atggacgcca ttcataccac cgaggactgg      1320
atgctgcgtg cgattcatca acagtacggg actgaactgc aaccctgtt gaccgcggat       1380 actacggccg cgcaatcca accgtgctgg gtcgcgcccg aaccacggac catgcccgaa       1440
aatgcgtgtg aatcggagta cactgtagat tccgcagcgt cgtcgccgcc agcccttgta      1500
gcggtctaca acccgctgtc gacatcgcaa cactgtggta acgtggttgt gcccggccaa      1560
aagctacgaa ctgccacact accctgtgaa ctccctggtc ccacgtcagt gtcacaaaca      1620
aagtttgtct ccatcccga cgggggctt atgctagaac ccgtcaagga ggagtggaag       1680
gtatggaaag tcaagaaggg aggagcatac ttgttcttcc ctggacaatt aaggtcttat      1740
gagctaacaa aacacgatgt gattatagag acggtggat acgttgtgtc gactgagtcc       1800
tggaagcgca ctgtggtgga acgcgagata ccgacagatt ttggtatcag ctcgacggtg      1860
atcgatttcg tttacgaaac taccttgatt gagggtaatc gcgaatggtt tgtgcgtttt      1920
tccggtaatg tcgcgaacaa cggcattttc cacacggact tgaacggctt caacttcgat      1980
acccattatt tccgagcgga tatgcccatt caatcgcaag ttttttcccat gccgaccatg    2040 tcggccatac aagacgacca aacacgcttg actgttttga gtgaacacgc gcaaggtgcc     2100
gctagcttgc aggatggcgc cattgatgtt tggttggatc gtcgattaga tcaggacgat     2160
gaccgaggtc taggccaggg tatatcggac aatagaccaa cccggacgcg acttcgagtt     2220
gtggtggaac gagaaacgtt caatgtgcag aaggagtttg acgtcacgcc actagtacgc     2280
aggacctggg atgagcttca acatcctctt gtactttttg gaaagcatgt taaaaagtcg     2340
atcgaccttg ttgccgatcc gtggaagcac cgatccgatt cagaagcccg acaagcacga     2400
agagaaaggc aacgtcaaca acgcgcgcga gagcggcaac ggcagctgca agaaaaagaa     2460
gaaaagaggg gcgctggtga ccagcaacta ttcgtgaatg ataaaccaaa agagtcagct     2520
ttgaagggtt tttggaatac tggaatcatt acgtctgact tttttggctt tttccgcaaa     2580
gcaagtgaaa ctcttcctaa agatcaaggt catgaagacg gcaaacaact gcaaaaaatg     2640
ccaggtaaaa cgagagtttc caaaggaaat cgacgccatc gacatccacc ggtcgattct    2700
tttcagcgca agttcttggt caacgacgct gactggatga atggggggag atcgtacgca    2760
```

```
tcgcgcaaaa cccgtgaaat caagaatcgt cgctttacaa tgaagaacac ggacatcccg    2820
ttcgtattga tggtttataa gcgcgtggat tatttgaaaa aggcgattga ttcggtccgt    2880
cgatccgact ttccaaagtc tcgtgtgcct cttatcattt cgcacgatgg acgagtgccg    2940
gaagtcgttg agtatgtcga atcgctgaaa gacgagttca aaattatcca actcattcat    3000
ccgcattctt gctacgagca tcccaacgag tttcctgggg atgatcccac actcaacgaa    3060
ggctttgctg gagatagcta tggtaatcca cggagtgcgt ggatcacctg ctgcaaacat    3120
cattttactt ggatgcttca cactgtcttt cgtcgggact ttacggaccc agcagtggat    3180
acatttttgt ttctcgaaga agattacatc gtggctccta cgatttattc cgccgttatt    3240
gctgggttga atgttatgga agacatggac aaggagattc cgggcggctt cttcggtttg    3300
ggtatggatc cgagtatggc gaatactgcc tttgagcctt actacaagaa ggcgacgtgg    3360
tatgtcgaag cattcaagtc aggtccgatg acgatgaacc gggacatgtt caaaaagctc    3420
caacaacatg ctaaggagta ctgtacgttc gacgattaca attgggattg gtccattgtc    3480
catctacaaa gtaaaaagtt actaccacgg actcttctca tgccaagcaa agtcctagca    3540
aaacatattg gtgtcaagga gggtatgcac acgaacaaat cctttggaaa agacttttca    3600
gatttatttc ccaactatgc ccctcgtcgc gagcagctga ccacgcattt tgcggaatac    3660
cgttttaccg ggaacaccgc ggcagcttta cacaccgaat tcaatcccgg ttatggtggt    3720
tggggacatc cgaaagacca cgagcactgc atgaaagtgc tacagtcgta a             3771

<210> SEQ ID NO 7
<211> LENGTH: 1000
<212> TYPE: DNA
<213> ORGANISM: Phaeodactylum tricornutum

<400> SEQUENCE: 7
tacaattatc gagcgcactc tcgagagcgc agtagacgga ggggtgaccg tcactaccgg      60
aaattgtttt gggccccccgt tggtacgacc aagactcaag agaagaacag aaaacacagt    120
acgcagcata cgcgacactt tgtcgatgaa ctgcaactac aggctaccct cgcaagttat    180
ctctaaaggc agcaatcctg tgacacttgc tcggttgttc ccgtctctca atccaatccg    240
cacggaagga tcgatatcgg attggatttc ggcagataag acgaccgtac agtgagtgac    300
gggtcgacac tgtccagcct tgttgttgtt ttccatccca ctcgttctct agcagattca    360
ctcttggatc tacgcaagca acggcttata acctaaatta ctactccaaa tgattcgcag    420
tcgcaccggt gccaacggca ctaacggcgc ggtaccagcc cgtacgagtc cgacccaatc    480
ctcctccgcg ttgctcgaat ctccctccac cacaacgtcg tcagtgacgt ccaccactaa    540
cctaaacagt aaccacaact ccgtttccgt cagccgattc tcccgttggc ttttggcacc    600
atcccgggcg tccccgtcgc cgccaacact ctcacctccg gcgcgcgtgg cacgcaaatc    660
acgtctccga cggcgacccc tggcctcggc ttccgccgcc aaggcgtcca ccttgcgtca    720
ccatctcgga tgggttgctc ccctcgctct cgtattactc gcactcttta cgctcgtgct    780
ttttgtgagt atttatttac tcgaaaccac tgccaatgcc ggcgtctcta cggcggaggg    840
ctccaatgtg gtatcccccc gtcgtgcctt ttggcaacaa cacttgcgac ggcctgcacc    900
ttccgacaca gccgtggtac caactgatca cgccatgcat cgaccttccg gtgctaccat    960
cggaacaaaa atcagtacca aacccgaaga ctggattgat                         1000

<210> SEQ ID NO 8
```

<211> LENGTH: 1220
<212> TYPE: PRT
<213> ORGANISM: Phaeodactylum tricornutum

<400> SEQUENCE: 8

```
Gln Val Phe Val Val Pro His Ser His Cys Asp Pro Gly Trp Ile Lys
1               5                   10                  15

Thr Phe Asp Asp Tyr Phe Gln Ser Gln Thr Arg Gln Ile Leu Thr Thr
            20                  25                  30

Val Val Gln Ala Leu Gln Arg Asp Gln Arg Lys Phe Ile Trp Ala
        35                  40                  45

Glu Ile Ser Tyr Phe Glu Trp Trp Tyr Arg Glu Gln Lys Asp Asp Thr
    50                  55                  60

Arg Lys Val Val Gln Thr Leu Leu Asp Asn Lys Gln Leu Gln Phe Val
65                  70                  75                  80

Thr Gly Gly Trp Val Gln Pro Asp Glu Ala Asn Ser Glu Leu Tyr Ala
            85                  90                  95

Met Glu Ile Gln Leu Gln Glu Gly His Asp Trp Ile Arg Gln Thr Phe
        100                 105                 110

Gly Asp Ala His Val Pro Lys His Gly Trp Ser Ile Asp Pro Phe Gly
    115                 120                 125

Tyr Ser Pro Thr Met Ala Tyr Leu Leu Gln Lys Tyr Gly Phe Lys Ala
130                 135                 140

Met Leu Ile Gln Arg Val His Tyr Ala Val Lys Lys Glu Leu Ala Gln
145                 150                 155                 160

Arg Arg His Leu Glu Phe Tyr Trp Arg Gln Thr Trp Glu Asp Ala Thr
                165                 170                 175

Thr Ala Gly Thr His Asp Ile Phe Thr His Val Met Pro Phe Phe Ser
            180                 185                 190

Tyr Asp Val Pro His Thr Cys Gly Pro Asp Pro Ser Val Cys Cys Gln
        195                 200                 205

Phe Asp Phe Gln Arg Thr Cys Pro Trp Leu Lys Ala Pro Gln Thr
    210                 215                 220

Ile Thr Ser Lys Asn Val Ala Glu Arg Ala Met Leu Leu Leu Asp Gln
225                 230                 235                 240

Tyr Arg Lys Lys Ala Ala Leu Tyr Arg Ser Asn Val Val Leu Ala Pro
                245                 250                 255

Leu Gly Asp Asp Phe Arg Tyr Leu Thr Ala Gln Glu Ala Glu Ala Gln
            260                 265                 270

Tyr Thr Asn Tyr Gln Ala Ile Phe Asp Tyr Val Asn Ala Asn Leu Pro
        275                 280                 285

Asn Val Lys Met Gln Phe Gly Thr Leu Ser Asp Tyr Phe Asp Ala Val
    290                 295                 300

Val Gly Ser Phe Asp Thr Pro Ile Leu Gln Gly Ser Phe Thr Tyr
305                 310                 315                 320

Ser Asp Ile Asp Gln Asp Tyr Trp Ser Gly Tyr Phe Thr Ser Arg Val
                325                 330                 335

Ser Asp Lys Ala Leu Gly Arg Trp Leu Glu Arg Val Leu Tyr Ser Ala
            340                 345                 350

Thr Gln Met Gly Ala Ser Lys Gln Asp Leu Gln Ala Pro Arg Arg Ala
        355                 360                 365

Leu Ser Leu Phe Gln His His Asp Gly Val Thr Gly Thr Ala Lys Thr
    370                 375                 380

His Val His Glu Asp Tyr Ala Arg Gln Met Met Asp Ala Ile His Thr
```

```
              385                 390                 395                 400

Thr Glu Asp Trp Met Leu Arg Ala Ile His Gln Gln Tyr Gly Thr Glu
                        405                 410                 415

Leu Gln Pro Leu Leu Thr Ala Asp Thr Thr Ala Gly Ala Ile Gln Pro
                        420                 425                 430

Cys Trp Val Ala Pro Glu Pro Arg Thr Met Pro Glu Asn Ala Cys Glu
                        435                 440                 445

Ser Glu Tyr Thr Val Asp Ser Ala Ala Ser Ser Pro Pro Ala Leu Val
                450                 455                 460

Ala Val Tyr Asn Pro Leu Ser Thr Ser Gln His Cys Gly Asn Val Val
        465                 470                 475                 480

Val Pro Gly Gln Lys Leu Arg Thr Ala Thr Leu Pro Cys Glu Leu Pro
                        485                 490                 495

Gly Pro Thr Ser Val Ser Gln Thr Lys Phe Val Phe His Pro Glu Thr
                        500                 505                 510

Gly Leu Met Leu Glu Pro Val Lys Glu Glu Trp Lys Val Trp Lys Val
                        515                 520                 525

Lys Lys Gly Gly Ala Tyr Leu Phe Phe Pro Gly Gln Leu Arg Ser Tyr
                530                 535                 540

Glu Leu Thr Lys His Asp Val Ile Ile Glu Asp Gly Tyr Val Val
        545                 550                 555                 560

Ser Thr Glu Ser Trp Lys Arg Thr Val Val Glu Arg Glu Ile Pro Thr
                        565                 570                 575

Asp Phe Gly Ile Ser Ser Thr Val Ile Asp Phe Val Tyr Glu Thr Thr
                        580                 585                 590

Leu Ile Glu Gly Asn Arg Glu Trp Phe Val Arg Phe Ser Gly Asn Val
                        595                 600                 605

Ala Asn Asn Gly Ile Phe His Thr Asp Leu Asn Gly Phe Asn Phe Asp
                        610                 615                 620

Thr His Tyr Phe Arg Ala Asp Met Pro Ile Gln Ser Gln Val Phe Pro
        625                 630                 635                 640

Met Pro Thr Met Ser Ala Ile Gln Asp Asp Gln Thr Arg Leu Thr Val
                        645                 650                 655

Leu Ser Glu His Ala Gln Gly Ala Ala Ser Leu Gln Asp Gly Ala Ile
                        660                 665                 670

Asp Val Trp Leu Asp Arg Arg Leu Asp Gln Asp Asp Arg Gly Leu
                        675                 680                 685

Gly Gln Gly Ile Ser Asp Asn Arg Pro Thr Arg Thr Arg Leu Arg Val
                        690                 695                 700

Val Val Glu Arg Glu Thr Phe Asn Val Gln Lys Glu Phe Asp Val Thr
        705                 710                 715                 720

Pro Leu Val Arg Arg Thr Trp Asp Glu Leu Gln His Pro Leu Val Leu
                        725                 730                 735

Phe Gly Lys His Val Lys Lys Ser Ile Asp Leu Val Ala Asp Pro Trp
                        740                 745                 750

Lys His Arg Ser Asp Ser Glu Ala Arg Gln Ala Arg Glu Arg Gln
                        755                 760                 765

Arg Gln Gln Arg Ala Arg Glu Arg Gln Arg Gln Leu Gln Glu Lys Glu
                        770                 775                 780

Glu Lys Arg Gly Ala Gly Asp Gln Gln Leu Phe Val Asn Asp Lys Pro
        785                 790                 795                 800

Lys Glu Ser Ala Leu Lys Gly Phe Trp Asn Thr Gly Ile Ile Thr Ser
                        805                 810                 815
```

```
Asp Phe Phe Gly Phe Phe Arg Lys Ala Ser Glu Thr Leu Pro Lys Asp
            820                 825                 830

Gln Gly His Glu Asp Gly Lys Gln Leu Gln Lys Met Pro Gly Lys Thr
            835                 840                 845

Arg Val Ser Lys Gly Asn Arg Arg His Arg His Pro Pro Val Asp Ser
            850                 855                 860

Phe Gln Arg Lys Phe Leu Val Asn Asp Ala Asp Trp Met Asn Gly Gly
865                 870                 875                 880

Arg Ser Tyr Ala Ser Arg Lys Thr Arg Glu Ile Lys Asn Arg Arg Phe
                885                 890                 895

Thr Met Lys Asn Thr Asp Ile Pro Phe Val Leu Met Val Tyr Lys Arg
                900                 905                 910

Val Asp Tyr Leu Lys Lys Ala Ile Asp Ser Val Arg Arg Ser Asp Phe
                915                 920                 925

Pro Lys Ser Arg Val Pro Leu Ile Ile Ser His Asp Gly Arg Val Pro
                930                 935                 940

Glu Val Val Glu Tyr Val Glu Ser Leu Lys Asp Glu Phe Lys Ile Ile
945                 950                 955                 960

Gln Leu Ile His Pro His Ser Cys Tyr Glu His Pro Asn Glu Phe Pro
                965                 970                 975

Gly Asp Asp Pro Thr Leu Asn Glu Gly Phe Ala Gly Asp Ser Tyr Gly
                980                 985                 990

Asn Pro Arg Ser Ala Trp Ile Thr Cys Cys Lys His His Phe Thr Trp
            995                 1000                1005

Met Leu His Thr Val Phe Arg Arg Asp Phe Thr Asp Pro Ala Val
            1010                1015                1020

Asp Thr Phe Leu Phe Leu Glu Glu Asp Tyr Ile Val Ala Pro Thr
            1025                1030                1035

Ile Tyr Ser Ala Val Ile Ala Gly Leu Asn Val Met Glu Asp Met
            1040                1045                1050

Asp Lys Glu Ile Pro Gly Gly Phe Phe Gly Leu Gly Met Asp Pro
            1055                1060                1065

Ser Met Ala Asn Thr Ala Phe Glu Pro Tyr Tyr Lys Lys Ala Thr
            1070                1075                1080

Trp Tyr Val Glu Ala Phe Lys Ser Gly Pro Met Thr Met Asn Arg
            1085                1090                1095

Asp Met Phe Lys Lys Leu Gln Gln His Ala Lys Glu Tyr Cys Thr
            1100                1105                1110

Phe Asp Asp Tyr Asn Trp Asp Trp Ser Ile Val His Leu Gln Ser
            1115                1120                1125

Lys Lys Leu Leu Pro Arg Thr Leu Leu Met Pro Ser Lys Val Leu
            1130                1135                1140

Ala Lys His Ile Gly Val Lys Glu Gly Met His Thr Asn Lys Ser
            1145                1150                1155

Phe Gly Lys Asp Phe Ser Asp Leu Phe Pro Asn Tyr Ala Pro Arg
            1160                1165                1170

Arg Glu Gln Leu Thr Thr His Phe Ala Glu Tyr Arg Phe Thr Gly
            1175                1180                1185

Asn Thr Ala Ala Ala Leu His Thr Glu Phe Asn Pro Gly Tyr Gly
            1190                1195                1200

Gly Trp Gly His Pro Lys Asp His Glu His Cys Met Lys Val Leu
            1205                1210                1215
```

Gln Ser
1220

<210> SEQ ID NO 9
<211> LENGTH: 1085
<212> TYPE: PRT
<213> ORGANISM: Phaeodactylum tricornutum

<400> SEQUENCE: 9

Met Gln Ser Ser Leu Arg Ala Arg Arg Gly Val Ala Pro Arg Lys
1               5                   10                  15

Ala Ala Val Gly Arg Tyr Gln Leu Val Leu Ala Ile Thr Leu Ser Val
            20                  25                  30

Ala Leu Thr Gly Leu Val Thr Thr Gln Phe Val Leu Ser Thr Ser Leu
            35                  40                  45

Tyr Ser Thr Gln Glu Lys Gln Gln Arg Gln Gln His Lys Ser His Ala
    50                  55                  60

Lys Gly Pro Asn Pro Ser Asn Leu Arg Thr Asp Ser Phe Pro Arg Glu
65                  70                  75                  80

Gln Leu His Val Val Pro Glu Glu Gln Lys Gln Ser Glu Arg Arg
                85                  90                  95

Leu Asn Glu Ser Ser Arg Glu His Glu Ser Arg Glu Asn Asp His Glu
            100                 105                 110

Asp Glu Gln Lys Thr Arg Pro Asp Ser Glu Lys Lys Asp Asp Leu Leu
            115                 120                 125

Thr Gln Gln Asp Gln Lys Thr Thr Lys Arg Asn Glu His Gly Pro Ala
    130                 135                 140

Gln Glu Gly Ile Arg Lys His Lys Thr Asp His Glu Ala Pro Glu Lys
145                 150                 155                 160

Val Glu Ser Pro Val Asp Glu Asp His Glu Val Gln Lys Ala His Arg
                165                 170                 175

Glu Thr Val Gln Lys Phe Val Asp Asp Arg Arg Val Arg Leu Lys His
            180                 185                 190

Arg Ile Ser Arg Pro Lys Val Ala Arg Ala Ser Pro Pro Glu Val
            195                 200                 205

Glu Pro Gln Ile Glu Val Ala Pro Pro Glu Lys Arg Pro Tyr Asp
    210                 215                 220

Ile Leu Asp Asp Pro Leu Gln Asn Pro Asp Phe Asn Lys Pro Ser Lys
225                 230                 235                 240

Pro Leu Asn Phe Thr Ala Ala Val Pro Tyr Leu Gly Val Leu Ile Asp
                245                 250                 255

Gly Gly Arg His Phe Phe Pro Met Asp Trp Met Lys Arg Ala Val Asp
            260                 265                 270

Arg Leu Ser Asp Leu Arg Tyr Asn Leu Ile His Leu Arg Leu Thr Asp
            275                 280                 285

Asp Gln Ala Phe Asn Val Leu Leu Asp Ser His Pro Glu Leu Ala Tyr
    290                 295                 300

Pro Ala Ala Val Asn Asn Pro His Gln Gln Val Trp Thr Ala Ser Glu
305                 310                 315                 320

Leu Arg Asp Leu Thr Ala Tyr Ala Lys Ser Lys Gly Val Ser Ile Met
                325                 330                 335

Pro Glu Val Asn Val Pro Gly His Ala Gly Ala Trp Ala Gly Ile Pro
            340                 345                 350

His Leu Val Val His Cys Pro Glu Phe Ile Cys Gln Arg Gly Tyr Gly
            355                 360                 365

-continued

```
Leu Pro Leu Asn Val Thr His His Asp Leu Lys Pro Ile Leu Thr Ser
    370                 375                 380

Ile Leu Lys Glu Val Val Asp Ile Phe Asp Asp Pro Pro Phe Leu His
385                 390                 395                 400

Leu Gly Gly Asp Glu Val Asn Met Ala Gly Pro Cys Phe Asn Glu Val
                405                 410                 415

Arg Ser Pro Val Phe Asn Tyr Thr Ala Phe Glu Val Val Leu Lys Glu
            420                 425                 430

Ile Ile Ala Asp Val Gly Tyr Pro Glu Lys Gln Val Val Arg Trp Glu
        435                 440                 445

Met Thr Gly Gln Ala Asn Leu Glu Arg Ala Gly Gly Val Glu Gln Phe
    450                 455                 460

Trp Glu Ser Tyr Pro Gly Glu Arg His Lys Ala Ala Gly Pro Phe Phe
465                 470                 475                 480

Ile Ser Asn Arg Leu Tyr Phe Asp Thr Asn Gln Asp Gln Asn Ala Tyr
                485                 490                 495

Glu Val Trp Gln Asn Thr Arg Arg Phe Tyr Val Asn Asp Tyr Gln Pro
            500                 505                 510

Glu Ala Val Pro Thr Ala Ile Ile Ala Gly Thr Phe Glu Leu Ser Thr
        515                 520                 525

Thr Trp Trp Tyr Asp Arg Asn Ile Leu Gly Arg Leu Leu Ala Val Ala
    530                 535                 540

Leu Gly Ala Arg Asn Glu Thr Leu Pro Lys Thr Met Lys Asp Gln Asp
545                 550                 555                 560

His Glu Lys Met Val Leu Asp Gln Tyr Gln Val Phe Cys Asp Gln Leu
                565                 570                 575

Gly Tyr Ser Gln Ala Ile Cys Glu Thr Asn Gly Gly Pro Ile Ile Pro
            580                 585                 590

Thr Pro Glu Tyr Lys Lys Lys Trp Gly Asp Gly Trp Val Val Trp Lys
        595                 600                 605

Ala His Ile Cys Glu Arg Met Thr Thr Thr Glu Val Thr Lys Ala Met
    610                 615                 620

Arg Pro Arg Ser Ser Asp Arg Val Ala Thr Gln Ala Asn Ser Tyr Phe
625                 630                 635                 640

Trp Asn Val Phe Gly Phe Pro Ala His Thr His Thr Arg Val Gly Gln
                645                 650                 655

His Pro Thr Leu Pro Asp Asp Leu Gln Ala Leu Gln Arg His Leu Ile
            660                 665                 670

Pro His Cys Gly Val Met Leu Asp Thr Thr Arg Ser Leu Val Pro Ala
        675                 680                 685

Asp Arg Leu Gly Thr Ile Leu Thr Asp Thr Val Ala Lys Leu Gly Phe
    690                 695                 700

Asn Ile Ala Gln Leu Arg Leu Val Ser Asn Lys Gly Phe Thr Phe Ala
705                 710                 715                 720

Pro Ser Ser Leu Pro His Thr Val Gly His Ser Leu Leu Ala Thr Lys
                725                 730                 735

Glu Ile Lys Val Tyr Thr Arg Ser Asp Leu Met Gly Thr Val Ala Lys
            740                 745                 750

Ala Ser Ala Val Gly Ile Gln Met Ile Pro Glu Ile Ser Met Thr Thr
        755                 760                 765

Gly Ser Ala Gly Trp Tyr Glu Ser Gly Tyr Leu Ala Asn Cys Pro Asn
    770                 775                 780
```

```
Arg Leu Cys Glu Ile Gly Asp Ala Ser Ile Asp Val Thr Asn Pro Phe
785                 790                 795                 800

Leu Pro Pro Thr Val Tyr Ser Leu Ile Tyr Glu Leu Arg Ser Ile Phe
                805                 810                 815

Ser Ser Ser Pro Tyr Ile His Leu Gly Ser Asp Glu Arg Gln Asp Ala
            820                 825                 830

Ala Ala Cys Tyr Gln Glu Ala Asn Pro Thr Phe His Ala Asp Val Gly
        835                 840                 845

Ala Phe Glu Arg Lys Met Val Lys Val Leu Glu Ala Ser Gly Ile Ala
850                 855                 860

Asn Asp Ser Val Leu Arg Tyr Ala Asn Ser Gln Gly Glu Val Tyr Ser
865                 870                 875                 880

Asp Arg Thr Gly Gly Val Thr His Tyr Gly Pro Asp His Ala Thr Glu
                885                 890                 895

Ile Pro Ala Asp Ala Pro Ile Phe Val Ser Val Asp Leu Leu Arg Asp
            900                 905                 910

Asp Gly Trp Thr Leu Tyr Gln Arg Val Lys Glu Leu Val Ser Lys Lys
        915                 920                 925

Pro Leu Gly Ile Leu Ala Glu Ile Arg Thr Leu Thr Ala Pro Arg Trp
930                 935                 940

Glu Gly Leu Glu Ile Pro Glu Arg Leu Leu Val Tyr Ala Met Ala Val
945                 950                 955                 960

Ser Glu Leu Pro Thr Tyr Ala Asn Ala Ala Leu Gly Glu Arg Tyr
                965                 970                 975

Gly Glu Leu Cys Arg Ala Leu Ser Asp Arg Leu Pro Gly Leu Gly Arg
            980                 985                 990

Arg His Asp Cys Ala Leu Pro Gly Val Val Ser Gly Lys Val Thr Phe
        995                 1000                1005

Leu Ala Asp Thr Ser Thr Phe Val Gln Gln Gln Cys Gln Met Ala
    1010                1015                1020

Thr Tyr Pro Val Thr Gln His His Ala Lys Leu Val Ala Pro Arg
    1025                1030                1035

Tyr Asn Ala Thr Glu Trp Glu Gln Leu Arg Gly Ala Pro Arg Val
    1040                1045                1050

Phe Pro Ala Ala Gly Arg Asp Pro Gln Arg His His Pro Val Val
    1055                1060                1065

Ile Gly His Gly Lys Ser Gly Asp Glu Ser Pro Val Glu Ser Val
    1070                1075                1080

Ala Ser
    1085

<210> SEQ ID NO 10
<211> LENGTH: 3339
<212> TYPE: DNA
<213> ORGANISM: Phaeodactylum tricornutum

<400> SEQUENCE: 10
atgcaatctt ccttgcgcgc acgacgtggt gtggctcccc ggagaaaagc tgccgtcggt      60
cggtatcaac tggtcctcgc tattacgttg tccgtcgcct tgaccggtct cgtgacaact     120
caatttgtgc tgtcgacttc gttgtattcc actcaagaaa agcagcaacg acagcagcac     180
aagagccacg caaagggacc taatccatcc aatctaagga ccgattcttt cccgagagag     240
cagttgcacg tagttgtgcc ggaagaacag aaacaatcag gcggcgatt gaacgaaagc     300 agtcgggaac acgaatctcg agagaatgac catgaagacg agcaaaagac ccggcccgat     360
```

```
tcagagaaga aagatgatct tcttacgcag caggaccaaa agacgacgaa acgaaacgaa      420
catggtcctg ctcaggaagg catccgcaag cacaagactg accacgaggc tcccgaaaag      480
gtggaatcgc cagtggatga ggaccatgaa gtccaaaagg cacacagaga acagtgcaa       540 aaattcgtcg acgaccgaag agttcgcctc aagcacagaa tctctcgacc caaagtggcc      600
agggctgcat caccgcctga ggtggaaccg caaattgagg ttgctccgcc acccgaaaag      660
cgaccttatg acattctgga tgatcccttg caaaatccag atttcaacaa accctcgaag      720
ccgttgaact tcacggccgc tgtaccatat ttgggtgtac tgattgacgg ggggcgtcat      780
ttctttccaa tggactggat gaaacgagcc gttgatcgcc tttctgattt gcgctataat      840
ttgattcact tgcgtcttac ggacgaccaa gccttcaacg ttctattgga ttctcatccc      900
gagctcgctt atcccgccgc cgtcaacaac ccacaccagc aagtttggac ggccagcgaa      960
ttgcgtgact tgaccgctta cgcgaaatcc aaaggagtaa gcatcatgcc cgaagtcaac     1020
gttcccggac acgccggtgc ctgggccggt attcctcacc tagtcgtgca ctgtcccgaa     1080
ttcatctgcc aaagaggcta cggattgcca ctaaatgtaa cccatcacga tctcaaacct     1140
atcttgacga gtatcttgaa ggaagtcgtc gacattttg atgatccgcc ctttctacat      1200
ttgggtgggg atgaagtcaa cgtacgtttg ttttccgtgt ggaacttttc tgtgcgttgt     1260
cggaaggtat aaggcgtttc taaactttt tttctctacc agatggccgg ccctgtttt       1320 aacgaagttc gcagtcccgt ctttaattac acggctttcg aagttgttct taagaaatc      1380 attgccgatg taggctaccc cgaaaagcaa gtggttcgtt gggaaatgac cgggcaggct     1440
aatttggaac gcgctggcgg tgtggaacaa ttttgggagt cgtatccggg agaacggcac     1500
aaggctgcgg gacctttttt catttcgaac cgtttgtatt ttgatacaaa ccaggatcaa     1560
aatgcgtacg aagtttggca gaatacccga cggttttatg taaatgatta ccagcccgag     1620
gcagttccaa ccgccattat tgccggcacc tttgagttgt cgacgacttg gtggtacgat     1680
cgcaatattt tgggacgttt gttggctgtt gcgttgggtg cccgaaacga aactctacca     1740
aagacgatga aggaccaaga ccatgagaaa atggtgcttg atcaatacca gttttctgc      1800 gaccagttag gatatagcca ggcaatttgc gaaaccaacg gtggcccgat catccctacc     1860
ccggagtaca aaagaaatg gggtgacggt tgggtagttt ggaaggcgca catctgtgaa     1920
cgcatgacga cgactgaggt aaccaaggca atgcgacccc gctctagcga ccgggtcgcc     1980
acgcaggcga acagctactt ttggaacgta tttggatttc ctgcgcacac acacacgcga     2040
gtgggccagc atccaacgtt gccagacgat ctccaggccc tccagcgaca tttaattcct     2100
cattgtggcg ttatgttgga tacgaccaga tccctggttc cagcggatcg gttgggaacg     2160
attttgaccg acaccgttgc aaaattgggt ttcaacatag cccagctgcg tttggtcagc     2220
aacaagggct tcacgtttgc tccgagtagt ctaccgcata ctgtaggcca ttcgttacta     2280
gcaacgaagg agatcaaggt atacactagg agtgacttga tgggtaccgt tgctaaagcg     2340
agtgcggtgg gaatccaaat gatccccgaa atcagcatga cgacaggaag tgctggttgg     2400
tacgagtcgg gctatctagc gaattgtcca aaccgtctgt gtgaaattgg tgacgcgtcg     2460
attgacgtga cgaacccgtt cttaccaccc accgtgtact cgttgatcta cgagttgcgt     2520 tccatttca gcagcagtcc ctatattcat ctcggttcgg acgagcgtca agacgcggca     2580
gcttgctacc aagaagccaa tcccacgttc cacgcggacg tggagcgtt cgagcgcaaa      2640 atggtcaaag tcttggaggc gagcgggatt gcgaacgatt ctgtactgcg gtacgccaat     2700
```

```
tcgcaaggcg aggtgtacag cgaccggacg ggtggcgtca cacactacgg tccggaccat    2760
gcgacggaga ttcctgcgga cgcaccaata tttgtgagtg tggatttgtt gcgggacgat    2820
gggtggacat tgtaccagcg ggtgaaggaa ctcgtatcga aaaagccgtt gggcatcttg    2880
gcggaaatcc gtacgttgac ggctccccgt gggaaggcc tggagattcc ggaacgtttg     2940
ctggtgtacg ccatggccgt atcggaattg cccacgtacg cgaacgcggc ggcactgggc    3000
gagcggtacg gggagctttg ccgggcgtta tcggatcgat tgccgggatt gggtcgtcgg    3060
cacgattgcg cgttgccggg tgtcgtctcg gggaaggtga cgttttttggc cgacacgagt   3120 acctttgtgc agcagcagtg tcaaatggcg acgtatcccg tgacgcaaca ccacgccaag    3180
ttggtagcac cccggtacaa cgcgaccgag tgggagcaac tgcgcggggc ccccgcgtg    3240 tttccggcgg cgggtcggga tccccagcgg catcaccccg tcgtcatcgg gcatggaaaa    3300
tcgggggacg agtccccggt cgagtccgta gctagctag                          3339
```

<210> SEQ ID NO 11
<211> LENGTH: 973
<212> TYPE: PRT
<213> ORGANISM: Phaeodactylum tricornutum

<400> SEQUENCE: 11

```
Met Glu Ser Ala Arg Ser Arg Asn Thr Arg Asp Gly Thr Arg Lys Gln
1               5                   10                  15

Gly Thr Ala Arg Arg Ser Gly Gly Thr Thr Ser Ser Asn Gly Asn Gln
                20                  25                  30

Gly Phe Asp Glu Phe Gly Phe Gly Gln Pro Ala Phe Pro Asp Ser Ala
            35                  40                  45

Phe Asp Asn His Gly Phe Glu Met Pro Gln Thr Arg Ile Gln Pro Thr
        50                  55                  60

Lys Ile Arg Ser Arg Arg Arg Ala Ser Leu Ala Ala Ala Pro Asn Ile
65                  70                  75                  80

Asp Val Val Ser Glu Asn Pro Ser Ile Gly Phe Thr Asn Gln Phe Gln
                85                  90                  95

Ser Ser Gln Asp Glu Gln Val Ser Arg Gly Gly Ala Arg Leu Ala Lys
            100                 105                 110

Ala Gly Arg Ser Ser Arg Ser Met Asp Gly Ile Glu Phe Pro Thr Ala
        115                 120                 125

Arg Lys Asp Val Ser Ser Gln Asn Arg Pro Arg Arg Ser Gly Arg Arg
    130                 135                 140

Ala Ser Met Ala Thr Ser Ser Asn His Ser Leu Ser Ala Ser Asn His
145                 150                 155                 160

Thr Asn Pro Glu Leu Gly Tyr Gly Asp Ala Ile Pro Ser Val Ala Ala
                165                 170                 175

Asn His Arg Lys Gly Asp Ser Asn Ser Gly Ile Leu Asp Phe Gly Phe
            180                 185                 190

Gly Gly Gly Lys Asn Ala Gly Thr Ala Asn Ala Asp Tyr Gly Tyr Gly
        195                 200                 205

Asp Thr Met Ser Ser Gly Phe Gly Asn Phe Glu Ser Met Pro Ser Ala
    210                 215                 220

Pro Ser Thr Thr Pro Glu Ser Glu Arg Pro Arg Ser Gly Arg Arg
225                 230                 235                 240

Ser Ser Ile Ser Gly Gly Leu Glu Ser Leu Arg Ser Asp Leu Arg Gly
                245                 250                 255

Gly Asp Leu Ser Gly Ala Pro Ser Ser Arg Val Leu Gly Gly Asn Ser
```

-continued

```
                260                 265                 270
Arg Ala Gln Asn Ile Val Leu Pro Met Ala Gly Pro Glu Lys Val Ala
            275                 280                 285
Gly Gly Asn Val Arg Gly Arg Arg Gly Ser Leu Leu Gly Ser Val
        290                 295                 300
Gly Asn Ala Val Gly Ala Thr Met Gly Gly Phe Thr Gly Gly Asn Lys
305                 310                 315                 320
Asp Lys Glu Lys Leu Asp Asp Asp Thr Thr Lys Lys Ser Lys Ser Phe
                325                 330                 335
Leu Lys Asp Arg Lys Ala Glu Gly Arg Arg Gly Thr Thr Arg Gln Pro
                340                 345                 350
Ser Ala Asp Gly Asn Ile Ile Ser Ser Tyr Thr Gly Asp Arg Asp Arg
            355                 360                 365
Arg Arg Lys Pro Ala Ala Ser Ser Lys Thr Leu Gly Lys Glu Ser Asn
        370                 375                 380
Val Ser Tyr Ser Asp Arg Ile Leu Ala Gln Arg Asp Cys Ser Cys Gly
385                 390                 395                 400
Gly Glu Gly Ser Ser Ser Gly Ser Gly Ser Ser Asp Gly Ser Ser
                405                 410                 415
Ala Cys Cys Arg Ser Lys Ile Trp Pro Ala Ala Arg Cys Glu Thr Tyr
                420                 425                 430
Arg Thr Leu Glu Ile Asp Ala Ser Ser Ser Met Thr Leu Arg Arg His
            435                 440                 445
Gly Leu Arg Gly Leu His Ile Ser Pro Thr Gln Ser Val Gly Asp Glu
        450                 455                 460
Ser Ser Phe Asp Val Asp Cys His Gly Tyr Cys Gln Asp Val Gln Ser
465                 470                 475                 480
Ile Leu Asp Ala Ala Tyr Val Arg Phe Leu Lys Ala Leu Arg Arg Ser
                485                 490                 495
Val Ser Ser Thr Pro Leu Ala His His Asp Arg Arg Glu Asn Glu Lys
                500                 505                 510
Val Ala Gln His Asp Asn Val Gln Ala Leu Leu Gly Ile His Ile Ser
            515                 520                 525
Ile Thr Thr Asn Glu Ser Ala Leu Val His Asp Ala Asp Glu Arg Tyr
        530                 535                 540
Gln Leu Asp Val Pro Gly Pro Thr Val Thr Glu Asn Asp Asp Asp Asp
545                 550                 555                 560
Asp Gly Ser Tyr Ile His Leu Thr Ala Pro Thr Val Tyr Gly Ile Leu
                565                 570                 575
His Ala Tyr Gln Ser Leu Leu Gln Leu Val Thr Phe Val Gly Arg Asp
                580                 585                 590
Ser Gln Thr Gly Ala Phe Val Phe Ala Met Pro Asp Thr Thr Leu Ile
            595                 600                 605
Arg Ile Arg Asp Gly Pro Val Tyr Pro Tyr Arg Gly Leu Met Ile Asp
        610                 615                 620
Thr Ala Arg His Phe Leu Pro Leu Pro Leu Ile Leu Gln Asn Leu Asp
625                 630                 635                 640
Ala Met Glu Ala Ser Lys Leu Asn Val Leu His Trp His Val Thr Asp
                645                 650                 655
Ser Gln Ser Trp Pro Tyr Val Ser Thr Ala Phe Pro Glu Leu Ser Ala
                660                 665                 670
Arg Gly Ala Phe Gly Pro Glu Thr Tyr Thr Ala Thr Asp Ile Ala
            675                 680                 685
```

```
Leu Val Val Arg Glu Ala Ala Arg Ala Ile Gly Arg Ser His Pro
        690                 695                 700

Glu Trp Leu Thr Pro Cys Gly Ser Lys Pro Arg Pro Gln Glu Pro Leu
705                 710                 715                 720

Asp Ala Thr Asn Pro Ala Val Tyr Glu Phe Val His Arg Leu Tyr Asp
                725                 730                 735

Glu Leu Ala Ile Leu Phe Ala His Glu Ser Phe Leu His Val Gly Gly
            740                 745                 750

Asp Glu Val Asn Leu Asp Cys Tyr His Asn Ser Thr Val Gln Arg
        755                 760                 765

Trp Met Arg Lys His Asn Met Thr Gln Glu Leu Glu Val Leu Ser Tyr
770                 775                 780

Phe Glu Arg Asp Leu Leu Ser Tyr Val Thr Ala Val Leu Asn Arg Arg
785                 790                 795                 800

Pro Ile Val Trp Gln Glu Leu Phe Asp Ser Gly Leu Gly Leu Pro Asn
                805                 810                 815

Gln Thr Ile Val Asp Val Trp Lys Ser Trp Glu Pro Ser Ser Arg Tyr
            820                 825                 830

Asn Ala Thr Leu Arg Gly His Glu Val Ile Leu Ser Ser Cys Trp Tyr
        835                 840                 845

Leu Asp His Leu Asn Glu Asp Trp Gln Ser Phe Tyr Ala Cys Asp Pro
850                 855                 860

Arg Glu Phe Asn Gly Thr Lys Glu Gln Lys Asn Leu Ile Leu Gly Gly
865                 870                 875                 880

His Ala Ser Met Trp Gly Glu Arg Val Asp Ala Thr Asn Phe Leu Ser
                885                 890                 895

Arg Val Trp Pro Arg Ala Ser Ala Thr Ala Glu Lys Leu Trp Thr Gly
            900                 905                 910

Asn Leu Thr Ala Ala Ala Asp Ser Ala Ala Ser Arg Leu Ala Ala Phe
        915                 920                 925

Arg Cys His Leu Val Arg Arg Gly Ile Pro Ala Ser Pro Val Gly Pro
930                 935                 940

Gly Ala Ser Cys Gly Arg Gln Pro Asn Gly Phe Pro Ala Val Ile Asp
945                 950                 955                 960

Ser Phe His Asp Glu Glu Leu Gln Glu Gly Lys Val Thr
                965                 970

<210> SEQ ID NO 12
<211> LENGTH: 3341
<212> TYPE: DNA
<213> ORGANISM: Phaeodactylum tricornutum

<400> SEQUENCE: 12
atggaatctg ctcgctctcg aaatacccgg gatggcaccc gaaagcaagg tacggcacga      60
agaagtggcg gtactactag tagcaatggc aatcaaggct tcgacgagtt tggatttggt     120
caacctgcct ttccggattc tgcgtttgac aaccacggct ttgagatgcc gcaaactcga     180
attcagccaa cgaagattcg ttcccgccgt cgagcatctt tagctgcggc gccgaacatt     240
gacgttgtgt cggaaaaccc gtcaataggt tttaccaatc aatttcaatc ttcacaagac     300
gaacaggtgt ctcgtggtgg agcccgcttg caaaggcgg gacgctcatc gcgctcaatg     360
gacggcatcg aattcccaac tgcacgcaag gacgtttcta gtcaaaatcg tcctcgtcgt     420
tcgggtcgcc gggcttcaat ggctactcct tccaaccaca gcctttccgc ttccaatcac     480
```

```
accaacccgg aactcggtta cggagacgcc attccgtctg ttgctgctaa ccatagaaaa    540
ggagactcta atagcggaat tttggacttc ggctttggtg gtggtaagaa tgccggtaca    600
gccaatgccg actacggcta cggtgacaca atgtcgtcgg gttttggtaa tttcgagtct    660
atgccatccg cgccttccac cacacccgaa tctgaacgtc cgcgtcgcag cggacgacgc    720
tccagtatca gtggaggtct tgaaagtcta cggtctgact tgcgcggagg cgacctgagt    780
ggtgctccgt ctagtcgggt gttgggtgga aattctcgcg cccagaacat tgtgttgccc    840
atggccgggc cggaaaaagt ggccggtggc aatgttcgtc gtggacgtcg cggatcctta    900
ctgggtagtg ttggtaatgc agtcggagct accatggggg gattcactgg tggaaataag    960
gacaaggaaa aactcgacga cgataccacc aaaaagtcta agtcttttct aaaggatcgc   1020
aaggctgaag gtcggcgagg cacgacacgt caaccatcgg ccgatggcaa tataatctct   1080
tcctataccg gcgatcgcga ccgacgccgc aagccggcag cgtcgtccaa gaccctgggc   1140
aaagagagca acgtgtcgta ctcggatcgt attttagcac agcggtaaga ggcaacataa   1200
aaacacagca attcaataat ttggcggtgt acagactacc aatctaaatg tttaaagcct   1260
agcggtatag tccgctcggc caagatatag aagggcaggg aattgcagca agtaaaggc    1320
atattagatt cagtgtacgt gatgtaccgg gaccagtgtg agagaataaa ggtccgaatg   1380
tgactcgccc gagatcgcgg aatcgcagaa aaacccgaga cactgtcaat ccgtttcttc   1440
gcgaaatcct ggccgctttc gcgcatttac attacatagt tcgcaccatg tgggggagac   1500
gaggactttg tcgtatttct cttctaacgt tgctattatt actattcgtt tctaacagtg   1560
actgtagttg tggaggtgaa gggagcagca gtagcggtag cggtagcagt gacggtagta   1620
gtgcttgttg tcgcagcaaa atttggccgg cggctcgatg tgaaacctac cgaacactcg   1680
aaatcgatgc ttcctcctct atgacattgc gacggcacgg cttgcgagga ctgcatatct   1740
cccctactca aagcgtaggg gacgaaagta gcttcgatgt ggactgccat ggatattgtc   1800
aagacgttca atcgatactg gacgccgcgt acgttcgctt tctcaaggcg ctccggcgaa   1860
gcgtgtcttc cacgcctttg gcgcatcacg accgtcgcga aaatgaaaag gtcgctcaac   1920
atgacaacgt acaggctctg ttgggcattc acatttccat tactacgaat gagtctgcac   1980
tcgtacacga cgcggacgaa cgataccaac tggacgtccc agggcctacc gtcactgaaa   2040
acgacgacga cgacgatggc agctacattc atctcactgc acccaccgtc tacggcattc   2100
tgcacgccta ccaaagctta ctgcagctgg tgacgtttgt tggtagggac tctcaaacag   2160
gcgctttcgt attcgccatg ccggacacaa ccctcattcg aatccgtgat ggacccgtgt   2220
atccctaccg gggactcatg atcgacacgg cccgacattt tttgccacta ccgcttatct   2280
tgcaaaactt ggacgccatg gaggccagta aactgaacgt cttgcactgg cacgtgactg   2340
attcgcagtc gtggccctac gtcagtactg cttttccgga gcttagtgct cggggagcct   2400
ttggtcctga agaaacctac acggctacag atattgccct cgtcgtgcgg gaagccgccg   2460
cacgggggtat tcgggtgatt cctgaattcg atttgcctgg acactcgtaa gcgattggac   2520
gctcacatcc ggaatggtta acaccctgtg ggtccaagcc acggccgcaa gaacctttgg   2580
atgcgaccaa tccggccgtc tacgaattcg tacaccgcct ctacgacgaa ttggcaatac   2640
tctttgcgca cgaatccttt ttacacgtcg gaggagacga agtcaattta gattgttacc   2700
acaatagcac gacggtccaa agatggatgc gaaaacacaa tatgacacag gaacttgagg   2760
ttctgagcta ttttgagcgt gatttgcttt cgtacgtcac cgctgtatta aatcgtcgtc   2820
ccattgtgtg gcaggaactc ttcgattcgg gattgggtct tcccaatcag acaattgtcg   2880
```

```
atgtctggaa atcgtgggaa ccttcgtcgc gatacaacgc cactttgcgg ggccacgaag    2940
ttattttgtc ctcgtgctgg tatctcgatc atttgaacga agattggcaa agcttctacg    3000
cctgtgatcc acgggagttc aacggtacga agaacagaa gaacttgatt ctgggcggtc    3060
acgcttccat gtgggggaa cgggtggatg cgaccaactt tctatctcgt gtttggcccc    3120
gtgccagtgc tacggccgaa aagctgtgga caggcaactt aacagctgcg gcggattcgg    3180
cggcttctcg attggccgcc tttcgctgtc atttggtccg cagaggaatt ccggccagtc    3240
cggtcggtcc gggagcaagt tgcggcagac aaccaaatgg ttttccggct gtgatcgata    3300
gctttcatga cgaggagttg caggaaggaa aggttacttg a                        3341
```

<210> SEQ ID NO 13
<211> LENGTH: 442
<212> TYPE: PRT
<213> ORGANISM: Mus musculus

<400> SEQUENCE: 13

```
Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Ser Asp Ala Leu Gly Pro Pro Leu Leu Asp Ala Glu Pro Val Arg
        35                  40                  45

Gly Ala Gly His Leu Ala Val Ser Val Gly Ile Arg Arg Val Ser Asn
    50                  55                  60

Glu Ser Ala Ala Pro Leu Val Pro Ala Val Pro Arg Pro Glu Val Asp
65                  70                  75                  80

Asn Leu Thr Leu Arg Tyr Arg Ser Leu Val Tyr Gln Leu Asn Phe Asp
                85                  90                  95

Gln Met Leu Arg Asn Val Gly Asn Asp Gly Thr Trp Ser Pro Gly Glu
            100                 105                 110

Leu Val Leu Val Val Gln Val His Asn Arg Pro Glu Tyr Leu Arg Leu
        115                 120                 125

Leu Ile Asp Ser Leu Arg Lys Ala Gln Gly Ile Gln Glu Val Leu Val
    130                 135                 140

Ile Phe Ser His Asp Phe Trp Ser Ala Glu Ile Asn Ser Leu Ile Ser
145                 150                 155                 160

Arg Val Asp Phe Cys Pro Val Leu Gln Val Phe Phe Pro Phe Ser Ile
                165                 170                 175

Gln Leu Tyr Pro Asn Glu Phe Pro Gly Ser Asp Pro Arg Asp Cys Pro
            180                 185                 190

Arg Asp Leu Lys Lys Asn Ala Ala Leu Lys Leu Gly Cys Ile Asn Ala
        195                 200                 205

Glu Tyr Pro Asp Ser Phe Gly His Tyr Arg Glu Ala Lys Phe Ser Gln
    210                 215                 220

Thr Lys His His Trp Trp Lys Leu His Phe Val Trp Glu Arg Val
225                 230                 235                 240

Lys Val Leu Gln Asp Tyr Thr Gly Leu Ile Leu Phe Leu Glu Glu Asp
                245                 250                 255

His Tyr Leu Ala Pro Asp Phe Tyr His Val Phe Lys Lys Met Trp Lys
            260                 265                 270

Leu Lys Gln Gln Glu Cys Pro Gly Cys Asp Val Leu Ser Leu Gly Thr
        275                 280                 285
```

Tyr Thr Thr Ile Arg Ser Phe Tyr Gly Ile Ala Asp Lys Val Asp Val
        290                 295                 300

Lys Thr Trp Lys Ser Thr Glu His Asn Met Gly Leu Ala Leu Thr Arg
305                 310                 315                 320

Asp Ala Tyr Gln Lys Leu Ile Glu Cys Thr Asp Thr Phe Cys Thr Tyr
            325                 330                 335

Asp Asp Tyr Asn Trp Asp Trp Thr Leu Gln Tyr Leu Thr Leu Ala Cys
        340                 345                 350

Leu Pro Lys Ile Trp Lys Val Leu Val Pro Gln Ala Pro Arg Ile Phe
    355                 360                 365

His Ala Gly Asp Cys Gly Met His His Lys Lys Thr Cys Arg Pro Ser
370                 375                 380

Thr Gln Ser Ala Gln Ile Glu Ser Leu Leu Asn Ser Asn Lys Gln Tyr
385                 390                 395                 400

Leu Phe Pro Glu Thr Leu Val Ile Gly Glu Lys Phe Pro Met Ala Ala
            405                 410                 415

Ile Ser Pro Pro Arg Lys Asn Gly Gly Trp Gly Asp Ile Arg Asp His
        420                 425                 430

Glu Leu Cys Lys Ser Tyr Arg Arg Leu Gln
435                 440

<210> SEQ ID NO 14
<211> LENGTH: 447
<212> TYPE: PRT
<213> ORGANISM: Homo sapiens

<400> SEQUENCE: 14

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Gly Asp His Pro Ser Val Ala Val Gly Ile
    50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
        115                 120                 125

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Ile Pro Arg Ile Phe His Ala Gly Asp Cys Gly Met His His Lys Lys
370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Arg Leu Gln
        435                 440                 445

<210> SEQ ID NO 15
<211> LENGTH: 334
<212> TYPE: PRT
<213> ORGANISM: Phaeodactylum tricornutum

<400> SEQUENCE: 15

Arg Ser Tyr Ala Ser Arg Lys Thr Arg Glu Ile Lys Asn Arg Arg Phe
1               5                   10                  15

Thr Met Lys Asn Thr Asp Ile Pro Phe Val Leu Met Val Tyr Lys Arg
                20                  25                  30

Val Asp Tyr Leu Lys Lys Ala Ile Asp Ser Val Arg Arg Ser Asp Phe
            35                  40                  45

Pro Lys Ser Arg Val Pro Leu Ile Ile Ser His Asp Gly Arg Val Pro
        50                  55                  60

Glu Val Val Glu Tyr Val Glu Ser Leu Lys Asp Glu Phe Lys Ile Ile
65                  70                  75                  80

Gln Leu Ile His Pro His Ser Cys Tyr Glu His Pro Asn Glu Phe Pro
                85                  90                  95

Gly Asp Asp Pro Thr Leu Asn Glu Gly Phe Ala Gly Asp Ser Tyr Gly
            100                 105                 110

Asn Pro Arg Ser Ala Trp Ile Thr Cys Cys Lys His His Phe Thr Trp
        115                 120                 125

Met Leu His Thr Val Phe Arg Arg Asp Phe Asp Pro Ala Val Asp
130                 135                 140

Thr Phe Leu Phe Leu Glu Glu Asp Tyr Ile Val Ala Pro Thr Ile Tyr 145                 150                 155                 160
Ser Ala Val Ile Ala Gly Leu Asn Val Met Glu Asp Met Asp Lys Glu
                165                 170                 175

Ile Pro Gly Gly Phe Gly Leu Gly Met Asp Pro Ser Met Ala Asn
            180                 185                 190

Thr Ala Phe Glu Pro Tyr Tyr Lys Lys Ala Thr Trp Tyr Val Glu Ala
                195                 200                 205

Phe Lys Ser Gly Pro Met Thr Met Asn Arg Asp Met Phe Lys Lys Leu
        210                 215                 220

Gln Gln His Ala Lys Glu Tyr Cys Thr Phe Asp Asp Tyr Asn Trp Asp
225                 230                 235                 240

Trp Ser Ile Val His Leu Gln Ser Lys Lys Leu Leu Pro Arg Thr Leu
                245                 250                 255

Leu Met Pro Ser Lys Val Leu Ala Lys His Ile Gly Val Lys Glu Gly
                260                 265                 270

Met His Thr Asn Lys Ser Phe Gly Lys Asp Phe Ser Asp Leu Phe Pro
            275                 280                 285

Asn Tyr Ala Pro Arg Arg Glu Gln Leu Thr Thr His Phe Ala Glu Tyr
            290                 295                 300

Arg Phe Thr Gly Asn Thr Ala Ala Ala Leu His Thr Glu Phe Asn Pro
305                 310                 315                 320

Gly Tyr Gly Gly Trp Gly His Pro Lys Asp His Glu His Cys
                325                 330

<210> SEQ ID NO 16
<211> LENGTH: 1002
<212> TYPE: DNA
<213> ORGANISM: Phaeodactylum tricornutum

<400> SEQUENCE: 16
agatcgtacg catcgcgcaa acccgtgaa atcaagaatc gtcgctttac aatgaagaac      60
acggacatcc cgttcgtatt gatggtttat aagcgcgtgg attatttgaa aaaggcgatt     120
gattcggtcc gtcgatccga ctttccaaag tctcgtgtgc ctcttatcat ttcgcacgat     180
ggacgagtgc cggaagtcgt tgagtatgtc gaatcgctga agacgagtt caaaattatc      240
caactcattc atccgcattc ttgctacgag catcccaacg agtttcctgg ggatgatccc     300
acactcaacg aaggctttgc tggagatagc tatggtaatc cacggagtgc gtggatcacc     360
tgctgcaaac atcattttac ttggatgctt cacactgtct ttcgtcggga ctttacggac     420
ccagcagtgg atacattttt gtttctcgaa gaagattaca cgtggctcc tacgatttat      480
tccgccgtta ttgctgggtt gaatgttatg gaagacatgg acaaggagat tccgggcggc     540
ttcttcggtt tgggtatgga tccgagtatg gcgaatactg cctttgagcc ttactacaag     600
aaggcgacgt ggtatgtcga agcattcaag tcaggtccga tgacgatgaa ccgggacatg     660
ttcaaaaagc tccaacaaca tgctaaggag tactgtacgt tcgacgatta caattgggat     720
tggtccattg tccatctaca agtaaaaag ttactaccac ggactcttct catgccaagc     780
aaagtcctag caaacatat tggtgtcaag gagggtatgc acacgaacaa atcctttgga     840
aaagactttt cagattatt tcccaactat gcccctcgtc gcgagcagct gaccacgcat     900
tttgcggaat accgttttac cgggaacacc gcggcagctt acacaccga attcaatccc     960
ggttatggtg gttggggaca tccgaaagac cacgagcact gc                      1002

<210> SEQ ID NO 17

<211> LENGTH: 538
<212> TYPE: PRT
<213> ORGANISM: Mus musculus

<400> SEQUENCE: 17

```
Met Lys Met Arg Arg Tyr Lys Leu Phe Leu Met Phe Cys Met Ala Gly
1               5                   10                  15

Leu Cys Leu Ile Ser Phe Leu His Phe Phe Lys Thr Leu Ser Tyr Val
            20                  25                  30

Thr Phe Pro Arg Glu Leu Ala Ser Leu Ser Pro Asn Leu Val Ser Ser
        35                  40                  45

Phe Phe Trp Asn Asn Ala Pro Val Thr Pro Gln Ala Ser Pro Glu Pro
    50                  55                  60

Gly Gly Pro Asp Leu Leu Arg Thr Pro Leu Tyr Ser His Ser Pro Leu
65                  70                  75                  80

Leu Gln Pro Leu Ser Pro Ser Lys Ala Thr Glu Leu His Arg Val
                85                  90                  95

Asp Phe Val Leu Pro Glu Asp Thr Thr Glu Tyr Phe Val Arg Thr Lys
                100                 105                 110

Ala Gly Gly Val Cys Phe Lys Pro Gly Thr Arg Met Leu Glu Lys Pro
            115                 120                 125

Ser Pro Gly Arg Thr Glu Glu Lys Pro Glu Val Ser Glu Gly Ser Ser
        130                 135                 140

Ala Arg Gly Pro Ala Arg Pro Met Arg His Val Leu Ser Thr Arg
145                 150                 155                 160

Glu Arg Leu Gly Ser Arg Gly Thr Arg Arg Lys Trp Val Glu Cys Val
                165                 170                 175

Cys Leu Pro Gly Trp His Gly Pro Ser Cys Gly Val Pro Thr Val Val
            180                 185                 190

Gln Tyr Ser Asn Leu Pro Thr Lys Glu Arg Leu Val Pro Arg Glu Val
        195                 200                 205

Pro Arg Arg Val Ile Asn Ala Ile Asn Ile Asn His Glu Phe Asp Leu
    210                 215                 220

Leu Asp Val Arg Phe His Glu Leu Gly Asp Val Val Asp Ala Phe Val
225                 230                 235                 240

Val Cys Glu Ser Asn Phe Thr Ala Tyr Gly Glu Pro Arg Pro Leu Lys
                245                 250                 255

Phe Arg Glu Met Leu Thr Asn Gly Thr Phe Glu Tyr Ile Arg His Lys
            260                 265                 270

Val Leu Tyr Val Phe Leu Asp His Phe Pro Pro Gly Gly Arg Gln Asp
        275                 280                 285

Gly Trp Ile Ala Asp Asp Tyr Leu Arg Thr Phe Leu Thr Gln Asp Gly
    290                 295                 300

Val Ser Arg Leu Arg Asn Leu Arg Pro Asp Asp Val Phe Ile Ile Asp
305                 310                 315                 320

Asp Ala Asp Glu Ile Pro Ala Arg Asp Gly Val Leu Phe Leu Lys Leu
                325                 330                 335

Tyr Asp Gly Trp Thr Glu Pro Phe Ala Phe His Met Arg Lys Ser Leu
            340                 345                 350

Tyr Gly Phe Phe Trp Lys Gln Pro Gly Thr Leu Glu Val Ser Gly
        355                 360                 365

Cys Thr Met Asp Met Leu Gln Ala Val Tyr Gly Leu Asp Gly Ile Arg
370                 375                 380

Leu Arg Arg Arg Gln Tyr Tyr Thr Met Pro Asn Phe Arg Gln Tyr Glu
```

```
                385                 390                 395                 400
Asn Arg Thr Gly His Ile Leu Val Gln Trp Ser Leu Gly Ser Pro Leu
                405                 410                 415

His Phe Ala Gly Trp His Cys Ser Trp Cys Phe Thr Pro Glu Gly Ile
            420                 425                 430

Tyr Phe Lys Leu Val Ser Ala Gln Asn Gly Asp Phe Pro Arg Trp Gly
                435                 440                 445

Asp Tyr Glu Asp Lys Arg Asp Leu Asn Tyr Ile Arg Ser Leu Ile Arg
            450                 455                 460

Thr Gly Gly Trp Phe Asp Gly Thr Gln Gln Glu Tyr Pro Pro Ala Asp
465                 470                 475                 480

Pro Ser Glu His Met Tyr Ala Pro Lys Tyr Leu Leu Lys Asn Tyr Asp
                485                 490                 495

Gln Phe Arg Tyr Leu Leu Glu Asn Pro Tyr Arg Glu Pro Lys Ser Thr
            500                 505                 510

Glu Glu Gly Gly Arg Arg Asn Gln Gly Ser Asp Gly Arg Pro Ser Ala
                515                 520                 525

Val Arg Gly Lys Leu Asp Thr Val Glu Gly
530                 535

<210> SEQ ID NO 18
<211> LENGTH: 533
<212> TYPE: PRT
<213> ORGANISM: Homo sapiens

<400> SEQUENCE: 18

Met Lys Met Arg Arg Tyr Lys Leu Phe Leu Met Phe Cys Met Ala Gly
1               5                   10                  15

Leu Cys Leu Ile Ser Phe Leu His Phe Phe Lys Thr Leu Ser Tyr Val
                20                  25                  30

Thr Phe Pro Arg Glu Leu Ala Ser Leu Ser Pro Asn Leu Val Ser Ser
            35                  40                  45

Phe Phe Trp Asn Asn Ala Pro Val Thr Pro Gln Ala Ser Pro Glu Pro
    50                  55                  60

Gly Gly Pro Asp Leu Leu Arg Thr Pro Leu Tyr Ser His Ser Pro Leu
65                  70                  75                  80

Leu Gln Pro Leu Pro Pro Ser Lys Ala Ala Glu Glu Leu His Arg Val
                85                  90                  95

Asp Leu Val Leu Pro Glu Asp Thr Thr Glu Tyr Phe Val Arg Thr Lys
            100                 105                 110

Ala Gly Gly Val Cys Phe Lys Pro Gly Thr Lys Met Leu Glu Arg Pro
            115                 120                 125

Pro Pro Gly Arg Pro Glu Glu Lys Pro Glu Gly Ala Asn Gly Ser Ser
        130                 135                 140

Ala Arg Arg Pro Pro Arg Tyr Leu Leu Ser Ala Arg Glu Arg Thr Gly
145                 150                 155                 160

Gly Arg Gly Ala Arg Arg Lys Trp Val Glu Cys Val Cys Leu Pro Gly
                165                 170                 175

Trp His Gly Pro Ser Cys Gly Val Pro Thr Val Val Gln Tyr Ser Asn
            180                 185                 190

Leu Pro Thr Lys Glu Arg Leu Val Pro Arg Glu Val Pro Arg Arg Val
        195                 200                 205

Ile Asn Ala Ile Asn Val Asn His Glu Phe Asp Leu Leu Asp Val Arg
    210                 215                 220
```

```
Phe His Glu Leu Gly Asp Val Val Asp Ala Phe Val Val Cys Glu Ser
225                 230                 235                 240

Asn Phe Thr Ala Tyr Gly Glu Pro Arg Pro Leu Lys Phe Arg Glu Met
            245                 250                 255

Leu Thr Asn Gly Thr Phe Glu Tyr Ile Arg His Lys Val Leu Tyr Val
            260                 265                 270

Phe Leu Asp His Phe Pro Pro Gly Arg Gln Asp Gly Trp Ile Ala
        275                 280                 285

Asp Asp Tyr Leu Arg Thr Phe Leu Thr Gln Asp Gly Val Ser Arg Leu
290                 295                 300

Arg Asn Leu Arg Pro Asp Asp Val Phe Ile Ile Asp Ala Asp Glu
305                 310                 315                 320

Ile Pro Ala Arg Asp Gly Val Leu Phe Leu Lys Leu Tyr Asp Gly Trp
            325                 330                 335

Thr Glu Pro Phe Ala Phe His Met Arg Lys Ser Leu Tyr Gly Phe Phe
            340                 345                 350

Trp Lys Gln Pro Gly Thr Leu Glu Val Val Ser Gly Cys Thr Val Asp
        355                 360                 365

Met Leu Gln Ala Val Tyr Gly Leu Asp Gly Ile Arg Leu Arg Arg Arg
370                 375                 380

Gln Tyr Tyr Thr Met Pro Asn Phe Arg Gln Tyr Glu Asn Arg Thr Gly
385                 390                 395                 400

His Ile Leu Val Gln Trp Ser Leu Gly Ser Pro Leu His Phe Ala Gly
            405                 410                 415

Trp His Cys Ser Trp Cys Phe Thr Pro Glu Gly Ile Tyr Phe Lys Leu
            420                 425                 430

Val Ser Ala Gln Asn Gly Asp Phe Pro Arg Trp Gly Asp Tyr Glu Asp
            435                 440                 445

Lys Arg Asp Leu Asn Tyr Ile Arg Gly Leu Ile Arg Thr Gly Gly Trp
        450                 455                 460

Phe Asp Gly Thr Gln Gln Glu Tyr Pro Pro Ala Asp Pro Ser Glu His
465                 470                 475                 480

Met Tyr Ala Pro Lys Tyr Leu Leu Lys Asn Tyr Asp Arg Phe His Tyr
            485                 490                 495

Leu Leu Asp Asn Pro Tyr Gln Glu Pro Arg Ser Thr Ala Ala Gly Gly
            500                 505                 510

Trp Arg His Arg Gly Pro Glu Gly Arg Pro Pro Ala Arg Gly Lys Leu
            515                 520                 525

Asp Glu Ala Glu Val
        530

<210> SEQ ID NO 19
<211> LENGTH: 535
<212> TYPE: PRT
<213> ORGANISM: Mus musculus

<400> SEQUENCE: 19

Met Arg Leu Arg Asn Gly Thr Val Ala Thr Ala Leu Val Phe Val Thr
1               5                   10                  15

Ser Phe Leu Thr Leu Ser Trp Tyr Thr Thr Trp Gln Asn Gly Lys Glu
            20                  25                  30

Lys Leu Ile Ala Tyr Gln Arg Glu Phe Leu Ala Leu Lys Glu Arg Leu
        35                  40                  45

Arg Val Ala Glu His Arg Ile Ser Gln Arg Ser Ser Glu Leu Asn Thr
50                  55                  60
```

```
Ile Val Gln Gln Phe Arg Arg Ala Gly Ala Glu Thr Asn Gly Ser Lys
 65                  70                  75                  80

Thr Ala Leu Ser Thr Ile Ser Asp Asn Thr Ile Lys Leu Leu Lys Glu
                 85                  90                  95

Leu Thr Ser Lys Lys Ser Leu Arg Val Pro Ser Ile Tyr Tyr His Leu
            100                 105                 110

Pro His Leu Leu Gln Asn Glu Arg Ser Leu Gln Pro Ala Val Gln Ile
        115                 120                 125

Gly Ser Gly Arg Thr Gly Val Ser Ile Val Met Gly Ile Pro Thr Val
    130                 135                 140

Lys Arg Glu Val Lys Ser Tyr Leu Val Glu Thr Leu His Ser Leu Ile
145                 150                 155                 160

Asp Asn Leu Tyr Pro Glu Glu Lys Leu Asp Cys Val Ile Val Val Phe
                165                 170                 175

Ile Gly Glu Thr Asp Leu Asp Tyr Val His Ser Val Val Ala Asn Leu
            180                 185                 190

Glu Lys Glu Phe Ser Arg Glu Ile Ser Ser Gly Leu Leu Glu Ile Ile
        195                 200                 205

Ser Pro Pro Glu Ser Tyr Tyr Pro Asp Leu Thr Asn Leu Lys Glu Thr
210                 215                 220

Phe Gly Asp Ser Lys Glu Arg Val Arg Trp Arg Thr Lys Gln Asn Leu
225                 230                 235                 240

Asp Tyr Cys Phe Leu Met Met Tyr Ala Gln Glu Lys Gly Ile Tyr Tyr
                245                 250                 255

Ile Gln Leu Glu Asp Asp Ile Ile Val Lys Gln Asn Tyr Phe Asn Thr
            260                 265                 270

Ile Lys Asn Phe Ala Leu Gln Leu Ser Ser Glu Glu Trp Met Ile Leu
        275                 280                 285

Glu Phe Ser Gln Leu Gly Phe Ile Gly Lys Met Phe Gln Ala Pro Asp
290                 295                 300

Leu Ala Leu Val Val Glu Phe Ile Leu Met Phe Tyr Lys Glu Lys Pro
305                 310                 315                 320

Ile Asp Trp Leu Leu Asp His Ile Leu Trp Val Lys Val Cys Asn Pro
                325                 330                 335

Glu Lys Asp Ala Lys His Cys Asp Arg Gln Lys Ala Asn Leu Arg Ile
            340                 345                 350

Arg Phe Arg Pro Ser Leu Phe Gln His Val Gly Leu His Ser Ser Leu
        355                 360                 365

Ser Gly Lys Ile Gln Lys Leu Thr Asp Lys Asp Tyr Met Lys Pro Leu
370                 375                 380

Leu Leu Lys Val His Val Asn Pro Pro Ala Glu Val Ser Thr Ser Leu
385                 390                 395                 400

Lys Val Tyr Gln Gly His Thr Leu Glu Lys Thr Tyr Met Gly Glu Asp
                405                 410                 415

Phe Phe Trp Ala Ile Thr Pro Thr Ala Gly Asp Tyr Ile Leu Phe Lys
            420                 425                 430

Phe Asp Lys Pro Val Asn Val Glu Ser Tyr Leu Phe His Ser Gly Asn
        435                 440                 445

Gln Glu His Pro Gly Asp Ile Leu Leu Asn Thr Thr Val Asp Val Leu
450                 455                 460

Pro Leu Lys Ser Asp Ser Leu Glu Ile Ser Lys Glu Thr Lys Asp Lys
465                 470                 475                 480
```

```
Arg Leu Glu Asp Gly Tyr Phe Arg Ile Gly Lys Phe Glu Tyr Gly Val
                485                 490                 495

Ala Glu Gly Ile Val Asp Pro Gly Leu Asn Pro Ile Ser Ala Phe Arg
            500                 505                 510

Leu Ser Val Ile Gln Asn Ser Ala Val Trp Ala Ile Leu Asn Glu Ile
        515                 520                 525

His Ile Lys Lys Val Thr Ser
    530                 535

<210> SEQ ID NO 20
<211> LENGTH: 548
<212> TYPE: PRT
<213> ORGANISM: Mus musculus

<400> SEQUENCE: 20

Met Arg Leu Arg Asn Gly Thr Phe Leu Thr Leu Leu Leu Phe Cys Leu
1               5                   10                  15

Cys Ala Phe Leu Ser Leu Ser Trp Tyr Ala Ala Leu Ser Gly Gln Lys
            20                  25                  30

Gly Asp Val Val Asp Ile Tyr Gln Arg Glu Phe Leu Ala Leu Arg Asp
        35                  40                  45

Arg Leu His Ala Ala Glu Gln Glu Ser Leu Lys Arg Ser Lys Glu Leu
    50                  55                  60

Asn Leu Val Leu Glu Glu Ile Lys Arg Ala Val Ser Glu Arg Gln Ala
65                  70                  75                  80

Leu Arg Asp Gly Glu Gly Asn Arg Thr Trp Gly Arg Leu Thr Glu Asp
                85                  90                  95

Pro Arg Leu Lys Pro Trp Asn Val Ser His Arg His Val Leu His Leu
            100                 105                 110

Pro Thr Val Phe His His Leu Pro His Leu Leu Ala Lys Glu Ser Ser
        115                 120                 125

Leu Gln Pro Ala Arg Val Gly Gln Gly Arg Thr Gly Val Ser Val
    130                 135                 140

Val Met Gly Ile Pro Ser Val Arg Arg Glu Val His Ser Tyr Leu Thr
145                 150                 155                 160

Asp Thr Leu His Ser Leu Ile Ser Glu Leu Ser Pro Gln Glu Lys Glu
                165                 170                 175

Asp Ser Val Ile Val Leu Ile Ala Glu Thr Asp Pro Gln Tyr Thr
            180                 185                 190

Ser Ala Val Thr Glu Asn Ile Lys Ala Leu Phe Pro Thr Glu Ile His
        195                 200                 205

Ser Gly Leu Leu Glu Val Ile Ser Pro Ser Pro His Phe Tyr Pro Asp
    210                 215                 220

Phe Ser Arg Leu Arg Glu Ser Phe Gly Asp Pro Lys Glu Arg Val Arg
225                 230                 235                 240

Trp Arg Thr Lys Gln Asn Leu Asp Tyr Cys Phe Leu Met Met Tyr Ala
                245                 250                 255

Gln Ser Lys Gly Ile Tyr Tyr Val Gln Leu Glu Asp Asp Ile Val Ala
            260                 265                 270

Lys Pro Asn Tyr Leu Ser Thr Met Lys Asn Phe Ala Leu Gln Gln Pro
        275                 280                 285

Ser Glu Asp Trp Met Ile Leu Glu Phe Ser Leu Gly Phe Ile Gly
    290                 295                 300

Lys Met Phe Lys Ser Leu Asp Leu Ser Leu Ile Val Glu Phe Ile Leu
305                 310                 315                 320
```

```
Met Phe Tyr Arg Asp Lys Pro Ile Asp Trp Leu Leu Asp His Ile Leu
            325                 330                 335

Trp Val Lys Val Cys Asn Pro Glu Lys Asp Ala Lys His Cys Asp Arg
        340                 345                 350

Gln Lys Ala Asn Leu Arg Ile Arg Phe Lys Pro Ser Leu Phe Gln His
            355                 360                 365

Val Gly Thr His Ser Ser Leu Ala Gly Lys Ile Gln Lys Leu Lys Asp
    370                 375                 380

Lys Asp Phe Gly Lys His Ala Leu Arg Lys Glu His Val Asn Pro Pro
385                 390                 395                 400

Ala Glu Val Ser Thr Ser Leu Lys Thr Tyr Gln His Phe Thr Leu Glu
                405                 410                 415

Lys Ala Tyr Leu Arg Glu Asp Phe Phe Trp Ala Phe Thr Pro Ala Ala
            420                 425                 430

Gly Asp Phe Ile Arg Phe Arg Phe Gln Pro Leu Arg Leu Glu Arg
        435                 440                 445

Phe Phe Phe Arg Ser Gly Asn Ile Glu His Pro Glu Asp Lys Leu Phe
    450                 455                 460

Asn Thr Ser Val Glu Val Leu Pro Phe Asp Asn Pro Gln Ser Glu Lys
465                 470                 475                 480

Glu Ala Leu Gln Glu Gly Arg Ser Ala Thr Leu Arg Tyr Pro Arg Ser
                485                 490                 495

Pro Asp Gly Tyr Leu Gln Ile Gly Ser Phe Tyr Lys Gly Val Ala Glu
            500                 505                 510

Gly Glu Val Asp Pro Ala Phe Gly Pro Leu Ala Leu Arg Leu Ser
        515                 520                 525

Ile Gln Thr Asp Ser Pro Val Trp Val Ile Leu Ser Glu Ile Phe Leu
    530                 535                 540

Lys Lys Ala Asp
545

<210> SEQ ID NO 21
<211> LENGTH: 478
<212> TYPE: PRT
<213> ORGANISM: Mus musculus

<400> SEQUENCE: 21

Met Leu Lys Phe Tyr Gln Met Lys Tyr Ile Phe Gln Ile Leu Asp Lys
1               5                   10                  15

Met Arg Cys Leu Arg Lys Arg Ser Thr Val Ser Phe Leu Gly Val Leu
            20                  25                  30

Val Val Phe Leu Leu Phe Met Asn Leu Tyr Ile Glu Asp Ser Tyr Val
        35                  40                  45

Leu Glu Gly Asp Lys Gln Leu Ile Arg Glu Thr Ser Thr His Gln Leu
    50                  55                  60

Asn Ser Glu Arg Tyr Val His Thr Phe Lys Asp Leu Ser Asn Phe Ser
65                  70                  75                  80

Gly Thr Ile Asn Val Thr Tyr Arg Tyr Leu Ala Ala Thr Pro Leu Gln
                85                  90                  95

Arg Lys Arg Tyr Leu Thr Ile Gly Leu Ser Ser Val Lys Arg Lys Lys
            100                 105                 110

Gly Asn Tyr Leu Leu Asp Thr Ile Lys Ser Ile Phe Glu Gln Ser Ser
        115                 120                 125

Tyr Glu Glu Leu Lys Glu Ile Ser Val Val Val His Leu Ala Asp Phe
```

```
                130                 135                 140
Asn Ser Ser Trp Arg Asp Ala Met Val Gln Asp Ile Thr Gln Lys Phe
145                 150                 155                 160

Ala His His Ile Ile Ala Gly Arg Leu Met Val Ile His Ala Pro Glu
                165                 170                 175

Glu Tyr Tyr Pro Val Leu Asp Gly Leu Lys Arg Asn Tyr Asn Asp Pro
                180                 185                 190

Glu Asp Arg Val Arg Phe Arg Ser Lys Gln Asn Val Asp Tyr Ala Phe
                195                 200                 205

Leu Leu Asn Phe Cys Ala Asn Thr Ser Asp Tyr Tyr Val Met Leu Glu
                210                 215                 220

Asp Asp Val Arg Cys Ser Arg Asn Phe Leu Thr Ala Ile Lys Lys Val
225                 230                 235                 240

Ile Ala Ser Leu Glu Gly Thr Tyr Trp Val Thr Leu Glu Phe Ser Lys
                245                 250                 255

Leu Gly Tyr Ile Gly Lys Leu Tyr His Ser His Asp Leu Pro Arg Leu
                260                 265                 270

Ala His Phe Leu Leu Met Phe Tyr Gln Glu Met Pro Cys Asp Trp Leu
                275                 280                 285

Leu Thr His Phe Arg Gly Leu Leu Ala Gln Lys Asn Val Ile Arg Phe
                290                 295                 300

Lys Pro Ser Leu Phe Gln His Met Gly Tyr Tyr Ser Ser Tyr Lys Gly
305                 310                 315                 320

Thr Glu Asn Lys Leu Lys Asp Asp Phe Glu Glu Ser Phe Asp
                325                 330                 335

Ile Pro Asp Asn Pro Pro Ala Ser Phe Tyr Thr Asn Met Asn Val Phe
                340                 345                 350

Glu Asn Tyr Glu Ala Ser Lys Ala Tyr Ser Ser Val Asp Glu Tyr Phe
                355                 360                 365

Trp Gly Lys Ser Pro Ser Met Gly Asp Thr Phe Val Ile Val Phe Glu
                370                 375                 380

Asn Pro Ile Thr Ile Lys Lys Ile Lys Val Asn Thr Gly Thr Glu Asp
385                 390                 395                 400

Arg Gln Asn Asp Ile Leu Gln His Gly Ala Leu Asp Val Gly Glu Lys
                405                 410                 415

Leu Ile Phe Ser Lys Gln Ile Arg Gln Cys Asp Thr Tyr Leu Arg Leu
                420                 425                 430

Gly Glu Phe Lys Asn Gly Tyr Phe Glu Met Ser Asp Val Asn Gln Lys
                435                 440                 445

Ile Pro Phe Asp Ile His Cys Met Arg Ile Cys Val Thr Lys Thr Gln
                450                 455                 460

Lys Glu Trp Leu Ile Ile Arg Ser Ile Ser Ile Trp Thr Ser
465                 470                 475

<210> SEQ ID NO 22
<211> LENGTH: 535
<212> TYPE: PRT
<213> ORGANISM: Homo sapiens

<400> SEQUENCE: 22

Met Arg Leu Arg Asn Gly Thr Val Ala Thr Ala Leu Ala Phe Ile Thr
1               5                   10                  15

Ser Phe Leu Thr Leu Ser Trp Tyr Thr Thr Trp Gln Asn Gly Lys Glu
                20                  25                  30
```

-continued

```
Lys Leu Ile Ala Tyr Gln Arg Glu Phe Leu Ala Leu Lys Glu Arg Leu
             35                  40                  45

Arg Ile Ala Glu His Arg Ile Ser Gln Arg Ser Ser Glu Leu Asn Thr
 50                  55                  60

Ile Val Gln Gln Phe Lys Arg Val Gly Ala Glu Thr Asn Gly Ser Lys
 65                  70                  75                  80

Asp Ala Leu Asn Lys Phe Ser Asp Asn Thr Leu Lys Leu Leu Lys Glu
                 85                  90                  95

Leu Thr Ser Lys Lys Ser Leu Gln Val Pro Ser Ile Tyr Tyr His Leu
            100                 105                 110

Pro His Leu Leu Lys Asn Glu Gly Ser Leu Gln Pro Ala Val Gln Ile
            115                 120                 125

Gly Asn Gly Arg Thr Gly Val Ser Ile Val Met Gly Ile Pro Thr Val
130                 135                 140

Lys Arg Glu Val Lys Ser Tyr Leu Ile Glu Thr Leu His Ser Leu Ile
145                 150                 155                 160

Asp Asn Leu Tyr Pro Glu Glu Lys Leu Asp Cys Val Ile Val Val Phe
                165                 170                 175

Ile Gly Glu Thr Asp Ile Asp Tyr Val His Gly Val Val Ala Asn Leu
            180                 185                 190

Glu Lys Glu Phe Ser Lys Glu Ile Ser Ser Gly Leu Val Glu Val Ile
        195                 200                 205

Ser Pro Pro Glu Ser Tyr Tyr Pro Asp Leu Thr Asn Leu Lys Glu Thr
    210                 215                 220

Phe Gly Asp Ser Lys Glu Arg Val Arg Trp Arg Thr Lys Gln Asn Leu
225                 230                 235                 240

Asp Tyr Cys Phe Leu Met Met Tyr Ala Gln Glu Lys Gly Ile Tyr Tyr
                245                 250                 255

Ile Gln Leu Glu Asp Asp Ile Ile Val Lys Gln Asn Tyr Phe Asn Thr
            260                 265                 270

Ile Lys Asn Phe Ala Leu Gln Leu Ser Ser Glu Glu Trp Met Ile Leu
        275                 280                 285

Glu Phe Ser Gln Leu Gly Phe Ile Gly Lys Met Phe Gln Ala Pro Asp
    290                 295                 300

Leu Thr Leu Ile Val Glu Phe Ile Phe Met Phe Tyr Lys Glu Lys Pro
305                 310                 315                 320

Ile Asp Trp Leu Leu Asp His Ile Leu Trp Val Lys Val Cys Asn Pro
                325                 330                 335

Glu Lys Asp Ala Lys His Cys Asp Arg Gln Lys Ala Asn Leu Arg Ile
            340                 345                 350

Arg Phe Arg Pro Ser Leu Phe Gln His Val Gly Leu His Ser Ser Leu
        355                 360                 365

Ser Gly Lys Ile Gln Lys Leu Thr Asp Lys Tyr Met Lys Pro Leu
    370                 375                 380

Leu Leu Lys Ile His Val Asn Pro Pro Ala Glu Val Ser Thr Ser Leu
385                 390                 395                 400

Lys Val Tyr Gln Gly His Thr Leu Glu Lys Thr Tyr Met Gly Glu Asp
                405                 410                 415

Phe Phe Trp Ala Ile Thr Pro Ile Ala Gly Asp Tyr Ile Leu Phe Lys
            420                 425                 430

Phe Asp Lys Pro Val Asn Val Glu Ser Tyr Leu Phe His Ser Gly Asn
        435                 440                 445

Gln Glu His Pro Gly Asp Ile Leu Leu Asn Thr Thr Val Glu Val Leu
```

```
                450              455              460
Pro Phe Lys Ser Glu Gly Leu Glu Ile Ser Lys Glu Thr Lys Asp Lys
465                 470                 475                 480

Arg Leu Glu Asp Gly Tyr Phe Arg Ile Gly Lys Phe Glu Asn Gly Val
                485                 490                 495

Ala Glu Gly Met Val Asp Pro Ser Leu Asn Pro Ile Ser Ala Phe Arg
                500                 505                 510

Leu Ser Val Ile Gln Asn Ser Ala Val Trp Ala Ile Leu Asn Glu Ile
            515                 520                 525

His Ile Lys Lys Ala Thr Asn
            530                 535

<210> SEQ ID NO 23
<211> LENGTH: 548
<212> TYPE: PRT
<213> ORGANISM: Homo sapiens

<400> SEQUENCE: 23

Met Arg Leu Arg Asn Gly Thr Phe Leu Thr Leu Leu Leu Phe Cys Leu
1               5                   10                  15

Cys Ala Phe Leu Ser Leu Ser Trp Tyr Ala Ala Leu Ser Gly Gln Lys
                20                  25                  30

Gly Asp Val Val Asp Val Tyr Gln Arg Glu Phe Leu Ala Leu Arg Asp
            35                  40                  45

Arg Leu His Ala Ala Glu Gln Glu Ser Leu Lys Arg Ser Lys Glu Leu
50                  55                  60

Asn Leu Val Leu Asp Glu Ile Lys Arg Ala Val Ser Glu Arg Gln Ala
65                  70                  75                  80

Leu Arg Asp Gly Asp Gly Asn Arg Thr Trp Gly Arg Leu Thr Glu Asp
                85                  90                  95

Pro Arg Leu Lys Pro Trp Asn Gly Ser His Arg His Val Leu His Leu
            100                 105                 110

Pro Thr Val Phe His His Leu Pro His Leu Leu Ala Lys Glu Ser Ser
            115                 120                 125

Leu Gln Pro Ala Val Arg Val Gly Gln Gly Arg Thr Gly Val Ser Val
        130                 135                 140

Val Met Gly Ile Pro Ser Val Arg Arg Glu Val His Ser Tyr Leu Thr
145                 150                 155                 160

Asp Thr Leu His Ser Leu Ile Ser Glu Leu Ser Pro Gln Glu Lys Glu
                165                 170                 175

Asp Ser Val Ile Val Val Leu Ile Ala Glu Thr Asp Ser Gln Tyr Thr
            180                 185                 190

Ser Ala Val Thr Glu Asn Ile Lys Ala Leu Phe Pro Thr Glu Ile His
        195                 200                 205

Ser Gly Leu Leu Glu Val Ile Ser Pro Ser Pro His Phe Tyr Pro Asp
    210                 215                 220

Phe Ser Arg Leu Arg Glu Ser Phe Gly Asp Pro Lys Glu Arg Val Arg
225                 230                 235                 240

Trp Arg Thr Lys Gln Asn Leu Asp Tyr Cys Phe Leu Met Met Tyr Ala
                245                 250                 255

Gln Ser Lys Gly Ile Tyr Tyr Val Gln Leu Glu Asp Asp Ile Val Ala
            260                 265                 270

Lys Pro Asn Tyr Leu Ser Thr Met Lys Asn Phe Ala Leu Gln Gln Pro
        275                 280                 285
```

```
Ser Glu Asp Trp Met Ile Leu Glu Phe Ser Gln Leu Gly Phe Ile Gly
    290                 295                 300

Lys Met Phe Lys Ser Leu Asp Leu Ser Leu Ile Val Glu Phe Ile Leu
305                 310                 315                 320

Met Phe Tyr Arg Asp Lys Pro Ile Asp Trp Leu Leu Asp His Ile Leu
                325                 330                 335

Trp Val Lys Val Cys Asn Pro Glu Lys Asp Ala Lys His Cys Asp Arg
            340                 345                 350

Gln Lys Ala Asn Leu Arg Ile Arg Phe Lys Pro Ser Leu Phe Gln His
        355                 360                 365

Val Gly Thr His Ser Ser Leu Ala Gly Lys Ile Gln Lys Leu Lys Asp
    370                 375                 380

Lys Asp Phe Gly Lys Gln Ala Leu Arg Lys Glu His Val Asn Pro Pro
385                 390                 395                 400

Ala Glu Val Ser Thr Ser Leu Lys Thr Tyr Gln His Phe Thr Leu Glu
                405                 410                 415

Lys Ala Tyr Leu Arg Glu Asp Phe Phe Trp Ala Phe Thr Pro Ala Ala
            420                 425                 430

Gly Asp Phe Ile Arg Phe Arg Phe Gln Pro Leu Arg Leu Glu Arg
        435                 440                 445

Phe Phe Phe Arg Ser Gly Asn Ile Glu His Pro Glu Asp Lys Leu Phe
    450                 455                 460

Asn Thr Ser Val Glu Val Leu Pro Phe Asp Asn Pro Gln Ser Asp Lys
465                 470                 475                 480

Glu Ala Leu Gln Glu Gly Arg Thr Ala Thr Leu Arg Tyr Pro Arg Ser
                485                 490                 495

Pro Asp Gly Tyr Leu Gln Ile Gly Ser Phe Tyr Lys Gly Val Ala Glu
            500                 505                 510

Gly Glu Val Asp Pro Ala Phe Gly Pro Leu Glu Ala Leu Arg Leu Ser
        515                 520                 525

Ile Gln Thr Asp Ser Pro Val Trp Val Ile Leu Ser Glu Ile Phe Leu
    530                 535                 540

Lys Lys Ala Asp
545

<210> SEQ ID NO 24
<211> LENGTH: 563
<212> TYPE: PRT
<213> ORGANISM: Homo sapiens

<400> SEQUENCE: 24

Met Ser Arg Val Ala Gly Thr Arg Thr Asp Val Asn Glu Leu Leu Gln
1               5                   10                  15

Arg Trp Thr Pro Arg Cys Val Arg Trp His Thr Gly Gly Ala Arg Arg
                20                  25                  30

Val Ala Leu Asp Arg Pro Leu Val Thr Ala Cys Leu Pro Pro Ala Gly
            35                  40                  45

Asp Val Val Asp Val Tyr Gln Arg Glu Phe Leu Ala Leu Arg Asp Arg
        50                  55                  60

Leu His Ala Ala Glu Gln Glu Ser Leu Lys Arg Ser Lys Glu Leu Asn
65                  70                  75                  80

Leu Val Leu Asp Glu Ile Lys Arg Ala Val Ser Glu Arg Gln Ala Leu
                85                  90                  95

Arg Asp Gly Asp Gly Asn Arg Thr Trp Gly Arg Leu Thr Glu Asp Pro
            100                 105                 110
```

```
Arg Leu Lys Pro Trp Asn Gly Ser His Arg His Val Leu His Leu Pro
            115                 120                 125
Thr Val Phe His His Leu Pro His Leu Leu Ala Lys Glu Ser Ser Leu
        130                 135                 140
Gln Pro Ala Val Arg Val Gly Gln Gly Arg Thr Gly Val Ser Val Val
145                 150                 155                 160
Met Gly Ile Pro Ser Val Arg Arg Glu Val His Ser Tyr Leu Thr Asp
                165                 170                 175
Thr Leu His Ser Leu Ile Ser Glu Leu Ser Pro Gln Glu Lys Glu Asp
            180                 185                 190
Ser Val Ile Val Val Leu Ile Ala Glu Thr Asp Ser Gln Tyr Thr Ser
                195                 200                 205
Ala Val Thr Glu Asn Ile Lys Ala Leu Phe Pro Thr Glu Ile His Ser
        210                 215                 220
Gly Leu Leu Glu Val Ile Ser Pro Ser Pro His Phe Tyr Pro Asp Phe
225                 230                 235                 240
Ser Arg Leu Arg Glu Ser Phe Gly Asp Pro Lys Glu Arg Val Arg Trp
                245                 250                 255
Arg Thr Lys Gln Asn Leu Asp Tyr Cys Phe Leu Met Met Tyr Ala Gln
            260                 265                 270
Ser Lys Gly Ile Tyr Tyr Val Gln Leu Glu Asp Asp Ile Val Ala Lys
        275                 280                 285
Pro Asn Tyr Leu Ser Thr Met Lys Asn Phe Ala Leu Gln Gln Pro Ser
        290                 295                 300
Glu Asp Trp Met Ile Leu Glu Phe Ser Gln Leu Gly Phe Ile Gly Lys
305                 310                 315                 320
Met Phe Lys Ser Leu Asp Leu Ser Leu Ile Val Glu Phe Ile Leu Met
                325                 330                 335
Phe Tyr Arg Asp Lys Pro Ile Asp Trp Leu Leu Asp His Ile Leu Trp
                340                 345                 350
Val Lys Val Cys Asn Pro Glu Lys Asp Ala Lys His Cys Asp Arg Gln
        355                 360                 365
Lys Ala Asn Leu Arg Ile Arg Phe Lys Pro Ser Leu Phe Gln His Val
        370                 375                 380
Gly Thr His Ser Ser Leu Ala Gly Lys Ile Gln Lys Leu Lys Asp Lys
385                 390                 395                 400
Asp Phe Gly Lys Gln Ala Leu Arg Lys Glu His Val Asn Pro Pro Ala
                405                 410                 415
Glu Val Ser Thr Ser Leu Lys Thr Tyr Gln His Phe Thr Leu Glu Lys
                420                 425                 430
Ala Tyr Leu Arg Glu Asp Phe Phe Trp Ala Phe Thr Pro Ala Ala Gly
            435                 440                 445
Asp Phe Ile Arg Phe Arg Phe Gln Pro Leu Arg Leu Glu Arg Phe
        450                 455                 460
Phe Phe Arg Ser Gly Asn Ile Glu His Pro Glu Asp Lys Leu Phe Asn
465                 470                 475                 480
Thr Ser Val Glu Val Leu Pro Phe Asp Asn Pro Gln Ser Asp Lys Glu
                485                 490                 495
Ala Leu Gln Glu Gly Arg Thr Ala Thr Leu Arg Tyr Pro Arg Ser Pro
                500                 505                 510
Asp Gly Tyr Leu Gln Ile Gly Ser Phe Tyr Lys Gly Val Ala Glu Gly
            515                 520                 525
```

-continued

Glu Val Asp Pro Ala Phe Gly Pro Leu Glu Ala Leu Arg Leu Ser Ile
        530                 535                 540

Gln Thr Asp Ser Pro Val Trp Val Ile Leu Ser Glu Ile Phe Leu Lys
545                 550                 555                 560

Lys Ala Asp

<210> SEQ ID NO 25
<211> LENGTH: 478
<212> TYPE: PRT
<213> ORGANISM: Homo sapiens

<400> SEQUENCE: 25

Met Phe Lys Phe His Gln Met Lys His Ile Phe Glu Ile Leu Asp Lys
1               5                   10                  15

Met Arg Cys Leu Arg Lys Arg Ser Thr Val Ser Phe Leu Gly Val Leu
            20                  25                  30

Val Ile Phe Leu Leu Phe Met Asn Leu Tyr Ile Glu Asp Ser Tyr Val
        35                  40                  45

Leu Glu Gly Asp Lys Gln Leu Ile Arg Glu Thr Ser Thr His Gln Leu
    50                  55                  60

Asn Ser Glu Arg Tyr Val His Thr Phe Lys Asp Leu Ser Asn Phe Ser
65                  70                  75                  80

Gly Ala Ile Asn Val Thr Tyr Arg Tyr Leu Ala Ala Thr Pro Leu Gln
                85                  90                  95

Arg Lys Arg Tyr Leu Thr Ile Gly Leu Ser Ser Val Lys Arg Lys Lys
            100                 105                 110

Gly Asn Tyr Leu Leu Glu Thr Ile Lys Ser Ile Phe Glu Gln Ser Ser
        115                 120                 125

Tyr Glu Glu Leu Lys Glu Ile Ser Val Val His Leu Ala Asp Phe
    130                 135                 140

Asn Ser Ser Trp Arg Asp Ala Met Val Gln Ile Thr Gln Lys Phe
145                 150                 155                 160

Ala His His Ile Ile Ala Gly Arg Leu Met Val Ile His Ala Pro Glu
                165                 170                 175

Glu Tyr Tyr Pro Ile Leu Asp Gly Leu Lys Arg Asn Tyr Asn Asp Pro
            180                 185                 190

Glu Asp Arg Val Lys Phe Arg Ser Lys Gln Asn Val Asp Tyr Ala Phe
        195                 200                 205

Leu Leu Asn Phe Cys Ala Asn Thr Ser Asp Tyr Tyr Val Met Leu Glu
    210                 215                 220

Asp Asp Val Arg Cys Ser Lys Asn Phe Leu Thr Ala Ile Lys Lys Val
225                 230                 235                 240

Ile Ala Ser Leu Glu Gly Thr Tyr Trp Val Thr Leu Glu Phe Ser Lys
                245                 250                 255

Leu Gly Tyr Ile Gly Lys Leu Tyr His Ser His Asp Leu Pro Arg Leu
            260                 265                 270

Ala His Phe Leu Leu Met Phe Tyr Gln Glu Met Pro Cys Asp Trp Leu
        275                 280                 285

Leu Thr His Phe Arg Gly Leu Leu Ala Gln Lys Asn Val Ile Arg Phe
    290                 295                 300

Lys Pro Ser Leu Phe Gln His Met Gly Tyr Tyr Ser Ser Tyr Lys Gly
305                 310                 315                 320

Thr Glu Asn Lys Leu Lys Asp Asp Phe Glu Glu Glu Ser Phe Asp
                325                 330                 335

```
Ile Pro Asp Asn Pro Pro Ala Ser Leu Tyr Thr Asn Met Asn Val Phe
            340                 345                 350

Glu Asn Tyr Glu Ala Ser Lys Ala Tyr Ser Ser Val Asp Glu Tyr Phe
        355                 360                 365

Trp Gly Lys Pro Pro Ser Thr Gly Asp Val Phe Val Ile Val Phe Glu
    370                 375                 380

Asn Pro Ile Ile Ile Lys Lys Ile Lys Val Asn Thr Gly Thr Glu Asp
385                 390                 395                 400

Arg Gln Asn Asp Ile Leu His His Gly Ala Leu Asp Val Gly Glu Asn
                405                 410                 415

Val Met Pro Ser Lys Gln Arg Arg Gln Cys Ser Thr Tyr Leu Arg Leu
            420                 425                 430

Gly Glu Phe Lys Asn Gly Asn Phe Glu Met Ser Gly Val Asn Gln Lys
        435                 440                 445

Ile Pro Phe Asp Ile His Cys Met Arg Ile Tyr Val Thr Lys Thr Gln
    450                 455                 460

Lys Glu Trp Leu Ile Ile Arg Ser Ile Ser Ile Trp Thr Ser
465                 470                 475

<210> SEQ ID NO 26
<211> LENGTH: 740
<212> TYPE: PRT
<213> ORGANISM: Mus musculus

<400> SEQUENCE: 26

Met Ala Phe Phe Ser Pro Trp Lys Leu Ser Gln Lys Leu Gly Phe
1               5                   10                  15

Phe Leu Val Thr Phe Gly Phe Ile Trp Gly Met Met Leu Leu His Phe
                20                  25                  30

Thr Ile Gln Gln Arg Thr Gln Pro Glu Ser Ser Ser Met Leu Arg Glu
            35                  40                  45

Gln Ile Leu Asp Leu Ser Lys Arg Tyr Ile Lys Ala Leu Ala Glu Glu
        50                  55                  60

Asn Arg Asp Val Val Asp Gly Pro Tyr Ala Gly Val Met Thr Ala Tyr
65                  70                  75                  80

Asp Leu Lys Lys Thr Leu Ala Val Leu Leu Asp Asn Ile Leu Gln Arg
                85                  90                  95

Ile Gly Lys Leu Glu Ser Lys Val Asp Asn Leu Val Asn Gly Thr Gly
                100                 105                 110

Ala Asn Ser Thr Asn Ser Thr Thr Ala Val Pro Ser Leu Val Ser Leu
            115                 120                 125

Glu Lys Ile Asn Val Ala Asp Ile Ile Asn Gly Val Gln Glu Lys Cys
        130                 135                 140

Val Leu Pro Pro Met Asp Gly Tyr Pro His Cys Glu Gly Lys Ile Lys
145                 150                 155                 160

Trp Met Lys Asp Met Trp Arg Ser Asp Pro Cys Tyr Ala Asp Tyr Gly
                165                 170                 175

Val Asp Gly Thr Ser Cys Ser Phe Phe Ile Tyr Leu Ser Glu Val Glu
                180                 185                 190

Asn Trp Cys Pro Arg Leu Pro Trp Arg Ala Lys Asn Pro Tyr Glu Glu
            195                 200                 205

Ala Asp His Asn Ser Leu Ala Glu Ile Arg Thr Asp Phe Asn Ile Leu
        210                 215                 220

Tyr Gly Met Met Lys Lys His Glu Glu Phe Arg Trp Met Arg Leu Arg
225                 230                 235                 240
```

```
Ile Arg Arg Met Ala Asp Ala Trp Ile Gln Ala Ile Lys Ser Leu Ala
            245                 250                 255

Glu Lys Gln Asn Leu Glu Lys Arg Arg Lys Lys Ile Leu Val His
            260                 265                 270

Leu Gly Leu Leu Thr Lys Glu Ser Gly Phe Lys Ile Ala Glu Thr Ala
            275                 280                 285

Phe Ser Gly Gly Pro Leu Gly Glu Leu Val Gln Trp Ser Asp Leu Ile
290                         295                 300

Thr Ser Leu Tyr Leu Leu Gly His Asp Ile Arg Ile Ser Ala Ser Leu
305                 310                 315                 320

Ala Glu Leu Lys Glu Ile Met Lys Lys Val Val Gly Asn Arg Ser Gly
                325                 330                 335

Cys Pro Thr Val Gly Asp Arg Ile Val Glu Leu Ile Tyr Ile Asp Ile
            340                 345                 350

Val Gly Leu Ala Gln Phe Lys Lys Thr Leu Gly Pro Ser Trp Val His
            355                 360                 365

Tyr Gln Cys Met Leu Arg Val Leu Asp Ser Phe Gly Thr Glu Pro Glu
            370                 375                 380

Phe Asn His Ala Ser Tyr Ala Gln Ser Lys Gly His Lys Thr Pro Trp
385                 390                 395                 400

Gly Lys Trp Asn Leu Asn Pro Gln Gln Phe Tyr Thr Met Phe Pro His
                405                 410                 415

Thr Pro Asp Asn Ser Phe Leu Gly Phe Val Val Glu Gln His Leu Asn
            420                 425                 430

Ser Ser Asp Ile His His Ile Asn Glu Ile Lys Arg Gln Asn Gln Ser
            435                 440                 445

Leu Val Tyr Gly Lys Val Asp Ser Phe Trp Lys Asn Lys Lys Ile Tyr
            450                 455                 460

Leu Asp Ile Ile His Thr Tyr Met Glu Val His Ala Thr Val Tyr Gly
465                 470                 475                 480

Ser Ser Thr Lys Asn Ile Pro Ser Tyr Val Lys Asn His Gly Ile Leu
            485                 490                 495

Ser Gly Arg Asp Leu Gln Phe Leu Leu Arg Glu Thr Lys Leu Phe Val
            500                 505                 510

Gly Leu Gly Phe Pro Tyr Glu Gly Pro Ala Pro Leu Glu Ala Ile Ala
            515                 520                 525

Asn Gly Cys Ala Phe Leu Asn Pro Lys Phe Asn Pro Pro Lys Ser Ser
            530                 535                 540

Lys Asn Thr Asp Phe Phe Ile Gly Lys Pro Thr Leu Arg Glu Leu Thr
545                 550                 555                 560

Ser Gln His Pro Tyr Ala Glu Val Phe Ile Gly Arg Pro His Val Trp
            565                 570                 575

Thr Val Asp Leu Asn Asn Arg Glu Glu Val Glu Asp Ala Val Lys Ala
            580                 585                 590

Ile Leu Asn Gln Lys Ile Glu Pro Tyr Met Pro Tyr Glu Phe Thr Cys
            595                 600                 605

Glu Gly Met Leu Gln Arg Ile Asn Ala Phe Ile Glu Lys Gln Asp Phe
            610                 615                 620

Cys His Gly Gln Val Met Trp Pro Pro Leu Ser Ala Leu Gln Val Lys
625                 630                 635                 640

Leu Ala Glu Pro Gly Gln Ser Cys Lys Gln Val Cys Gln Glu Ser Gln
            645                 650                 655
```

```
Leu Ile Cys Glu Pro Ser Phe Phe Gln His Leu Asn Lys Glu Lys Asp
            660                 665                 670

Leu Leu Lys Tyr Lys Val Thr Cys Gln Ser Ser Glu Leu Tyr Lys Asp
        675                 680                 685

Ile Leu Val Pro Ser Phe Tyr Pro Lys Ser Lys His Cys Val Phe Gln
    690                 695                 700

Gly Asp Leu Leu Phe Ser Cys Ala Gly Ala His Pro Thr His Gln
705                 710                 715                 720

Arg Ile Cys Pro Cys Arg Asp Phe Ile Lys Gly Gln Val Ala Leu Cys
                725                 730                 735

Lys Asp Cys Leu
            740

<210> SEQ ID NO 27
<211> LENGTH: 792
<212> TYPE: PRT
<213> ORGANISM: Mus musculus

<400> SEQUENCE: 27

Met Ile Thr Val Asn Pro Asp Gly Lys Ile Met Val Arg Arg Cys Leu
1               5                   10                  15

Val Thr Leu Arg Pro Phe Arg Leu Phe Val Leu Gly Ile Gly Phe Phe
            20                  25                  30

Thr Leu Cys Phe Leu Met Thr Ser Leu Gly Gly Gln Phe Ser Ala Arg
        35                  40                  45

Arg Leu Gly Asp Ser Pro Phe Thr Ile Arg Thr Glu Val Pro Gly Ser
    50                  55                  60

Pro Glu Ser Arg Gly Ala Leu Arg Lys Met Ser Asp Leu Leu Glu Leu
65                  70                  75                  80

Met Val Lys Arg Met Asp Met Leu Ala Arg Leu Glu Asn Ser Ser Glu
                85                  90                  95

Leu His Arg Thr Ala Ser Val Ala His Leu Ala Ala Asp Arg Leu Thr
            100                 105                 110

Pro Gly Ala Ser Leu Ile Glu Arg Ile Gln Ala Ile Ala Gln Asn Val
        115                 120                 125

Ser Asp Ile Ala Val Lys Val Asp Gln Ile Leu Arg His Ser Leu Ile
130                 135                 140

Leu His Ser Lys Val Ser Glu Gly Arg Arg Asp Gln Cys Glu Ala Pro
145                 150                 155                 160

Ser Asp Pro Lys Phe Pro Asp Cys Ser Gly Lys Val Glu Trp Met Arg
                165                 170                 175

Ala Arg Trp Thr Ser Asp Pro Cys Tyr Ala Phe Phe Gly Val Asp Gly
            180                 185                 190

Thr Glu Cys Ser Phe Leu Ile Tyr Leu Ser Glu Val Glu Trp Phe Cys
        195                 200                 205

Pro Pro Leu Pro Trp Arg Asn Gln Thr Ala Ala Arg Thr Ala Pro Lys
    210                 215                 220

Ser Leu Pro Arg Val Gln Ala Val Phe Arg Ser Asn Leu Ser His Leu
225                 230                 235                 240

Leu Glu Leu Met Gly Ser Gly Lys Glu Ser Leu Ile Phe Met Lys Lys
                245                 250                 255

Arg Thr Arg Arg Phe Thr Ala Gln Trp Thr Lys Ala Ala Lys Tyr Leu
            260                 265                 270

Ala Gln Lys Leu Gly Asp Ile Arg Arg Asp Gln Lys Gln Ile Leu Val
        275                 280                 285
```

```
His Ile Gly Phe Leu Thr Glu Glu Ser Gly Asp Val Phe Ser Pro Arg
    290                 295                 300
Val Leu Lys Gly Gly Pro Leu Gly Glu Met Val Gln Trp Ala Asp Ile
305                 310                 315                 320
Leu Ala Ala Leu Tyr Val Leu Gly His Ser Leu Arg Ile Thr Val Ser
                325                 330                 335
Leu Lys Glu Leu Gln Ser Asn Leu Gly Val Pro Pro Gly Arg Gly Asn
            340                 345                 350
Cys Pro Leu Thr Val Pro Leu Pro Phe Asp Leu Ile Tyr Thr Asp Tyr
        355                 360                 365
His Gly Leu Gln Gln Met Lys Gln His Met Gly Leu Ser Phe Lys Lys
    370                 375                 380
Tyr Arg Cys Arg Ile Arg Val Ile Asp Thr Phe Gly Thr Glu Pro Ala
385                 390                 395                 400
Tyr Asn His Glu Glu Tyr Ala Thr Leu His Gly Tyr Arg Thr Asn Trp
                405                 410                 415
Gly Tyr Trp Asn Leu Asn Pro Lys Gln Phe Met Thr Met Phe Pro His
            420                 425                 430
Thr Pro Asp Asn Ser Phe Met Gly Phe Val Ser Glu Glu Leu Asn Glu
        435                 440                 445
Thr Glu Lys Gln Leu Ile Lys Asp Gly Lys Ala Ser Asn Met Ala Val
    450                 455                 460
Val Tyr Gly Lys Glu Ala Ser Ile Trp Lys Leu Gln Gly Lys Glu Lys
465                 470                 475                 480
Phe Leu Ala Val Leu Asn Lys Tyr Met Glu Ile His Gly Thr Val Tyr
                485                 490                 495
Tyr Glu Ser Gln Arg Pro Pro Glu Val Pro Ala Phe Val Lys Asn His
            500                 505                 510
Gly Leu Leu Pro Gln Pro Glu Phe Gln Gln Leu Leu Arg Lys Ala Lys
        515                 520                 525
Leu Phe Ile Gly Phe Gly Phe Pro Tyr Glu Gly Pro Ala Pro Leu Glu
    530                 535                 540
Ala Ile Ala Asn Gly Cys Ile Phe Leu Gln Ser Arg Phe Ser Pro Pro
545                 550                 555                 560
His Ser Ser Leu Asn His Glu Phe Phe Arg Gly Lys Pro Thr Ser Arg
                565                 570                 575
Glu Val Phe Ser Gln His Pro Tyr Ala Glu Asn Phe Ile Gly Lys Pro
            580                 585                 590
His Val Trp Thr Val Asp Tyr Asn Asn Ser Asp Glu Phe Glu Thr Ala
        595                 600                 605
Ile Lys Ala Ile Met Asn Thr Gln Val Asp Pro Tyr Leu Pro Tyr Glu
    610                 615                 620
Tyr Thr Cys Ala Gly Met Leu Glu Arg Ile Asn Ala Tyr Ile Gln His
625                 630                 635                 640
Gln Asp Phe Cys Val Gly Pro Ser Pro Leu Pro Gly Ala Ser Thr
                645                 650                 655
Ala Gln Ser Pro Phe Val Leu Ala Pro Asn Ala Thr His Leu Glu Trp
            660                 665                 670
Ala Gln Asn Ile Ser Ser Val Pro Gly Ala Trp Pro Pro Thr His Ser
        675                 680                 685
Leu Arg Ala Trp Leu Ala Ala Pro Gly Arg Ala Cys Thr Asp Ala Cys
    690                 695                 700
```

```
Leu Asp His Gly Leu Ile Cys Glu Pro Ser Phe Pro Phe Leu Asn
705                 710                 715                 720

Ser Gln Asn Ser Phe Leu Lys Leu Gln Val Pro Cys Asp Ser Thr Glu
            725                 730                 735

Trp Glu Met His His Leu Tyr Pro Ala Phe Ala Gln Pro Gly Gln Glu
                740                 745                 750

Cys Tyr Leu Gln Lys Glu Pro Leu Leu Phe Ser Cys Ala Gly Ala Ser
            755                 760                 765

Thr Lys Tyr Gln Arg Leu Cys Pro Cys Arg Asp Phe Arg Lys Gly Gln
            770                 775                 780

Val Ala Leu Cys Gln Gly Cys Leu
785                 790

<210> SEQ ID NO 28
<211> LENGTH: 741
<212> TYPE: PRT
<213> ORGANISM: Homo sapiens

<400> SEQUENCE: 28

Met Ala Leu Phe Thr Pro Trp Lys Leu Ser Ser Gln Lys Leu Gly Phe
1               5                   10                  15

Phe Leu Val Thr Phe Gly Phe Ile Trp Gly Met Met Leu Leu His Phe
                20                  25                  30

Thr Ile Gln Gln Arg Thr Gln Pro Glu Ser Ser Met Leu Arg Glu
            35                  40                  45

Gln Ile Leu Asp Leu Ser Lys Arg Tyr Ile Lys Ala Leu Ala Glu Glu
    50                  55                  60

Asn Arg Asn Val Val Asp Gly Pro Tyr Ala Gly Val Met Thr Ala Tyr
65                  70                  75                  80

Asp Leu Lys Lys Thr Leu Ala Val Leu Leu Asp Asn Ile Leu Gln Arg
                85                  90                  95

Ile Gly Lys Leu Glu Ser Lys Val Asp Asn Leu Val Val Asn Gly Thr
            100                 105                 110

Gly Thr Asn Ser Thr Asn Ser Thr Thr Ala Val Pro Ser Leu Val Ala
            115                 120                 125

Leu Glu Lys Ile Asn Val Ala Asp Ile Ile Asn Gly Ala Gln Glu Lys
    130                 135                 140

Cys Val Leu Pro Pro Met Asp Gly Tyr Pro His Cys Glu Gly Lys Ile
145                 150                 155                 160

Lys Trp Met Lys Asp Met Trp Arg Ser Asp Pro Cys Tyr Ala Asp Tyr
                165                 170                 175

Gly Val Asp Gly Ser Thr Cys Ser Phe Phe Ile Tyr Leu Ser Glu Val
            180                 185                 190

Glu Asn Trp Cys Pro His Leu Pro Trp Arg Ala Lys Asn Pro Tyr Glu
        195                 200                 205

Glu Ala Asp His Asn Ser Leu Ala Glu Ile Arg Thr Asp Phe Asn Ile
    210                 215                 220

Leu Tyr Ser Met Met Lys Lys His Glu Glu Phe Arg Trp Met Arg Leu
225                 230                 235                 240

Arg Ile Arg Arg Met Ala Asp Ala Trp Ile Gln Ala Ile Lys Ser Leu
                245                 250                 255

Ala Glu Lys Gln Asn Leu Glu Lys Arg Lys Arg Lys Lys Val Leu Val
            260                 265                 270

His Leu Gly Leu Leu Thr Lys Glu Ser Gly Phe Lys Ile Ala Glu Thr
        275                 280                 285
```

```
Ala Phe Ser Gly Gly Pro Leu Gly Glu Leu Val Gln Trp Ser Asp Leu
    290                 295                 300
Ile Thr Ser Leu Tyr Leu Leu Gly His Asp Ile Arg Ile Ser Ala Ser
305                 310                 315                 320
Leu Ala Glu Leu Lys Glu Ile Met Lys Lys Val Val Gly Asn Arg Ser
                325                 330                 335
Gly Cys Pro Thr Val Gly Asp Arg Ile Val Glu Leu Ile Tyr Ile Asp
            340                 345                 350
Ile Val Gly Leu Ala Gln Phe Lys Lys Thr Leu Gly Pro Ser Trp Val
        355                 360                 365
His Tyr Gln Cys Met Leu Arg Val Leu Asp Ser Phe Gly Thr Glu Pro
    370                 375                 380
Glu Phe Asn His Ala Asn Tyr Ala Gln Ser Lys Gly His Lys Thr Pro
385                 390                 395                 400
Trp Gly Lys Trp Asn Leu Asn Pro Gln Gln Phe Tyr Thr Met Phe Pro
                405                 410                 415
His Thr Pro Asp Asn Ser Phe Leu Gly Phe Val Val Glu Gln His Leu
            420                 425                 430
Asn Ser Ser Asp Ile His His Ile Asn Glu Ile Lys Arg Gln Asn Gln
        435                 440                 445
Ser Leu Val Tyr Gly Lys Val Asp Ser Phe Trp Lys Asn Lys Lys Ile
    450                 455                 460
Tyr Leu Asp Ile Ile His Thr Tyr Met Glu Val His Ala Thr Val Tyr
465                 470                 475                 480
Gly Ser Ser Thr Lys Asn Ile Pro Ser Tyr Val Lys Asn His Gly Ile
                485                 490                 495
Leu Ser Gly Arg Asp Leu Gln Phe Leu Leu Arg Glu Thr Lys Leu Phe
            500                 505                 510
Val Gly Leu Gly Phe Pro Tyr Glu Gly Pro Ala Pro Leu Glu Ala Ile
        515                 520                 525
Ala Asn Gly Cys Ala Phe Leu Asn Pro Lys Phe Asn Pro Pro Lys Ser
    530                 535                 540
Ser Lys Asn Thr Asp Phe Phe Ile Gly Lys Pro Thr Leu Arg Glu Leu
545                 550                 555                 560
Thr Ser Gln His Pro Tyr Ala Glu Val Phe Ile Gly Arg Pro His Val
                565                 570                 575
Trp Thr Val Asp Leu Asn Asn Gln Glu Glu Val Glu Asp Ala Val Lys
            580                 585                 590
Ala Ile Leu Asn Gln Lys Ile Glu Pro Tyr Met Pro Tyr Glu Phe Thr
        595                 600                 605
Cys Glu Gly Met Leu Gln Arg Ile Asn Ala Phe Ile Glu Lys Gln Asp
    610                 615                 620
Phe Cys His Gly Gln Val Met Trp Pro Pro Leu Ser Ala Leu Gln Val
625                 630                 635                 640
Lys Leu Ala Glu Pro Gly Gln Ser Cys Lys Gln Val Cys Gln Glu Ser
                645                 650                 655
Gln Leu Ile Cys Glu Pro Ser Phe Phe Gln His Leu Asn Lys Asp Lys
            660                 665                 670
Asp Met Leu Lys Tyr Lys Val Thr Cys Gln Ser Ser Glu Leu Ala Lys
        675                 680                 685
Asp Ile Leu Val Pro Ser Phe Asp Pro Lys Asn Lys His Cys Val Phe
    690                 695                 700
```

-continued

```
Gln Gly Asp Leu Leu Leu Phe Ser Cys Ala Gly Ala His Pro Arg His
705                 710                 715                 720

Gln Arg Val Cys Pro Cys Arg Asp Phe Ile Lys Gly Gln Val Ala Leu
            725                 730                 735

Cys Lys Asp Cys Leu
            740

<210> SEQ ID NO 29
<211> LENGTH: 790
<212> TYPE: PRT
<213> ORGANISM: Homo sapiens

<400> SEQUENCE: 29

Met Ile Thr Val Asn Pro Asp Gly Lys Ile Met Val Arg Arg Cys Leu
1               5                   10                  15

Val Thr Leu Arg Pro Phe Arg Leu Phe Val Leu Gly Ile Gly Phe Phe
            20                  25                  30

Thr Leu Cys Phe Leu Met Thr Ser Leu Gly Gly Gln Phe Ser Ala Arg
            35                  40                  45

Arg Leu Gly Asp Ser Pro Phe Thr Ile Arg Thr Glu Val Met Gly Gly
        50                  55                  60

Pro Glu Ser Arg Gly Val Leu Arg Lys Met Ser Asp Leu Leu Glu Leu
65                  70                  75                  80

Met Val Lys Arg Met Asp Ala Leu Ala Arg Leu Glu Asn Ser Ser Glu
                85                  90                  95

Leu His Arg Ala Gly Gly Asp Leu His Phe Pro Ala Asp Arg Met Pro
            100                 105                 110

Pro Gly Ala Gly Leu Met Glu Arg Ile Gln Ala Ile Ala Gln Asn Val
            115                 120                 125

Ser Asp Ile Ala Val Lys Val Asp Gln Ile Leu Arg His Ser Leu Leu
        130                 135                 140

Leu His Ser Lys Val Ser Glu Gly Arg Arg Asp Gln Cys Glu Ala Pro
145                 150                 155                 160

Ser Asp Pro Lys Phe Pro Asp Cys Ser Gly Lys Val Glu Trp Met Arg
                165                 170                 175

Ala Arg Trp Thr Ser Asp Pro Cys Tyr Ala Phe Phe Gly Val Asp Gly
            180                 185                 190

Thr Glu Cys Ser Phe Leu Ile Tyr Leu Ser Glu Val Glu Trp Phe Cys
            195                 200                 205

Pro Pro Leu Pro Trp Arg Asn Gln Thr Ala Ala Gln Arg Ala Pro Lys
        210                 215                 220

Pro Leu Pro Lys Val Gln Ala Val Phe Arg Ser Asn Leu Ser His Leu
225                 230                 235                 240

Leu Asp Leu Met Gly Ser Gly Lys Glu Ser Leu Ile Phe Met Lys Lys
                245                 250                 255

Arg Thr Lys Arg Leu Thr Ala Gln Trp Ala Leu Ala Ala Gln Arg Leu
            260                 265                 270

Ala Gln Lys Leu Gly Ala Thr Gln Arg Asp Gln Lys Gln Ile Leu Val
            275                 280                 285

His Ile Gly Phe Leu Thr Glu Glu Ser Gly Asp Val Phe Ser Pro Arg
        290                 295                 300

Val Leu Lys Gly Gly Pro Leu Gly Glu Met Val Gln Trp Ala Asp Ile
305                 310                 315                 320

Leu Thr Ala Leu Tyr Val Leu Gly His Gly Leu Arg Val Thr Val Ser
                325                 330                 335
```

```
Leu Lys Glu Leu Gln Ser Asn Leu Gly Val Pro Pro Gly Arg Gly Ser
            340                 345                 350

Cys Pro Leu Thr Met Pro Leu Pro Phe Asp Leu Ile Tyr Thr Asp Tyr
            355                 360                 365

His Gly Leu Gln Gln Met Lys Arg His Met Gly Leu Ser Phe Lys Lys
370                 375                 380

Tyr Arg Cys Arg Ile Arg Val Ile Asp Thr Phe Gly Thr Glu Pro Ala
385                 390                 395                 400

Tyr Asn His Glu Glu Tyr Ala Thr Leu His Gly Tyr Arg Thr Asn Trp
                405                 410                 415

Gly Tyr Trp Asn Leu Asn Pro Lys Gln Phe Met Thr Met Phe Pro His
            420                 425                 430

Thr Pro Asp Asn Ser Phe Met Gly Phe Val Ser Glu Glu Leu Asn Glu
            435                 440                 445

Thr Glu Lys Arg Leu Ile Lys Gly Gly Lys Ala Ser Asn Met Ala Val
            450                 455                 460

Val Tyr Gly Lys Glu Ala Ser Ile Trp Lys Gly Lys Glu Lys Phe Leu
465                 470                 475                 480

Gly Ile Leu Asn Lys Tyr Met Glu Ile His Gly Thr Val Tyr Tyr Glu
                485                 490                 495

Ser Gln Arg Pro Pro Glu Val Pro Ala Phe Val Lys Asn His Gly Leu
            500                 505                 510

Leu Pro Gln Pro Glu Phe Gln Gln Leu Leu Arg Lys Ala Lys Leu Phe
            515                 520                 525

Ile Gly Phe Gly Phe Pro Tyr Glu Gly Pro Ala Pro Leu Glu Ala Ile
            530                 535                 540

Ala Asn Gly Cys Ile Phe Leu Gln Ser Arg Phe Ser Pro Pro His Ser
545                 550                 555                 560

Ser Leu Asn His Glu Phe Phe Arg Gly Lys Pro Thr Ser Arg Glu Val
                565                 570                 575

Phe Ser Gln His Pro Tyr Ala Glu Asn Phe Ile Gly Lys Pro His Val
            580                 585                 590

Trp Thr Val Asp Tyr Asn Asn Ser Glu Glu Phe Glu Ala Ala Ile Lys
            595                 600                 605

Ala Ile Met Arg Thr Gln Val Asp Pro Tyr Leu Pro Tyr Glu Tyr Thr
            610                 615                 620

Cys Glu Gly Met Leu Glu Arg Ile His Ala Tyr Ile Gln His Gln Asp
625                 630                 635                 640

Phe Cys Arg Ala Pro Asp Pro Ala Leu Pro Glu Ala His Ala Pro Gln
                645                 650                 655

Ser Pro Phe Val Leu Ala Pro Asn Ala Thr His Leu Glu Trp Ala Arg
            660                 665                 670

Asn Thr Ser Leu Ala Pro Gly Ala Trp Pro Ala His Ala Leu Arg
            675                 680                 685

Ala Trp Leu Ala Val Pro Gly Arg Ala Cys Thr Asp Thr Cys Leu Asp
            690                 695                 700

His Gly Leu Ile Cys Glu Pro Ser Phe Phe Pro Phe Leu Asn Ser Gln
705                 710                 715                 720

Asp Ala Phe Leu Lys Leu Gln Val Pro Cys Asp Ser Thr Glu Ser Glu
                725                 730                 735

Met Asn His Leu Tyr Pro Ala Phe Ala Gln Pro Gly Gln Glu Cys Tyr
            740                 745                 750
```

-continued

```
Leu Gln Lys Glu Pro Leu Leu Phe Ser Cys Ala Gly Ser Asn Thr Lys
            755                 760                 765
Tyr Arg Arg Leu Cys Pro Cys Arg Asp Phe Arg Lys Gly Gln Val Ala
        770                 775                 780
Leu Cys Gln Gly Cys Leu
785                 790

<210> SEQ ID NO 30
<211> LENGTH: 801
<212> TYPE: PRT
<213> ORGANISM: Homo sapiens

<400> SEQUENCE: 30

Met His Ser Phe Val Lys His Leu Cys Ser Arg Tyr Val Val Glu Arg
1               5                   10                  15
Gln Gly Thr Met Ala Leu Pro Ala Leu Leu Thr Arg Leu Leu Pro Leu
            20                  25                  30
Arg Arg Leu Phe Val Leu Gly Ile Gly Phe Phe Thr Leu Cys Phe Leu
        35                  40                  45
Met Thr Ser Leu Gly Gly Gln Phe Ser Ala Arg Arg Leu Gly Asp Ser
    50                  55                  60
Pro Phe Thr Ile Arg Thr Glu Val Met Gly Pro Glu Ser Arg Gly
65                  70                  75                  80
Val Leu Arg Lys Met Ser Asp Leu Leu Glu Leu Met Val Lys Arg Met
                85                  90                  95
Asp Ala Leu Ala Arg Leu Glu Asn Ser Ser Glu Leu His Arg Ala Gly
            100                 105                 110
Gly Asp Leu His Phe Pro Ala Asp Arg Met Pro Pro Gly Ala Gly Leu
        115                 120                 125
Met Glu Arg Ile Gln Ala Ile Ala Gln Asn Val Ser Asp Ile Ala Val
    130                 135                 140
Lys Val Asp Gln Ile Leu Arg His Ser Leu Leu Leu His Ser Lys Val
145                 150                 155                 160
Ser Glu Gly Arg Arg Asp Gln Cys Glu Ala Pro Ser Asp Pro Lys Phe
                165                 170                 175
Pro Asp Cys Ser Gly Lys Val Glu Trp Met Arg Ala Arg Trp Thr Ser
            180                 185                 190
Asp Pro Cys Tyr Ala Phe Phe Gly Val Asp Gly Thr Glu Cys Ser Phe
        195                 200                 205
Leu Ile Tyr Leu Ser Glu Val Glu Trp Phe Cys Pro Pro Leu Pro Trp
    210                 215                 220
Arg Asn Gln Thr Ala Ala Gln Arg Ala Pro Lys Pro Leu Pro Lys Val
225                 230                 235                 240
Gln Ala Val Phe Arg Ser Asn Leu Ser His Leu Leu Asp Leu Met Gly
                245                 250                 255
Ser Gly Lys Glu Ser Leu Ile Phe Met Lys Lys Arg Thr Lys Arg Leu
            260                 265                 270
Thr Ala Gln Trp Ala Leu Ala Ala Gln Arg Leu Ala Gln Lys Leu Gly
        275                 280                 285
Ala Thr Gln Arg Asp Gln Lys Gln Ile Leu Val His Ile Gly Phe Leu
    290                 295                 300
Thr Glu Glu Ser Gly Asp Val Phe Ser Pro Arg Val Leu Lys Gly Gly
305                 310                 315                 320
Pro Leu Gly Glu Met Val Gln Trp Ala Asp Ile Leu Thr Ala Leu Tyr
                325                 330                 335
```

```
Val Leu Gly His Gly Leu Arg Val Thr Val Ser Leu Lys Glu Leu Gln
            340                 345                 350

Ser Asn Leu Gly Val Pro Pro Arg Gly Ser Cys Pro Leu Thr Met
        355                 360                 365

Pro Leu Pro Phe Asp Leu Ile Tyr Thr Asp Tyr His Gly Leu Gln Gln
370                 375                 380

Met Lys Arg His Met Gly Leu Ser Phe Lys Lys Tyr Arg Cys Arg Ile
385                 390                 395                 400

Arg Val Ile Asp Thr Phe Gly Thr Glu Pro Ala Tyr Asn His Glu Glu
                405                 410                 415

Tyr Ala Thr Leu His Gly Tyr Arg Thr Asn Trp Gly Tyr Trp Asn Leu
            420                 425                 430

Asn Pro Lys Gln Phe Met Thr Met Phe Pro His Thr Pro Asp Asn Ser
        435                 440                 445

Phe Met Gly Phe Val Ser Glu Glu Leu Asn Glu Thr Glu Lys Arg Leu
    450                 455                 460

Ile Lys Gly Gly Lys Ala Ser Asn Met Ala Val Val Tyr Gly Lys Glu
465                 470                 475                 480

Ala Ser Ile Trp Lys Gly Lys Glu Lys Phe Leu Gly Ile Leu Asn Lys
                485                 490                 495

Tyr Met Glu Ile His Gly Thr Val Tyr Tyr Glu Ser Gln Arg Pro Pro
            500                 505                 510

Glu Val Pro Ala Phe Val Lys Asn His Gly Leu Leu Pro Gln Pro Glu
        515                 520                 525

Phe Gln Gln Leu Leu Arg Lys Ala Lys Leu Phe Ile Gly Phe Gly Phe
    530                 535                 540

Pro Tyr Glu Gly Pro Ala Pro Leu Glu Ala Ile Ala Asn Gly Cys Ile
545                 550                 555                 560

Phe Leu Gln Ser Arg Phe Ser Pro Pro His Ser Ser Leu Asn His Glu
                565                 570                 575

Phe Phe Arg Gly Lys Pro Thr Ser Arg Glu Val Phe Ser Gln His Pro
            580                 585                 590

Tyr Ala Glu Asn Phe Ile Gly Lys Pro His Val Trp Thr Val Asp Tyr
        595                 600                 605

Asn Asn Ser Glu Glu Phe Glu Ala Ala Ile Lys Ala Ile Met Arg Thr
    610                 615                 620

Gln Val Asp Pro Tyr Leu Pro Tyr Glu Tyr Thr Cys Glu Gly Met Leu
625                 630                 635                 640

Glu Arg Ile His Ala Tyr Ile Gln His Gln Asp Phe Cys Arg Ala Pro
                645                 650                 655

Asp Pro Ala Leu Pro Glu Ala His Ala Pro Gln Ser Pro Phe Val Leu
            660                 665                 670

Ala Pro Asn Ala Thr His Leu Glu Trp Ala Arg Asn Thr Ser Leu Ala
        675                 680                 685

Pro Gly Ala Trp Pro Pro Ala His Ala Leu Arg Ala Trp Leu Ala Val
    690                 695                 700

Pro Gly Arg Ala Cys Thr Asp Thr Cys Leu Asp His Gly Leu Ile Cys
705                 710                 715                 720

Glu Pro Ser Phe Phe Pro Phe Leu Asn Ser Gln Asp Ala Phe Leu Lys
                725                 730                 735

Leu Gln Val Pro Cys Asp Ser Thr Glu Ser Glu Met Asn His Leu Tyr
            740                 745                 750
```

```
Pro Ala Phe Ala Gln Pro Gly Gln Glu Cys Tyr Leu Gln Lys Glu Pro
            755                 760                 765

Leu Leu Phe Ser Cys Ala Gly Ser Asn Thr Lys Tyr Arg Arg Leu Cys
770                 775                 780

Pro Cys Arg Asp Phe Arg Lys Gly Gln Val Ala Leu Cys Gln Gly Cys
785                 790                 795                 800

Leu

<210> SEQ ID NO 31
<211> LENGTH: 464
<212> TYPE: PRT
<213> ORGANISM: Gallus gallus

<400> SEQUENCE: 31

Met Arg Cys Ser Pro Lys Arg Ser Leu Thr Ala Val Ile Ala Ala Ser
1               5                   10                  15

Phe Leu Leu Leu Leu Leu Leu Leu His Arg Gly Ser Trp Gln
            20                  25                  30

Asp Pro Gln Glu Val Gln Phe Arg Asp Leu Pro Ser Asp Ala Val Leu
        35                  40                  45

Lys Ile Leu Lys Gln Gly Ser Leu His Ile Leu Gln Asp Thr Asp Asn
50                  55                  60

Leu Cys Ala Leu His Asn Ile Ser Tyr His Leu Leu Ala Gly Ser Pro
65                  70                  75                  80

Leu Pro His Lys Lys Phe Leu Ala Val Gly Leu Ser Ser Val Arg Arg
                85                  90                  95

Pro Arg Gly Tyr Tyr Leu Pro Asp Thr Leu Gln Ser Leu Phe Lys Gln
            100                 105                 110

Ser Ser Glu Glu Glu Leu Gln Glu Met Val Val Val His Leu Ala
        115                 120                 125

Asp Ala Asp Pro Ile Trp Asn Ala Gln Val Ala Ala Asp Ile Ser His
130                 135                 140

Arg Phe Ala His His Ile Leu Leu Gly Arg Leu Val Leu Ile His Thr
145                 150                 155                 160

Pro His Glu Phe Tyr Pro Thr Leu Glu Gly Leu Lys Arg Asn Tyr Asn
                165                 170                 175

Asp Pro Glu Glu Arg Val Lys Phe Arg Ser Lys Gln Asn Val Asp Tyr
            180                 185                 190

Ala Phe Leu Phe Thr Phe Ala Ala Asn Leu Ser Ser Tyr Tyr Leu Met
        195                 200                 205

Ile Glu Asp Asp Val Trp Ser Ala Lys Ser Phe Phe Thr Ala Ile Arg
210                 215                 220

Lys Ala Val Ala Ser Gln Glu Gly Ser Asn Trp Ala Thr Leu Glu Phe
225                 230                 235                 240

Ser Lys Leu Gly Tyr Ile Gly Lys Leu Tyr Arg Ser Ser Asp Leu Pro
                245                 250                 255

Arg Leu Ala Arg Phe Leu Leu Leu Phe Tyr Gln Glu Met Pro Cys Asp
            260                 265                 270

Trp Leu Leu Thr His Phe Arg Leu Leu Leu Thr Gln Lys Asp Val Ile
        275                 280                 285

Arg Phe Lys Pro Ser Leu Phe Gln His Met Gly Leu Tyr Ser Ser Phe
290                 295                 300

Gln Gly Thr Val Asn Arg Leu Glu Asp Glu Phe Gln Ala Asp Ala
305                 310                 315                 320
```

Met Asp Leu Pro Asp Asn Pro Pro Ala Ala Leu Phe Thr Asn Met Val
               325                 330                 335

Val Phe Glu Asn Tyr Glu Pro Ser Lys Ala Tyr Ser Thr Ala Arg Gly
           340                 345                 350

Tyr Phe Trp Gly Lys Asn Pro Ala Val Gly Ser Ile Phe Ser Ile Val
       355                 360                 365

Phe His Gln Pro Ala Arg Val Thr Arg Val Arg Val Gln Thr Gly Ser
   370                 375                 380

Ser Glu Arg Pro Gly Asp Phe Leu His Ala Gly Val Leu Glu Leu Gly
385                 390                 395                 400

Arg Gly Arg Arg Ala Asp Gly Arg Asp Cys Ser Val Tyr Thr Thr Val
               405                 410                 415

Gly Thr Phe Glu Lys Gly Asn Leu Glu Trp Arg Gly Leu Glu Lys Gly
           420                 425                 430

Met Pro Asn Pro Val Glu Cys Val Arg Ile Arg Val Thr Gln Ser Gln
       435                 440                 445

Ser Glu Trp Leu Ile Ile Gln Ser Ile Gly Ile Trp Thr Ala Gly Thr
   450                 455                 460

<210> SEQ ID NO 32
<211> LENGTH: 575
<212> TYPE: PRT
<213> ORGANISM: Mus musculus

<400> SEQUENCE: 32

Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Gly Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys His Leu Glu Gly Asn Glu
    130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

```
Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Asn Asp Lys Asn Ile Gln Val
        275                 280                 285

Val Glu Leu Pro Ile Val Asp Ser Leu His Pro Arg Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Glu Ala Thr Lys Lys
                340                 345                 350

Leu Gly Phe Lys His Pro Val Ile Gly Val His Val Arg Arg Thr Asp
            355                 360                 365

Lys Val Gly Thr Glu Ala Ala Phe His Pro Ile Glu Glu Tyr Met Val
    370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Thr Leu Leu Lys Glu
                405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Lys Pro Arg Thr Glu Glu Glu Ile Pro Met Glu Pro Gly Asp Ile
        515                 520                 525

Ile Gly Val Ala Gly Asn His Trp Asp Gly Tyr Ser Lys Gly Ile Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 33
<211> LENGTH: 575
<212> TYPE: PRT
<213> ORGANISM: Homo sapiens

<400> SEQUENCE: 33

Met Arg Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
```

```
                35                  40                  45
Lys Leu Glu Arg Leu Lys Gln Gln Asn Glu Asp Leu Arg Arg Met Ala
 50                  55                  60
Glu Ser Leu Arg Ile Pro Gly Pro Ile Asp Gln Gly Pro Ala Ile
 65                  70                  75                  80
Gly Arg Val Arg Val Leu Glu Glu Gln Leu Val Lys Ala Lys Glu Gln
                 85                  90                  95
Ile Glu Asn Tyr Lys Lys Gln Thr Arg Asn Gly Leu Gly Lys Asp His
                100                 105                 110
Glu Ile Leu Arg Arg Ile Glu Asn Gly Ala Lys Glu Leu Trp Phe
                115                 120                 125
Phe Leu Gln Ser Glu Leu Lys Lys Leu Lys Asn Leu Glu Gly Asn Glu
130                 135                 140
Leu Gln Arg His Ala Asp Glu Phe Leu Leu Asp Leu Gly His His Glu
145                 150                 155                 160
Arg Ser Ile Met Thr Asp Leu Tyr Tyr Leu Ser Gln Thr Asp Gly Ala
                165                 170                 175
Gly Asp Trp Arg Glu Lys Glu Ala Lys Asp Leu Thr Glu Leu Val Gln
                180                 185                 190
Arg Arg Ile Thr Tyr Leu Gln Asn Pro Lys Asp Cys Ser Lys Ala Lys
                195                 200                 205
Lys Leu Val Cys Asn Ile Asn Lys Gly Cys Gly Tyr Gly Cys Gln Leu
210                 215                 220
His His Val Val Tyr Cys Phe Met Ile Ala Tyr Gly Thr Gln Arg Thr
225                 230                 235                 240
Leu Ile Leu Glu Ser Gln Asn Trp Arg Tyr Ala Thr Gly Gly Trp Glu
                245                 250                 255
Thr Val Phe Arg Pro Val Ser Glu Thr Cys Thr Asp Arg Ser Gly Ile
                260                 265                 270
Ser Thr Gly His Trp Ser Gly Glu Val Lys Asp Lys Asn Val Gln Val
                275                 280                 285
Val Glu Leu Pro Ile Val Asp Ser Leu His Pro Arg Pro Pro Tyr Leu
290                 295                 300
Pro Leu Ala Val Pro Glu Asp Leu Ala Asp Arg Leu Val Arg Val His
305                 310                 315                 320
Gly Asp Pro Ala Val Trp Trp Val Ser Gln Phe Val Lys Tyr Leu Ile
                325                 330                 335
Arg Pro Gln Pro Trp Leu Glu Lys Glu Ile Glu Ala Thr Lys Lys
                340                 345                 350
Leu Gly Phe Lys His Pro Val Ile Gly Val His Val Arg Arg Thr Asp
                355                 360                 365
Lys Val Gly Thr Glu Ala Ala Phe His Pro Ile Glu Glu Tyr Met Val
                370                 375                 380
His Val Glu Glu His Phe Gln Leu Leu Ala Arg Arg Met Gln Val Asp
385                 390                 395                 400
Lys Lys Arg Val Tyr Leu Ala Thr Asp Asp Pro Ser Leu Leu Lys Glu
                405                 410                 415
Ala Lys Thr Lys Tyr Pro Asn Tyr Glu Phe Ile Ser Asp Asn Ser Ile
                420                 425                 430
Ser Trp Ser Ala Gly Leu His Asn Arg Tyr Thr Glu Asn Ser Leu Arg
                435                 440                 445
Gly Val Ile Leu Asp Ile His Phe Leu Ser Gln Ala Asp Phe Leu Val
                450                 455                 460
```

```
Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Ile Tyr Ala
                500                 505                 510

His Gln Pro Arg Thr Ala Asp Glu Ile Pro Met Glu Pro Gly Asp Ile
            515                 520                 525

Ile Gly Val Ala Gly Asn His Trp Asp Gly Tyr Ser Lys Gly Val Asn
            530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 34
<211> LENGTH: 398
<212> TYPE: PRT
<213> ORGANISM: Homo sapiens

<400> SEQUENCE: 34

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
                20                  25                  30

His Leu Gly Val Thr Leu Val Tyr Tyr Leu Ala Gly Arg Asp Leu Ser
            35                  40                  45

Arg Leu Pro Gln Leu Val Gly Val Ser Thr Pro Leu Gln Gly Gly Ser
50                  55                  60

Asn Ser Ala Ala Ala Ile Gly Gln Ser Ser Gly Glu Leu Arg Thr Gly
65                  70                  75                  80

Gly Ala Arg Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
                100                 105                 110

Asn Leu Thr Ser Val Pro Val Pro His Thr Thr Ala Leu Ser Leu Pro
            115                 120                 125

Ala Cys Pro Glu Glu Ser Pro Leu Leu Val Gly Pro Met Leu Ile Glu
130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
            195                 200                 205

Tyr Gly Ile Tyr Val Ile Asn Gln Ala Gly Asp Thr Ile Phe Asn Arg
            210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
```

```
                    260               265                 270
Met Asp Lys Phe Gly Phe Ser Leu Pro Tyr Val Gln Tyr Phe Gly Gly
                275               280               285

Val Ser Ala Leu Ser Lys Gln Gln Phe Leu Thr Ile Asn Gly Phe Pro
            290               295               300

Asn Asn Tyr Trp Gly Trp Gly Gly Glu Asp Asp Ile Phe Asn Arg
305               310               315               320

Leu Val Phe Arg Gly Met Ser Ile Ser Arg Pro Asn Ala Val Val Gly
                325               330               335

Arg Cys Arg Met Ile Arg His Ser Arg Asp Lys Lys Asn Glu Pro Asn
            340               345               350

Pro Gln Arg Phe Asp Arg Ile Ala His Thr Lys Glu Thr Met Leu Ser
            355               360               365

Asp Gly Leu Asn Ser Leu Thr Tyr Gln Val Leu Asp Val Gln Arg Tyr
            370               375               380

Pro Leu Tyr Thr Gln Ile Thr Val Asp Ile Gly Thr Pro Ser
385               390               395

<210> SEQ ID NO 35
<211> LENGTH: 346
<212> TYPE: PRT
<213> ORGANISM: Mus musculus

<400> SEQUENCE: 35

Met Arg Phe Arg Glu Gln Phe Leu Gly Gly Ser Ala Ala Met Pro Gly
1               5                   10                  15

Ala Thr Leu Gln Arg Ala Cys Arg Leu Leu Val Ala Val Cys Ala Leu
                20                  25                  30

His Leu Gly Val Thr Leu Val Tyr Tyr Leu Ser Gly Arg Asp Leu Ser
            35                  40                  45

Arg Leu Pro Gln Leu Val Gly Val Ser Ser Thr Leu Gln Gly Gly Thr
        50                  55                  60

Asn Gly Ala Ala Ala Ser Lys Gln Pro Pro Gly Glu Gln Arg Pro Arg
65                  70                  75                  80

Gly Ala Arg Pro Pro Pro Leu Gly Val Ser Pro Lys Pro Arg Pro
                85                  90                  95

Gly Leu Asp Ser Ser Pro Gly Ala Ala Ser Gly Pro Gly Leu Lys Ser
            100                 105                 110

Asn Leu Ser Ser Leu Pro Val Pro Thr Thr Thr Gly Leu Leu Ser Leu
            115                 120                 125

Pro Ala Cys Pro Glu Glu Ser Pro Leu Leu Val Gly Pro Met Leu Ile
    130                 135                 140

Asp Phe Asn Ile Ala Val Asp Leu Glu Leu Leu Ala Lys Lys Asn Pro
145                 150                 155                 160

Glu Ile Lys Thr Gly Gly Arg Tyr Ser Pro Lys Asp Cys Val Ser Pro
                165                 170                 175

His Lys Val Ala Ile Ile Ile Pro Phe Arg Asn Arg Gln Glu His Leu
            180                 185                 190

Lys Tyr Trp Leu Tyr Tyr Leu His Pro Ile Leu Gln Arg Gln Gln Leu
        195                 200                 205

Asp Tyr Gly Ile Tyr Val Ile Asn Gln Ala Gly Asp Thr Met Phe Asn
    210                 215                 220

Arg Ala Lys Leu Leu Asn Ile Gly Phe Gln Glu Ala Leu Lys Asp Tyr
225                 230                 235                 240
```

```
Asp Tyr Asn Cys Phe Val Phe Ser Asp Val Asp Leu Ile Pro Met Asp
                245                 250                 255

Asp Arg Asn Ala Tyr Arg Cys Phe Ser Gln Pro Arg His Ile Ser Val
            260                 265                 270

Ala Met Asp Lys Phe Gly Phe Ser Leu Pro Tyr Val Gln Tyr Phe Gly
        275                 280                 285

Gly Val Ser Ala Leu Ser Lys Gln Gln Phe Leu Ala Ile Asn Gly Phe
    290                 295                 300

Pro Asn Asn Tyr Trp Gly Trp Gly Gly Glu Asp Asp Ile Phe Asn
305                 310                 315                 320

Arg Ser Lys Pro Lys Ala Ser Ala Glu Glu Thr Gly Gly Ser Leu Gly
                325                 330                 335

Lys Ala Leu Ser Pro Ala Ser Thr Arg Ala
                340                 345

<210> SEQ ID NO 36
<211> LENGTH: 438
<212> TYPE: PRT
<213> ORGANISM: Mus musculus

<400> SEQUENCE: 36

Met Lys Pro His Leu Lys Gln Trp Arg Gln Arg Met Leu Phe Gly Ile
1                 5                  10                  15

Phe Val Trp Gly Leu Leu Phe Leu Ala Ile Phe Ile Tyr Phe Thr Asn
                20                  25                  30

Ser Asn Pro Ala Ala Pro Met Pro Ser Ser Phe Ser Phe Leu Glu Arg
            35                  40                  45

Arg Gly Leu Leu Pro Leu Gln Gly Lys Gln Arg Val Ile Met Gly Ala
    50                  55                  60

Leu Gln Glu Pro Ser Leu Pro Arg Ser Leu Asp Ala Ser Lys Val Leu
65                  70                  75                  80

Leu Asp Ser His Pro Glu Asn Pro Phe His Pro Trp Pro Gly Asp Pro
                85                  90                  95

Gln Lys Trp Asp Gln Ala Pro Asn Gly Phe Asp Asn Gly Asp Glu Phe
            100                 105                 110

Phe Thr Ser Gln Val Gly Arg Lys Ser Gln Ser Ala Phe Tyr Pro Glu
        115                 120                 125

Glu Asp Ser Tyr Phe Val Ala Asp Gln Pro Glu Leu Tyr His His
    130                 135                 140

Arg Gln Gly Ala Leu Glu Leu Pro Ser Pro Gly Glu Thr Ser Trp Arg
145                 150                 155                 160

Ser Gly Pro Val Gln Pro Lys Gln Lys Leu Leu His Pro Arg Arg Gly
                165                 170                 175

Ser Leu Pro Glu Glu Ala Tyr Asp Ser Asp Met Leu Ser Ala Ser Met
            180                 185                 190

Ser Arg Ala Phe Leu Tyr Arg Leu Trp Lys Gly Ala Val Ser Ser Lys
        195                 200                 205

Met Leu Asn Pro Arg Leu Gln Lys Ala Met Arg Tyr Tyr Met Ser Phe
    210                 215                 220

Asn Lys His Gly Val Arg Phe Arg Arg Gly Arg Arg Glu Ala Thr
225                 230                 235                 240

Arg Thr Gly Pro Glu Leu Leu Cys Glu Met Arg Arg Val Arg Val
                245                 250                 255

Arg Thr Leu Asp Gly Arg Glu Ala Pro Phe Ser Gly Leu Gly Trp Arg
            260                 265                 270
```

```
Pro Leu Val Pro Gly Val Pro Leu Ser Gln Leu His Pro Arg Gly Leu
            275                 280                 285

Ser Ser Cys Ala Val Val Met Ser Ala Gly Ala Ile Leu Asn Ser Ser
        290                 295                 300

Leu Gly Glu Glu Ile Asp Ser His Asp Ala Val Leu Arg Phe Asn Ser
305                 310                 315                 320

Ala Pro Thr Arg Gly Tyr Glu Lys Asp Val Gly Asn Lys Thr Thr Val
                325                 330                 335

Arg Ile Ile Asn Ser Gln Ile Leu Ala Asn Pro Ser His His Phe Ile
            340                 345                 350

Asp Ser Ala Leu Tyr Lys Asp Val Ile Leu Val Ala Trp Asp Pro Ala
        355                 360                 365

Pro Tyr Ser Ala Asn Leu Asn Leu Trp Tyr Lys Lys Pro Asp Tyr Asn
370                 375                 380

Leu Phe Thr Pro Tyr Ile Gln His Arg Arg Lys Tyr Pro Thr Gln Pro
385                 390                 395                 400

Phe Tyr Ile Leu His Pro Lys Phe Ile Trp Gln Leu Trp Asp Ile Ile
                405                 410                 415

Gln Glu Asn Thr Arg Glu Lys Ile Gln Pro Asn Pro Ser Ser Gly
            420                 425                 430

Phe Ile Gly Thr Cys Val
            435

<210> SEQ ID NO 37
<211> LENGTH: 406
<212> TYPE: PRT
<213> ORGANISM: Homo sapiens

<400> SEQUENCE: 37

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
```

-continued

```
                195                 200                 205
Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
                260                 265                 270

Pro Asp Tyr Asn Phe Phe Asn Asn Tyr Lys Thr Tyr Arg Lys Leu His
                275                 280                 285

Pro Asn Gln Pro Phe Tyr Ile Leu Lys Pro Gln Met Pro Trp Glu Leu
                290                 295                 300

Trp Asp Ile Leu Gln Glu Ile Ser Pro Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
                340                 345                 350

Cys Tyr Tyr Tyr Gln Lys Phe Phe Asp Ser Ala Cys Thr Met Gly Ala
                355                 360                 365

Tyr His Pro Leu Leu Tyr Glu Lys Asn Leu Val Lys His Leu Asn Gln
                370                 375                 380

Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 38
<211> LENGTH: 175
<212> TYPE: PRT
<213> ORGANISM: Homo sapiens

<400> SEQUENCE: 38

Met Asn Ser Gln Leu Val Thr Thr Glu Lys Arg Phe Leu Lys Asp Ser
1               5                   10                  15

Leu Tyr Asn Glu Gly Ile Leu Ile Val Trp Asp Pro Ser Val Tyr His
                20                  25                  30

Ser Asp Ile Pro Lys Trp Tyr Gln Asn Pro Asp Tyr Asn Phe Phe Asn
            35                  40                  45

Asn Tyr Lys Thr Tyr Arg Lys Leu His Pro Asn Gln Pro Phe Tyr Ile
        50                  55                  60

Leu Lys Pro Gln Met Pro Trp Glu Leu Trp Asp Ile Leu Gln Glu Ile
65                  70                  75                  80

Ser Pro Glu Ile Gln Pro Asn Pro Ser Ser Gly Met Leu Gly Ile Ile Ile
                85                  90                  95

Ile Ile Met Met Thr Leu Cys Asp Gln Val Asp Ile Tyr Glu Phe
                100                 105                 110

Leu Pro Ser Lys Arg Lys Thr Asp Val Cys Tyr Tyr Tyr Gln Lys Phe
            115                 120                 125

Phe Asp Ser Ala Cys Thr Met Gly Ala Tyr His Pro Leu Leu Tyr Glu
        130                 135                 140

Lys Asn Leu Val Lys His Leu Asn Gln Gly Thr Asp Glu Asp Ile Tyr
145                 150                 155                 160
```

```
Leu Leu Gly Lys Ala Thr Leu Pro Gly Phe Arg Thr Ile His Cys
                165                 170                 175

<210> SEQ ID NO 39
<211> LENGTH: 337
<212> TYPE: PRT
<213> ORGANISM: Mus musculus

<400> SEQUENCE: 39

Met Arg Arg Lys Thr Leu Lys Tyr Leu Thr Phe Phe Leu Leu Phe Ile
1               5                   10                  15

Phe Leu Thr Ser Phe Val Leu Asn Tyr Ser Asn Thr Gly Val Pro Ser
            20                  25                  30

Ala Trp Phe Pro Lys Gln Met Leu Glu Leu Ser Glu Asn Phe Arg
        35                  40                  45

Arg Phe Ile Lys Ser Gln Pro Cys Thr Cys Arg His Cys Ile Ser Gln
    50                  55                  60

Asp Lys Val Ser Tyr Trp Phe Asp Gln Arg Phe Asn Lys Thr Met Gln
65                  70                  75                  80

Pro Leu Leu Thr Val His Asn Ala Leu Met Glu Glu Asp Thr Tyr Arg
                85                  90                  95

Trp Trp Leu Arg Leu Gln Arg Glu Arg Lys Pro Asn Asn Leu Ser Asp
            100                 105                 110

Thr Val Lys Glu Leu Phe Arg Leu Val Pro Gly Asn Val Asp Pro Met
        115                 120                 125

Leu Asn Lys Arg Leu Val Gly Cys Arg Arg Cys Ala Val Val Gly Asn
    130                 135                 140

Ser Gly Asn Leu Lys Asp Ser Ser Tyr Gly Pro Glu Ile Asp Ser His
145                 150                 155                 160

Asp Phe Val Leu Arg Met Asn Lys Ala Pro Thr Val Gly Phe Glu Ala
                165                 170                 175

Asp Val Gly Ser Arg Thr Thr His His Leu Val Tyr Pro Glu Ser Phe
            180                 185                 190

Arg Glu Leu Gly Glu Asn Val Asn Met Val Leu Val Pro Phe Lys Thr
        195                 200                 205

Thr Asp Leu Gln Trp Val Ile Ser Ala Thr Thr Thr Gly Thr Ile Thr
    210                 215                 220

His Thr Tyr Val Pro Val Pro Pro Lys Ile Lys Val Lys Gln Glu Lys
225                 230                 235                 240

Ile Leu Ile Tyr His Pro Ala Phe Ile Lys Tyr Val Phe Asp Asn Trp
                245                 250                 255

Leu Gln Gly His Gly Arg Tyr Pro Ser Thr Gly Ile Leu Ser Ile Ile
            260                 265                 270

Phe Ser Ile His Ile Cys Asp Glu Val Asp Leu Tyr Gly Phe Gly Ala
        275                 280                 285

Asp Ser Lys Gly Asn Trp His His Tyr Trp Glu Asn Asn Pro Ser Ala
    290                 295                 300

Gly Ala Phe Arg Lys Thr Gly Val His Asp Gly Asp Phe Glu Tyr Asn
305                 310                 315                 320

Ile Thr Thr Thr Leu Ala Ala Ile Asn Lys Ile Arg Ile Phe Lys Gly
                325                 330                 335

Arg

<210> SEQ ID NO 40
<211> LENGTH: 340
```

<212> TYPE: PRT
<213> ORGANISM: Homo sapiens

<400> SEQUENCE: 40

```
Met Val Thr Leu Arg Lys Arg Thr Leu Lys Val Leu Thr Phe Leu Val
1               5                   10                  15

Leu Phe Ile Phe Leu Thr Ser Phe Phe Leu Asn Tyr Ser His Thr Met
            20                  25                  30

Val Ala Thr Thr Trp Phe Pro Lys Gln Met Val Leu Glu Leu Ser Glu
        35                  40                  45

Asn Leu Lys Arg Leu Ile Lys His Arg Pro Cys Thr Cys Thr His Cys
    50                  55                  60

Ile Gly Gln Arg Lys Leu Ser Ala Trp Phe Asp Glu Arg Phe Asn Gln
65                  70                  75                  80

Thr Met Gln Pro Leu Leu Thr Ala Gln Asn Ala Leu Leu Glu Asp Asp
                85                  90                  95

Thr Tyr Arg Trp Trp Leu Arg Leu Gln Arg Glu Lys Lys Pro Asn Asn
            100                 105                 110

Leu Asn Asp Thr Ile Lys Glu Leu Phe Arg Val Val Pro Gly Asn Val
        115                 120                 125

Asp Pro Met Leu Glu Lys Arg Ser Val Gly Cys Arg Arg Cys Ala Val
130                 135                 140

Val Gly Asn Ser Gly Asn Leu Arg Glu Ser Ser Tyr Gly Pro Glu Ile
145                 150                 155                 160

Asp Ser His Asp Phe Val Leu Arg Met Asn Lys Ala Pro Thr Ala Gly
                165                 170                 175

Phe Glu Ala Asp Val Gly Thr Lys Thr Thr His His Leu Val Tyr Pro
            180                 185                 190

Glu Ser Phe Arg Glu Leu Gly Asp Asn Val Ser Met Ile Leu Val Pro
        195                 200                 205

Phe Lys Thr Ile Asp Leu Glu Trp Val Val Ser Ala Ile Thr Thr Gly
210                 215                 220

Thr Ile Ser His Thr Tyr Ile Pro Val Pro Ala Lys Ile Arg Val Lys
225                 230                 235                 240

Gln Asp Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Met His Val Cys Asp Glu Val Asp Leu Tyr Gly
        275                 280                 285

Phe Gly Ala Asp Ser Lys Gly Asn Trp His His Tyr Trp Glu Asn Asn
290                 295                 300

Pro Ser Ala Gly Ala Phe Arg Lys Thr Gly Val His Asp Ala Asp Phe
305                 310                 315                 320

Glu Ser Asn Val Thr Ala Thr Leu Ala Ser Ile Asn Lys Ile Arg Ile
                325                 330                 335

Phe Lys Gly Arg
            340
```

<210> SEQ ID NO 41
<211> LENGTH: 350
<212> TYPE: PRT
<213> ORGANISM: Homo sapiens

<400> SEQUENCE: 41

Met Lys Cys Ser Leu Arg Val Trp Phe Leu Ser Val Ala Phe Leu Leu
1               5                   10                  15

Val Phe Ile Met Ser Leu Leu Phe Thr Tyr Ser His His Ser Met Ala
            20                  25                  30

Thr Leu Pro Tyr Leu Asp Ser Gly Ala Leu Asp Gly Thr His Arg Val
        35                  40                  45

Lys Leu Val Pro Gly Tyr Ala Gly Leu Gln Arg Leu Ser Lys Glu Arg
50                  55                  60

Leu Ser Gly Lys Ser Cys Ala Cys Arg Arg Cys Met Gly Asp Ala Gly
65                  70                  75                  80

Ala Ser Asp Trp Phe Asp Ser His Phe Asp Gly Asn Ile Ser Pro Val
                85                  90                  95

Trp Thr Arg Glu Asn Met Asp Leu Pro Pro Asp Val Gln Arg Trp Trp
            100                 105                 110

Met Met Leu Gln Pro Gln Phe Lys Ser His Asn Thr Asn Glu Val Leu
            115                 120                 125

Glu Lys Leu Phe Gln Ile Val Pro Gly Glu Asn Pro Tyr Arg Phe Arg
        130                 135                 140

Asp Pro His Gln Cys Arg Arg Cys Ala Val Val Gly Asn Ser Gly Asn
145                 150                 155                 160

Leu Arg Gly Ser Gly Tyr Gly Gln Asp Val Asp Gly His Asn Phe Ile
                165                 170                 175

Met Arg Met Asn Gln Ala Pro Thr Val Gly Phe Glu Gln Asp Val Gly
            180                 185                 190

Ser Arg Thr Thr His His Phe Met Tyr Pro Glu Ser Ala Lys Asn Leu
        195                 200                 205

Pro Ala Asn Val Ser Phe Val Leu Val Pro Phe Lys Val Leu Asp Leu
210                 215                 220

Leu Trp Ile Ala Ser Ala Leu Ser Thr Gly Gln Ile Arg Phe Thr Tyr
225                 230                 235                 240

Ala Pro Val Lys Ser Phe Leu Arg Val Asp Lys Glu Lys Val Gln Ile
                245                 250                 255

Tyr Asn Pro Ala Phe Phe Lys Tyr Ile His Asp Arg Trp Thr Glu His
            260                 265                 270

His Gly Arg Tyr Pro Ser Thr Gly Met Leu Val Leu Phe Phe Ala Leu
        275                 280                 285

His Val Cys Asp Glu Val Asn Val Tyr Gly Phe Gly Ala Asp Ser Arg
290                 295                 300

Gly Asn Trp His His Tyr Trp Glu Asn Asn Arg Tyr Ala Gly Glu Phe
305                 310                 315                 320

Arg Lys Thr Gly Val His Asp Ala Asp Phe Glu Ala His Ile Ile Asp
            325                 330                 335

Met Leu Ala Lys Ala Ser Lys Ile Glu Val Tyr Arg Gly Asn
        340                 345                 350

<210> SEQ ID NO 42
<211> LENGTH: 444
<212> TYPE: PRT
<213> ORGANISM: Homo sapiens

<400> SEQUENCE: 42

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

```
Leu Gln Trp Glu Glu Asp Ser Ser Lys Tyr Ser His Ser Ser Pro
        35                  40                  45

Gln Glu Lys Pro Val Ala Asp Ser Val Val Leu Ser Phe Asp Ser Ala
    50                  55                  60

Gly Gln Thr Leu Gly Ser Glu Tyr Asp Arg Leu Gly Phe Leu Leu Asn
65                  70                  75                  80

Leu Asp Ser Lys Leu Ser Pro Arg Thr Leu Cys Thr Val Val Phe Gly
                85                  90                  95

Leu Asp Cys Ile Leu Glu Ser Pro Gly Glu Pro Lys Lys Leu Leu Met
                100                 105                 110

Pro Ala Ser His Pro Leu Glu Ile Leu Lys Ser Leu Ser Glu Asp Thr
            115                 120                 125

Ala Phe Ala Leu Gly Phe Leu Lys Leu Pro Arg Pro Ala Glu Leu Ala
        130                 135                 140

Thr Lys Tyr Ala Asn Phe Ser Glu Gly Ala Cys Lys Pro Gly Tyr Ala
145                 150                 155                 160

Ser Ala Leu Met Thr Ala Ile Phe Pro Arg Phe Ser Lys Pro Ala Pro
                165                 170                 175

Met Phe Leu Asp Asp Ser Phe Arg Lys Trp Ala Arg Ile Arg Glu Phe
                180                 185                 190

Val Pro Pro Phe Gly Ile Lys Gly Gln Asp Asn Leu Ile Lys Ala Ile
            195                 200                 205

Leu Ser Val Thr Lys Glu Tyr Arg Leu Thr Pro Ala Leu Asp Ser Leu
        210                 215                 220

Arg Cys Arg Arg Cys Ile Ile Val Gly Asn Gly Gly Val Leu Ala Asn
225                 230                 235                 240

Lys Ser Leu Gly Ser Arg Ile Asp Asp Tyr Asp Ile Val Val Arg Leu
                245                 250                 255

Asn Ser Ala Pro Val Lys Gly Phe Glu Lys Asp Val Gly Ser Lys Thr
                260                 265                 270

Thr Leu Arg Ile Thr Tyr Pro Glu Gly Ala Met Gln Arg Pro Glu Gln
        275                 280                 285

Tyr Glu Arg Asp Ser Leu Phe Val Leu Ala Gly Phe Lys Trp Gln Asp
        290                 295                 300

Phe Lys Trp Leu Lys Tyr Ile Val Tyr Lys Glu Arg Val Ser Ala Ser
305                 310                 315                 320

Asp Gly Phe Trp Lys Ser Val Ala Thr Arg Val Pro Lys Glu Pro Pro
                325                 330                 335

Glu Ile Arg Ile Leu Asn Pro Tyr Phe Ile Gln Glu Ala Ala Phe Thr
            340                 345                 350

Leu Ile Gly Leu Pro Phe Asn Asn Gly Leu Met Gly Arg Gly Asn Ile
        355                 360                 365

Pro Thr Leu Gly Ser Val Ala Val Thr Met Ala Leu His Gly Cys Asp
        370                 375                 380

Glu Val Ala Val Ala Gly Phe Gly Tyr Asp Met Ser Thr Pro Asn Ala
385                 390                 395                 400

Pro Leu His Tyr Tyr Glu Thr Val Arg Met Ala Ala Ile Lys Glu Ser
                405                 410                 415

Trp Thr His Asn Ile Gln Arg Glu Lys Glu Phe Leu Arg Lys Leu Val
                420                 425                 430

Lys Ala Arg Val Ile Thr Asp Leu Ser Ser Gly Ile
            435                 440
```

```
<210> SEQ ID NO 43
<211> LENGTH: 390
<212> TYPE: PRT
<213> ORGANISM: Homo sapiens

<400> SEQUENCE: 43

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Ser Lys Tyr Ser His Ser Ser Ser Pro
        35                  40                  45

Gln Glu Lys Pro Val Ala Asp Ser Val Val Leu Ser Phe Asp Ser Ala
    50                  55                  60

Gly Gln Thr Leu Gly Ser Glu Tyr Asp Arg Leu Gly Phe Leu Leu Asn
65                  70                  75                  80

Leu Asp Ser Lys Leu Pro Ala Glu Leu Ala Thr Lys Tyr Ala Asn Phe
                85                  90                  95

Ser Glu Gly Ala Cys Lys Pro Gly Tyr Ala Ser Ala Leu Met Thr Ala
            100                 105                 110

Ile Phe Pro Arg Phe Ser Lys Pro Ala Pro Met Phe Leu Asp Asp Ser
        115                 120                 125

Phe Arg Lys Trp Ala Arg Ile Arg Glu Phe Val Pro Pro Phe Gly Ile
    130                 135                 140

Lys Gly Gln Asp Asn Leu Ile Lys Ala Ile Leu Ser Val Thr Lys Glu
145                 150                 155                 160

Tyr Arg Leu Thr Pro Ala Leu Asp Ser Leu Arg Cys Arg Arg Cys Ile
                165                 170                 175

Ile Val Gly Asn Gly Gly Val Leu Ala Asn Lys Ser Leu Gly Ser Arg
            180                 185                 190

Ile Asp Asp Tyr Asp Ile Val Val Arg Leu Asn Ser Ala Pro Val Lys
        195                 200                 205

Gly Phe Glu Lys Asp Val Gly Ser Lys Thr Thr Leu Arg Ile Thr Tyr
    210                 215                 220

Pro Glu Gly Ala Met Gln Arg Pro Glu Gln Tyr Glu Arg Asp Ser Leu
225                 230                 235                 240

Phe Val Leu Ala Gly Phe Lys Trp Gln Asp Phe Lys Trp Leu Lys Tyr
                245                 250                 255

Ile Val Tyr Lys Glu Arg Val Ser Ala Ser Asp Gly Phe Trp Lys Ser
            260                 265                 270

Val Ala Thr Arg Val Pro Lys Glu Pro Pro Glu Ile Arg Ile Leu Asn
        275                 280                 285

Pro Tyr Phe Ile Gln Glu Ala Ala Phe Thr Leu Ile Gly Leu Pro Phe
    290                 295                 300

Asn Asn Gly Leu Met Gly Arg Gly Asn Ile Pro Thr Leu Gly Ser Val
305                 310                 315                 320

Ala Val Thr Met Ala Leu His Gly Cys Asp Glu Val Ala Val Ala Gly
                325                 330                 335

Phe Gly Tyr Asp Met Ser Thr Pro Asn Ala Pro Leu His Tyr Tyr Glu
            340                 345                 350

Thr Val Arg Met Ala Ala Ile Lys Glu Ser Trp Thr His Asn Ile Gln
        355                 360                 365

Arg Glu Lys Glu Phe Leu Arg Lys Leu Val Lys Ala Arg Val Ile Thr
    370                 375                 380
```

```
Asp Leu Ser Ser Gly Ile
385                 390

<210> SEQ ID NO 44
<211> LENGTH: 170
<212> TYPE: PRT
<213> ORGANISM: Homo sapiens

<400> SEQUENCE: 44

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Ser Lys Tyr Ser His Ser Ser Ser Pro
        35                  40                  45

Gln Glu Lys Pro Val Ala Asp Ser Val Val Leu Ser Phe Asp Ser Ala
    50                  55                  60

Gly Gln Thr Leu Gly Ser Glu Tyr Asp Arg Leu Gly Phe Leu Leu Asn
65                  70                  75                  80

Leu Asp Ser Lys Leu Pro Ala Glu Leu Ala Thr Lys Tyr Ala Asn Phe
                85                  90                  95

Ser Glu Gly Ala Cys Lys Pro Gly Tyr Ala Ser Ala Leu Met Thr Ala
            100                 105                 110

Ile Phe Pro Arg Phe Ser Lys Pro Ala Pro Met Phe Leu Asp Asp Ser
        115                 120                 125

Phe Arg Lys Trp Ala Arg Ile Arg Glu Phe Val Pro Pro Phe Gly Ile
    130                 135                 140

Lys Gly Gln Val Leu Asp Ala Gln Tyr Pro Ala Arg Glu Arg Val Ser
145                 150                 155                 160

Ala Glu Ala Gly Glu Ser Ser Arg His His
                165                 170

<210> SEQ ID NO 45
<211> LENGTH: 429
<212> TYPE: PRT
<213> ORGANISM: Homo sapiens

<400> SEQUENCE: 45

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Asn Ser Val Val Leu Ser Phe Asp Ser
        35                  40                  45

Ala Gly Gln Thr Leu Gly Ser Glu Tyr Asp Arg Leu Gly Phe Leu Leu
    50                  55                  60

Asn Leu Asp Ser Lys Leu Ser Pro Arg Thr Leu Cys Thr Val Phe
65                  70                  75                  80

Gly Leu Asp Cys Ile Leu Glu Ser Pro Gly Glu Pro Lys Lys Leu Leu
                85                  90                  95

Met Pro Ala Ser His Pro Leu Glu Ile Leu Lys Ser Leu Ser Glu Asp
            100                 105                 110

Thr Ala Phe Ala Leu Gly Phe Leu Lys Leu Pro Arg Pro Ala Glu Leu
        115                 120                 125

Ala Thr Lys Tyr Ala Asn Phe Ser Glu Gly Ala Cys Lys Pro Gly Tyr
    130                 135                 140
```

```
Ala Ser Ala Leu Met Thr Ala Ile Phe Pro Arg Phe Ser Lys Pro Ala
145                 150                 155                 160

Pro Met Phe Leu Asp Asp Ser Phe Arg Lys Trp Ala Arg Ile Arg Glu
                165                 170                 175

Phe Val Pro Pro Phe Gly Ile Lys Gly Gln Asp Asn Leu Ile Lys Ala
            180                 185                 190

Ile Leu Ser Val Thr Lys Glu Tyr Arg Leu Thr Pro Ala Leu Asp Ser
        195                 200                 205

Leu Arg Cys Arg Arg Cys Ile Ile Val Gly Asn Gly Gly Val Leu Ala
    210                 215                 220

Asn Lys Ser Leu Gly Ser Arg Ile Asp Asp Tyr Asp Ile Val Val Arg
225                 230                 235                 240

Leu Asn Ser Ala Pro Val Lys Gly Phe Glu Lys Asp Val Gly Ser Lys
                245                 250                 255

Thr Thr Leu Arg Ile Thr Tyr Pro Glu Gly Ala Met Gln Arg Pro Glu
            260                 265                 270

Gln Tyr Glu Arg Asp Ser Leu Phe Val Leu Ala Gly Phe Lys Trp Gln
        275                 280                 285

Asp Phe Lys Trp Leu Lys Tyr Ile Val Tyr Lys Glu Arg Val Ser Ala
    290                 295                 300

Ser Asp Gly Phe Trp Lys Ser Val Ala Thr Arg Val Pro Lys Glu Pro
305                 310                 315                 320

Pro Glu Ile Arg Ile Leu Asn Pro Tyr Phe Ile Gln Glu Ala Ala Phe
                325                 330                 335

Thr Leu Ile Gly Leu Pro Phe Asn Asn Gly Leu Met Gly Arg Gly Asn
            340                 345                 350

Ile Pro Thr Leu Gly Ser Val Ala Val Thr Met Ala Leu His Gly Cys
        355                 360                 365

Asp Glu Val Ala Val Ala Gly Phe Gly Tyr Asp Met Ser Thr Pro Asn
    370                 375                 380

Ala Pro Leu His Tyr Tyr Glu Thr Val Arg Met Ala Ala Ile Lys Glu
385                 390                 395                 400

Ser Trp Thr His Asn Ile Gln Arg Glu Lys Glu Phe Leu Arg Lys Leu
                405                 410                 415

Val Lys Ala Arg Val Ile Thr Asp Leu Ser Ser Gly Ile
            420                 425

<210> SEQ ID NO 46
<211> LENGTH: 375
<212> TYPE: PRT
<213> ORGANISM: Homo sapiens

<400> SEQUENCE: 46

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Lys Leu His Leu
                20                  25                  30

Leu Gln Trp Glu Glu Asp Ser Asn Ser Val Val Leu Ser Phe Asp Ser
            35                  40                  45

Ala Gly Gln Thr Leu Gly Ser Glu Tyr Asp Arg Leu Gly Phe Leu Leu
        50                  55                  60

Asn Leu Asp Ser Lys Leu Pro Ala Glu Leu Ala Thr Lys Tyr Ala Asn
65                  70                  75                  80

Phe Ser Glu Gly Ala Cys Lys Pro Gly Tyr Ala Ser Ala Leu Met Thr
```

```
                            85                  90                  95
Ala Ile Phe Pro Arg Phe Ser Lys Pro Ala Pro Met Phe Leu Asp Asp
            100                 105                 110

Ser Phe Arg Lys Trp Ala Arg Ile Arg Glu Phe Val Pro Pro Phe Gly
            115                 120                 125

Ile Lys Gly Gln Asp Asn Leu Ile Lys Ala Ile Leu Ser Val Thr Lys
            130                 135                 140

Glu Tyr Arg Leu Thr Pro Ala Leu Asp Ser Leu Arg Cys Arg Cys
145                 150                 155                 160

Ile Ile Val Gly Asn Gly Val Leu Ala Asn Lys Ser Leu Gly Ser
            165                 170                 175

Arg Ile Asp Asp Tyr Asp Ile Val Val Arg Leu Asn Ser Ala Pro Val
            180                 185                 190

Lys Gly Phe Glu Lys Asp Val Gly Ser Lys Thr Thr Leu Arg Ile Thr
            195                 200                 205

Tyr Pro Glu Gly Ala Met Gln Arg Pro Glu Gln Tyr Glu Arg Asp Ser
            210                 215                 220

Leu Phe Val Leu Ala Gly Phe Lys Trp Gln Asp Phe Lys Trp Leu Lys
225                 230                 235                 240

Tyr Ile Val Tyr Lys Glu Arg Val Ser Ala Ser Asp Gly Phe Trp Lys
                    245                 250                 255

Ser Val Ala Thr Arg Val Pro Lys Glu Pro Glu Ile Arg Ile Leu
            260                 265                 270

Asn Pro Tyr Phe Ile Gln Glu Ala Ala Phe Thr Leu Ile Gly Leu Pro
            275                 280                 285

Phe Asn Asn Gly Leu Met Gly Arg Gly Asn Ile Pro Thr Leu Gly Ser
290                 295                 300

Val Ala Val Thr Met Ala Leu His Gly Cys Asp Glu Val Ala Val Ala
305                 310                 315                 320

Gly Phe Gly Tyr Asp Met Ser Thr Pro Asn Ala Pro Leu His Tyr Tyr
            325                 330                 335

Glu Thr Val Arg Met Ala Ala Ile Lys Glu Ser Trp Thr His Asn Ile
            340                 345                 350

Gln Arg Glu Lys Glu Phe Leu Arg Lys Leu Val Lys Ala Arg Val Ile
            355                 360                 365

Thr Asp Leu Ser Ser Gly Ile
            370                 375

<210> SEQ ID NO 47
<211> LENGTH: 277
<212> TYPE: PRT
<213> ORGANISM: Homo sapiens

<400> SEQUENCE: 47

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
                20                  25                  30

Leu Gln Trp Glu Glu Asp Ser Asn Ser Val Val Leu Ser Phe Asp Ser
            35                  40                  45

Ala Gly Gln Thr Leu Gly Ser Glu Tyr Asp Arg Leu Gly Phe Leu Leu
        50                  55                  60

Asn Leu Asp Ser Lys Leu Pro Ala Glu Leu Ala Thr Lys Tyr Ala Asn
65                  70                  75                  80
```

```
Phe Ser Glu Gly Ala Cys Lys Pro Gly Tyr Ala Ser Ala Leu Met Thr
                85                  90                  95

Ala Ile Phe Pro Arg Phe Ser Lys Pro Ala Pro Met Phe Leu Asp Asp
            100                 105                 110

Ser Phe Arg Lys Trp Ala Arg Ile Arg Glu Phe Val Pro Pro Phe Gly
        115                 120                 125

Ile Lys Gly Gln Asp Asn Leu Ile Lys Ala Ile Leu Ser Val Thr Lys
    130                 135                 140

Glu Tyr Arg Leu Thr Pro Ala Leu Asp Ser Leu Arg Cys Arg Arg Cys
145                 150                 155                 160

Ile Ile Val Gly Asn Gly Gly Val Leu Ala Asn Lys Ser Leu Gly Ser
                165                 170                 175

Arg Ile Asp Asp Tyr Asp Ile Val Val Arg Leu Asn Ser Ala Pro Val
            180                 185                 190

Lys Gly Phe Glu Lys Asp Val Gly Ser Lys Thr Thr Leu Arg Ile Thr
        195                 200                 205

Tyr Pro Glu Gly Ala Met Gln Arg Pro Glu Gln Tyr Glu Arg Asp Ser
    210                 215                 220

Leu Phe Val Leu Ala Gly Phe Lys Trp Gln Asp Phe Lys Trp Leu Lys
225                 230                 235                 240

Tyr Ile Val Tyr Lys Glu Arg Val Ser Trp Thr His Asn Ile Gln Arg
                245                 250                 255

Glu Lys Glu Phe Leu Arg Lys Leu Val Lys Ala Arg Val Ile Thr Asp
            260                 265                 270

Leu Ser Ser Gly Ile
        275

<210> SEQ ID NO 48
<211> LENGTH: 155
<212> TYPE: PRT
<213> ORGANISM: Homo sapiens

<400> SEQUENCE: 48

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Asn Ser Val Val Leu Ser Phe Asp Ser
        35                  40                  45

Ala Gly Gln Thr Leu Gly Ser Glu Tyr Asp Arg Leu Gly Phe Leu Leu
    50                  55                  60

Asn Leu Asp Ser Lys Leu Pro Ala Glu Leu Ala Thr Lys Tyr Ala Asn
65                  70                  75                  80

Phe Ser Glu Gly Ala Cys Lys Pro Gly Tyr Ala Ser Ala Leu Met Thr
                85                  90                  95

Ala Ile Phe Pro Arg Phe Ser Lys Pro Ala Pro Met Phe Leu Asp Asp
            100                 105                 110

Ser Phe Arg Lys Trp Ala Arg Ile Arg Glu Phe Val Pro Pro Phe Gly
        115                 120                 125

Ile Lys Gly Gln Val Leu Asp Ala Gln Tyr Pro Ala Arg Glu Arg Val
    130                 135                 140

Ser Ala Glu Ala Gly Glu Ser Ser Arg His His
145                 150                 155

<210> SEQ ID NO 49
```

<211> LENGTH: 413
<212> TYPE: PRT
<213> ORGANISM: Homo sapiens

<400> SEQUENCE: 49

```
Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Lys Tyr Asp Arg Leu Gly Phe Leu Leu
        35                  40                  45

Asn Leu Asp Ser Lys Leu Ser Pro Arg Thr Leu Cys Thr Val Val Phe
50                  55                  60

Gly Leu Asp Cys Ile Leu Glu Ser Pro Gly Glu Pro Lys Lys Leu Leu
65                  70                  75                  80

Met Pro Ala Ser His Pro Leu Glu Ile Leu Lys Ser Leu Ser Glu Asp
                85                  90                  95

Thr Ala Phe Ala Leu Gly Phe Leu Lys Leu Pro Arg Pro Ala Glu Leu
            100                 105                 110

Ala Thr Lys Tyr Ala Asn Phe Ser Glu Gly Ala Cys Lys Pro Gly Tyr
        115                 120                 125

Ala Ser Ala Leu Met Thr Ala Ile Phe Pro Arg Phe Ser Lys Pro Ala
130                 135                 140

Pro Met Phe Leu Asp Asp Ser Phe Arg Lys Trp Ala Arg Ile Arg Glu
145                 150                 155                 160

Phe Val Pro Pro Phe Gly Ile Lys Gly Gln Asp Asn Leu Ile Lys Ala
                165                 170                 175

Ile Leu Ser Val Thr Lys Glu Tyr Arg Leu Thr Pro Ala Leu Asp Ser
            180                 185                 190

Leu Arg Cys Arg Arg Cys Ile Ile Val Gly Asn Gly Gly Val Leu Ala
        195                 200                 205

Asn Lys Ser Leu Gly Ser Arg Ile Asp Asp Tyr Asp Ile Val Val Arg
210                 215                 220

Leu Asn Ser Ala Pro Val Lys Gly Phe Glu Lys Asp Val Gly Ser Lys
225                 230                 235                 240

Thr Thr Leu Arg Ile Thr Tyr Pro Glu Gly Ala Met Gln Arg Pro Glu
                245                 250                 255

Gln Tyr Glu Arg Asp Ser Leu Phe Val Leu Ala Gly Phe Lys Trp Gln
            260                 265                 270

Asp Phe Lys Trp Leu Lys Tyr Ile Val Tyr Lys Glu Arg Val Ser Ala
        275                 280                 285

Ser Asp Gly Phe Trp Lys Ser Val Ala Thr Arg Val Pro Lys Glu Pro
290                 295                 300

Pro Glu Ile Arg Ile Leu Asn Pro Tyr Phe Ile Gln Glu Ala Ala Phe
305                 310                 315                 320

Thr Leu Ile Gly Leu Pro Phe Asn Asn Gly Leu Met Gly Arg Gly Asn
                325                 330                 335

Ile Pro Thr Leu Gly Ser Val Ala Val Thr Met Ala Leu His Gly Cys
            340                 345                 350

Asp Glu Val Ala Val Ala Gly Phe Gly Tyr Asp Met Ser Thr Pro Asn
        355                 360                 365

Ala Pro Leu His Tyr Tyr Glu Thr Val Arg Met Ala Ala Ile Lys Glu
370                 375                 380

Ser Trp Thr His Asn Ile Gln Arg Glu Lys Glu Phe Leu Arg Lys Leu
```

```
385                 390                 395                 400
Val Lys Ala Arg Val Ile Thr Asp Leu Ser Ser Gly Ile
                405                 410

<210> SEQ ID NO 50
<211> LENGTH: 359
<212> TYPE: PRT
<213> ORGANISM: Homo sapiens

<400> SEQUENCE: 50

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Lys Tyr Asp Arg Leu Gly Phe Leu Leu
        35                  40                  45

Asn Leu Asp Ser Lys Leu Pro Ala Glu Leu Ala Thr Lys Tyr Ala Asn
    50                  55                  60

Phe Ser Glu Gly Ala Cys Lys Pro Gly Tyr Ala Ser Ala Leu Met Thr
65                  70                  75                  80

Ala Ile Phe Pro Arg Phe Ser Lys Pro Ala Pro Met Phe Leu Asp Asp
                85                  90                  95

Ser Phe Arg Lys Trp Ala Arg Ile Arg Glu Phe Val Pro Pro Phe Gly
            100                 105                 110

Ile Lys Gly Gln Asp Asn Leu Ile Lys Ala Ile Leu Ser Val Thr Lys
        115                 120                 125

Glu Tyr Arg Leu Thr Pro Ala Leu Asp Ser Leu Arg Cys Arg Arg Cys
    130                 135                 140

Ile Ile Val Gly Asn Gly Gly Val Leu Ala Asn Lys Ser Leu Gly Ser
145                 150                 155                 160

Arg Ile Asp Asp Tyr Asp Ile Val Val Arg Leu Asn Ser Ala Pro Val
                165                 170                 175

Lys Gly Phe Glu Lys Asp Val Gly Ser Lys Thr Thr Leu Arg Ile Thr
            180                 185                 190

Tyr Pro Glu Gly Ala Met Gln Arg Pro Glu Gln Tyr Glu Arg Asp Ser
        195                 200                 205

Leu Phe Val Leu Ala Gly Phe Lys Trp Gln Asp Phe Lys Trp Leu Lys
    210                 215                 220

Tyr Ile Val Tyr Lys Glu Arg Val Ser Ala Ser Asp Gly Phe Trp Lys
225                 230                 235                 240

Ser Val Ala Thr Arg Val Pro Lys Glu Pro Pro Glu Ile Arg Ile Leu
                245                 250                 255

Asn Pro Tyr Phe Ile Gln Glu Ala Ala Phe Thr Leu Ile Gly Leu Pro
            260                 265                 270

Phe Asn Asn Gly Leu Met Gly Arg Gly Asn Ile Pro Thr Leu Gly Ser
        275                 280                 285

Val Ala Val Thr Met Ala Leu His Gly Cys Asp Glu Val Ala Val Ala
    290                 295                 300

Gly Phe Gly Tyr Asp Met Ser Thr Pro Asn Ala Pro Leu His Tyr Tyr
305                 310                 315                 320

Glu Thr Val Arg Met Ala Ala Ile Lys Glu Ser Trp Thr His Asn Ile
                325                 330                 335

Gln Arg Glu Lys Glu Phe Leu Arg Lys Leu Val Lys Ala Arg Val Ile
            340                 345                 350
```

```
Thr Asp Leu Ser Ser Gly Ile
        355

<210> SEQ ID NO 51
<211> LENGTH: 139
<212> TYPE: PRT
<213> ORGANISM: Homo sapiens

<400> SEQUENCE: 51

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
                20                  25                  30

Leu Gln Trp Glu Glu Asp Ser Lys Tyr Asp Arg Leu Gly Phe Leu Leu
            35                  40                  45

Asn Leu Asp Ser Lys Leu Pro Ala Glu Leu Ala Thr Lys Tyr Ala Asn
50                  55                  60

Phe Ser Glu Gly Ala Cys Lys Pro Gly Tyr Ala Ser Ala Leu Met Thr
65                  70                  75                  80

Ala Ile Phe Pro Arg Phe Ser Lys Pro Ala Pro Met Phe Leu Asp Asp
                85                  90                  95

Ser Phe Arg Lys Trp Ala Arg Ile Arg Glu Phe Val Pro Pro Phe Gly
                100                 105                 110

Ile Lys Gly Gln Val Leu Asp Ala Gln Tyr Pro Ala Arg Glu Arg Val
                115                 120                 125

Ser Ala Glu Ala Gly Glu Ser Ser Arg His His
            130                 135

<210> SEQ ID NO 52
<211> LENGTH: 331
<212> TYPE: PRT
<213> ORGANISM: Homo sapiens

<400> SEQUENCE: 52

Met Arg Gly Tyr Leu Val Ala Ile Phe Leu Ser Ala Val Phe Leu Tyr
1               5                   10                  15

Tyr Val Leu His Cys Ile Leu Trp Gly Thr Asn Val Tyr Trp Val Ala
                20                  25                  30

Pro Val Glu Met Lys Arg Arg Asn Lys Ile Gln Pro Cys Leu Ser Lys
                35                  40                  45

Pro Ala Phe Ala Ser Leu Leu Arg Phe His Gln Phe His Pro Phe Leu
50                  55                  60

Cys Ala Ala Asp Phe Arg Lys Ile Ala Ser Leu Tyr Gly Ser Asp Lys
65                  70                  75                  80

Phe Asp Leu Pro Tyr Gly Met Arg Thr Ser Ala Glu Tyr Phe Arg Leu
                85                  90                  95

Ala Leu Ser Lys Leu Gln Ser Cys Asp Leu Phe Asp Glu Phe Asp Asn
                100                 105                 110

Ile Pro Cys Lys Lys Cys Val Val Gly Asn Gly Gly Val Leu Lys
                115                 120                 125

Asn Lys Thr Leu Gly Lys Ile Asp Ser Tyr Asp Val Ile Ile Arg
130                 135                 140

Met Asn Asn Gly Pro Val Leu Gly His Glu Glu Val Gly Arg Arg
145                 150                 155                 160

Thr Thr Phe Arg Leu Phe Tyr Pro Glu Ser Val Phe Ser Asp Pro Ile
                165                 170                 175
```

His Asn Asp Pro Asn Thr Thr Val Ile Leu Thr Ala Phe Lys Pro His
                180                 185                 190

Asp Leu Arg Trp Leu Leu Glu Leu Leu Met Gly Asp Lys Ile Asn Thr
            195                 200                 205

Asn Gly Phe Trp Lys Lys Pro Ala Leu Asn Leu Ile Tyr Lys Pro Tyr
        210                 215                 220

Gln Ile Arg Ile Leu Asp Pro Phe Ile Ile Arg Thr Ala Ala Tyr Glu
225                 230                 235                 240

Leu Leu His Phe Pro Lys Val Phe Pro Lys Asn Gln Lys Pro Lys His
                245                 250                 255

Pro Thr Thr Gly Ile Ile Ala Ile Thr Leu Ala Phe Tyr Ile Cys His
            260                 265                 270

Glu Val His Leu Ala Gly Phe Lys Tyr Asn Phe Ser Asp Leu Lys Ser
        275                 280                 285

Pro Leu His Tyr Tyr Gly Asn Ala Thr Met Ser Leu Met Asn Lys Asn
        290                 295                 300

Ala Tyr His Asn Val Thr Ala Glu Gln Leu Phe Leu Lys Asp Ile Ile
305                 310                 315                 320

Glu Lys Asn Leu Val Ile Asn Leu Thr Gln Asp
                325                 330

<210> SEQ ID NO 53
<211> LENGTH: 753
<212> TYPE: PRT
<213> ORGANISM: Mus musculus

<400> SEQUENCE: 53

Met Glu Thr His Ala His Leu His Arg Glu Gln Ser Tyr Ala Gly Pro
1               5                   10                  15

His Glu Leu Tyr Phe Lys Lys Leu Ser Ser Lys Lys Lys Gln Val Met
            20                  25                  30

Glu Lys Asn Gly Asn Asn Arg Lys Leu Arg Val Cys Val Ala Thr Cys
        35                  40                  45

Asn Arg Ala Asp Tyr Ser Lys Leu Ala Pro Ile Met Phe Gly Ile Lys
    50                  55                  60

Thr Glu Pro Ala Phe Phe Glu Leu Asp Val Val Leu Gly Ser His
65                  70                  75                  80

Leu Ile Asp Asp Tyr Gly Asn Thr Tyr Arg Met Ile Glu Gln Asp Asp
                85                  90                  95

Phe Asp Ile Asn Thr Arg Leu His Thr Ile Val Arg Gly Glu Asp Glu
            100                 105                 110

Ala Ala Met Val Glu Ser Val Gly Leu Ala Leu Val Lys Leu Pro Asp
        115                 120                 125

Val Leu Asn Arg Leu Lys Pro Asp Ile Met Ile Val His Gly Asp Arg
    130                 135                 140

Phe Asp Ala Leu Ala Leu Ala Thr Ser Ala Ala Leu Met Asn Ile Arg
145                 150                 155                 160

Ile Leu His Ile Glu Gly Gly Glu Val Ser Gly Thr Ile Asp Asp Ser
                165                 170                 175

Ile Arg His Ala Ile Thr Lys Leu Ala His Tyr His Val Cys Cys Thr
            180                 185                 190

Arg Ser Ala Glu Gln His Leu Ile Ser Met Cys Glu Asp His Asp Arg
        195                 200                 205

Ile Leu Leu Ala Gly Cys Pro Ser Tyr Asp Lys Leu Leu Ser Ala Lys
    210                 215                 220

-continued

```
Asn Lys Asp Tyr Met Ser Ile Ile Arg Met Trp Leu Gly Asp Val
225                 230                 235                 240

Lys Cys Lys Asp Tyr Ile Val Ala Leu Gln His Pro Val Thr Thr Asp
            245                 250                 255

Ile Lys His Ser Ile Lys Met Phe Glu Leu Thr Leu Asp Ala Leu Ile
        260                 265                 270

Ser Phe Asn Lys Arg Thr Leu Val Leu Phe Pro Asn Ile Asp Ala Gly
    275                 280                 285

Ser Lys Glu Met Val Arg Val Met Arg Lys Gly Ile Glu His His
290                 295                 300

Pro Asn Phe Arg Ala Val Lys His Val Pro Phe Asp Gln Phe Ile Gln
305                 310                 315                 320

Leu Val Ala His Ala Gly Cys Met Ile Gly Asn Ser Ser Cys Gly Val
                325                 330                 335

Arg Glu Val Gly Ala Phe Gly Thr Pro Val Ile Asn Leu Gly Thr Arg
            340                 345                 350

Gln Ile Gly Arg Glu Thr Gly Glu Asn Val Leu His Val Arg Asp Ala
        355                 360                 365

Asp Thr Gln Asp Lys Ile Leu Gln Ala Leu His Leu Gln Phe Gly Lys
370                 375                 380

Gln Tyr Pro Cys Ser Lys Ile Tyr Gly Asp Gly Asn Ala Val Pro Arg
385                 390                 395                 400

Ile Leu Lys Phe Leu Lys Ser Ile Asp Leu Gln Glu Pro Leu Gln Lys
                405                 410                 415

Lys Phe Cys Phe Pro Val Lys Glu Asn Ile Ser Gln Asp Ile Asp
            420                 425                 430

His Ile Leu Glu Thr Leu Ser Ala Leu Ala Val Asp Leu Gly Gly Thr
        435                 440                 445

Asn Leu Arg Val Ala Ile Val Ser Met Lys Gly Glu Ile Val Lys Lys
450                 455                 460

Tyr Thr Gln Phe Asn Pro Lys Thr Tyr Glu Glu Arg Ile Ser Leu Ile
465                 470                 475                 480

Leu Gln Met Cys Val Glu Ala Ala Glu Ala Val Lys Leu Asn Cys
                485                 490                 495

Arg Ile Leu Gly Val Gly Ile Ser Thr Gly Gly Arg Val Asn Pro Gln
            500                 505                 510

Glu Gly Val Val Leu His Ser Thr Lys Leu Ile Gln Glu Trp Asn Ser
        515                 520                 525

Val Asp Leu Arg Thr Pro Leu Ser Asp Thr Leu His Leu Pro Val Trp
530                 535                 540

Val Asp Asn Asp Gly Asn Cys Ala Ala Met Ala Glu Arg Lys Phe Gly
545                 550                 555                 560

Gln Gly Lys Gly Gln Glu Asn Phe Val Thr Leu Ile Thr Gly Thr Gly
                565                 570                 575

Ile Gly Gly Gly Ile Ile His Gln His Glu Leu Ile His Gly Ser Ser
            580                 585                 590

Phe Cys Ala Ala Glu Leu Gly His Leu Val Val Ser Leu Asp Gly Pro
        595                 600                 605

Asp Cys Ser Cys Gly Ser His Gly Cys Ile Glu Ala Tyr Ala Ser Gly
610                 615                 620

Met Ala Leu Gln Arg Glu Ala Lys Lys Leu His Asp Glu Asp Leu Leu
625                 630                 635                 640
```

```
Leu Val Glu Gly Met Ser Val Pro Lys Asp Glu Ala Val Gly Ala Leu
            645                 650                 655

His Leu Ile Gln Ala Ala Lys Leu Gly Asn Val Lys Ala Gln Ser Ile
            660                 665                 670

Leu Arg Thr Ala Gly Thr Ala Leu Gly Leu Gly Val Val Asn Ile Leu
            675                 680                 685

His Thr Met Asn Pro Ser Leu Val Ile Leu Ser Gly Val Leu Ala Ser
            690                 695                 700

His Tyr Ile His Ile Val Lys Asp Val Ile Arg Gln Gln Ala Leu Ser
705                 710                 715                 720

Ser Val Gln Asp Val Asp Val Val Ser Asp Leu Val Asp Pro Ala
                725                 730                 735

Leu Leu Gly Ala Ala Ser Met Val Leu Asp Tyr Thr Thr Arg Arg Ile
            740                 745                 750

His

<210> SEQ ID NO 54
<211> LENGTH: 722
<212> TYPE: PRT
<213> ORGANISM: Homo sapiens

<400> SEQUENCE: 54

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

Lys Thr Glu Pro Glu Phe Phe Glu Leu Asp Val Val Leu Gly Ser
            35                  40                  45

His Leu Ile Asp Asp Tyr Gly Asn Thr Tyr Arg Met Ile Glu Gln Asp
50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
                100                 105                 110

Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Arg Met Trp Leu Gly Asp Asp
        195                 200                 205

Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
            245                 250                 255
```

-continued

```
Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
        340                 345                 350

Lys Gln Tyr Pro Cys Ser Lys Ile Tyr Gly Asp Gly Asn Ala Val Pro
    355                 360                 365

Arg Ile Leu Lys Phe Leu Lys Ser Ile Asp Leu Gln Glu Pro Leu Gln
370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
        420                 425                 430

Lys Tyr Thr Gln Phe Asn Pro Lys Thr Tyr Glu Arg Ile Asn Leu
    435                 440                 445

Ile Leu Gln Met Cys Val Glu Ala Ala Glu Ala Val Lys Leu Asn
450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
        500                 505                 510

Trp Val Asp Asn Asp Gly Asn Cys Ala Ala Leu Ala Glu Arg Lys Phe
    515                 520                 525

Gly Gln Gly Lys Gly Leu Glu Asn Phe Val Thr Leu Ile Thr Gly Thr
530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
        580                 585                 590

Gly Met Ala Leu Gln Arg Glu Ala Lys Lys Leu His Asp Glu Asp Leu
    595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
        660                 665                 670

Ser His Tyr Ile His Ile Val Lys Asp Val Ile Arg Gln Gln Ala Leu
```

-continued

```
            675                 680                 685
Ser Ser Val Gln Asp Val Asp Val Val Ser Asp Leu Val Asp Pro
    690                 695                 700

Ala Leu Leu Gly Ala Ala Ser Met Val Leu Asp Tyr Thr Thr Arg Arg
705                 710                 715                 720

Ile Tyr

<210> SEQ ID NO 55
<211> LENGTH: 427
<212> TYPE: PRT
<213> ORGANISM: Homo sapiens

<400> SEQUENCE: 55

Met Ser Lys Gly Leu Pro Ala Arg Gln Asp Met Glu Lys Glu Arg Glu
1               5                   10                  15

Thr Leu Gln Ala Trp Lys Glu Arg Val Gly Gln Glu Leu Asp Arg Val
                20                  25                  30

Val Ala Phe Trp Met Glu His Ser His Asp Gln Glu His Gly Gly Phe
            35                  40                  45

Phe Thr Cys Leu Gly Arg Glu Gly Arg Val Tyr Asp Asp Leu Lys Tyr
        50                  55                  60

Val Trp Leu Gln Gly Arg Gln Val Trp Met Tyr Cys Arg Leu Tyr Arg
65                  70                  75                  80

Thr Phe Glu Arg Phe Arg His Ala Gln Leu Asp Ala Ala Lys Ala
                85                  90                  95

Gly Gly Glu Phe Leu Leu Arg Tyr Ala Arg Val Ala Pro Pro Gly Lys
            100                 105                 110

Lys Cys Ala Phe Val Leu Thr Arg Asp Gly Arg Pro Val Lys Val Gln
        115                 120                 125

Arg Thr Ile Phe Ser Glu Cys Phe Tyr Thr Met Ala Met Asn Glu Leu
130                 135                 140

Trp Arg Ala Thr Gly Glu Val Arg Tyr Gln Thr Glu Ala Val Glu Met
145                 150                 155                 160

Met Asp Gln Ile Val His Trp Val Gln Glu Asp Ala Ser Gly Leu Gly
                165                 170                 175

Arg Pro Gln Leu Gln Gly Ala Pro Ala Ala Glu Pro Met Ala Val Pro
            180                 185                 190

Met Met Leu Leu Asn Leu Val Glu Gln Leu Gly Glu Ala Asp Glu Glu
        195                 200                 205

Leu Ala Gly Lys Tyr Ala Glu Leu Gly Asp Trp Cys Ala Arg Arg Ile
210                 215                 220

Leu Gln His Val Gln Arg Asp Gly Gln Ala Val Leu Glu Asn Val Ser
225                 230                 235                 240

Glu Gly Gly Lys Glu Leu Pro Gly Cys Leu Gly Arg Gln Gln Asn Pro
                245                 250                 255

Gly His Thr Leu Glu Ala Gly Trp Phe Leu Leu Arg His Cys Ile Arg
            260                 265                 270

Lys Gly Asp Pro Glu Leu Arg Ala His Val Ile Asp Lys Phe Leu Leu
        275                 280                 285

Leu Pro Phe His Ser Gly Trp Asp Pro Asp His Gly Gly Leu Phe Tyr
        290                 295                 300

Phe Gln Asp Ala Asp Asn Phe Cys Pro Thr Gln Leu Glu Trp Ala Met
305                 310                 315                 320

Lys Leu Trp Trp Pro His Ser Glu Ala Met Ile Ala Phe Leu Met Gly
```

```
                        325                 330                 335
Tyr Ser Asp Ser Gly Asp Pro Val Leu Leu Arg Leu Phe Tyr Gln Val
                340                 345                 350

Ala Glu Tyr Thr Phe Arg Gln Phe Arg Asp Pro Glu Tyr Gly Glu Trp
            355                 360                 365

Phe Gly Tyr Leu Ser Arg Glu Gly Lys Val Ala Leu Ser Ile Lys Gly
        370                 375                 380

Gly Pro Phe Lys Gly Cys Phe His Val Pro Arg Cys Leu Ala Met Cys
385                 390                 395                 400

Glu Glu Met Leu Gly Ala Leu Leu Ser Arg Pro Ala Pro Ala Pro Ser
                405                 410                 415

Pro Ala Pro Thr Pro Ala Cys Arg Gly Ala Glu
                420                 425

<210> SEQ ID NO 56
<211> LENGTH: 359
<212> TYPE: PRT
<213> ORGANISM: Homo sapiens

<400> SEQUENCE: 56

Met Pro Leu Glu Leu Glu Leu Cys Pro Gly Arg Trp Val Gly Gly Gln
1               5                   10                  15

His Pro Cys Phe Ile Ile Ala Glu Ile Gly Gln Asn His Gln Gly Asp
                20                  25                  30

Leu Asp Val Ala Lys Arg Met Ile Arg Met Ala Lys Glu Cys Gly Ala
            35                  40                  45

Asp Cys Ala Lys Phe Gln Lys Ser Glu Leu Glu Phe Lys Phe Asn Arg
        50                  55                  60

Lys Ala Leu Glu Arg Pro Tyr Thr Ser Lys His Ser Trp Gly Lys Thr
65                  70                  75                  80

Tyr Gly Glu His Lys Arg His Leu Glu Phe Ser His Asp Gln Tyr Arg
                85                  90                  95

Glu Leu Gln Arg Tyr Ala Glu Glu Val Gly Ile Phe Phe Thr Ala Ser
            100                 105                 110

Gly Met Asp Glu Met Ala Val Glu Phe Leu His Glu Leu Asn Val Pro
        115                 120                 125

Phe Phe Lys Val Gly Ser Gly Asp Thr Asn Asn Phe Pro Tyr Leu Glu
    130                 135                 140

Lys Thr Ala Lys Lys Gly Arg Pro Met Val Ile Ser Ser Gly Met Gln
145                 150                 155                 160

Ser Met Asp Thr Met Lys Gln Val Tyr Gln Ile Val Lys Pro Leu Asn
                165                 170                 175

Pro Asn Phe Cys Phe Leu Gln Cys Thr Ser Ala Tyr Pro Leu Gln Pro
            180                 185                 190

Glu Asp Val Asn Leu Arg Val Ile Ser Glu Tyr Gln Lys Leu Phe Pro
        195                 200                 205

Asp Ile Pro Ile Gly Tyr Ser Gly His Glu Thr Gly Ile Ala Ile Ser
    210                 215                 220

Val Ala Ala Val Ala Leu Gly Ala Lys Val Leu Glu Arg His Ile Thr
225                 230                 235                 240

Leu Asp Lys Thr Trp Lys Gly Ser Asp His Ser Ala Ser Leu Glu Pro
                245                 250                 255

Gly Glu Leu Ala Glu Leu Val Arg Ser Val Arg Leu Val Glu Arg Ala
            260                 265                 270
```

```
Leu Gly Ser Pro Thr Lys Gln Leu Pro Cys Glu Met Ala Cys Asn
            275                 280                 285

Glu Lys Leu Gly Lys Ser Val Val Ala Lys Val Lys Ile Pro Glu Gly
        290                 295                 300

Thr Ile Leu Thr Met Asp Met Leu Thr Val Lys Val Gly Glu Pro Lys
305                 310                 315                 320

Gly Tyr Pro Pro Glu Asp Ile Phe Asn Leu Val Gly Lys Lys Val Leu
                325                 330                 335

Val Thr Val Glu Glu Asp Asp Thr Ile Met Glu Glu Leu Val Asp Asn
                340                 345                 350

His Gly Lys Lys Ile Lys Ser
            355

<210> SEQ ID NO 57
<211> LENGTH: 432
<212> TYPE: PRT
<213> ORGANISM: Mus musculus

<400> SEQUENCE: 57

Met Asp Ala Leu Glu Lys Gly Ala Ala Thr Ser Gly Pro Ala Pro Arg
1               5                   10                  15

Gly Arg Pro Ser Arg Gly Arg Pro Pro Lys Leu Gln Arg Ser Arg Gly
            20                  25                  30

Ala Gly Arg Gly Leu Glu Lys Pro Pro His Leu Ala Ala Leu Val Leu
        35                  40                  45

Ala Arg Gly Gly Ser Lys Gly Ile Pro Leu Lys Asn Ile Lys Arg Leu
    50                  55                  60

Ala Gly Val Pro Leu Ile Gly Trp Val Leu Arg Ala Ala Leu Asp Ala
65                  70                  75                  80

Gly Val Phe Gln Ser Val Trp Val Ser Thr Asp His Asp Glu Ile Glu
                85                  90                  95

Asn Val Ala Lys Gln Phe Gly Ala Gln Val His Arg Arg Ser Ser Glu
            100                 105                 110

Thr Ser Lys Asp Ser Ser Thr Ser Leu Asp Ala Ile Val Glu Phe Leu
        115                 120                 125

Asn Tyr His Asn Glu Val Asp Ile Val Gly Asn Ile Gln Ala Thr Ser
    130                 135                 140

Pro Cys Leu His Pro Thr Asp Leu Gln Lys Val Ala Glu Met Ile Arg
145                 150                 155                 160

Glu Glu Gly Tyr Asp Ser Val Phe Ser Val Val Arg Arg His Gln Phe
                165                 170                 175

Arg Trp Ser Glu Ile Gln Lys Gly Val Arg Glu Val Thr Glu Pro Leu
            180                 185                 190

Asn Leu Asn Pro Ala Lys Arg Pro Arg Arg Gln Asp Trp Asp Gly Glu
        195                 200                 205

Leu Tyr Glu Asn Gly Ser Phe Tyr Phe Ala Lys Arg His Leu Ile Glu
    210                 215                 220

Met Gly Tyr Leu Gln Gly Gly Lys Met Ala Tyr Tyr Glu Met Arg Ala
225                 230                 235                 240

Glu His Ser Val Asp Ile Asp Val Asp Ile Asp Trp Pro Ile Ala Glu
                245                 250                 255

Gln Arg Val Leu Arg Phe Gly Tyr Phe Gly Lys Glu Lys Leu Lys Glu
            260                 265                 270

Ile Lys Leu Leu Val Cys Asn Ile Asp Gly Cys Leu Thr Asn Gly His
        275                 280                 285
```

-continued

```
Ile Tyr Val Ser Gly Asp Gln Lys Glu Ile Ser Tyr Asp Val Lys
    290                 295                 300

Asp Ala Ile Gly Ile Ser Leu Leu Lys Lys Ser Gly Ile Glu Val Arg
305                 310                 315                 320

Leu Ile Ser Glu Arg Ala Cys Ser Lys Gln Thr Leu Ser Ala Leu Lys
                325                 330                 335

Leu Asp Cys Lys Thr Glu Val Ser Val Ser Asp Lys Leu Ala Thr Val
            340                 345                 350

Asp Glu Trp Arg Lys Glu Met Gly Leu Cys Trp Lys Glu Val Ala Tyr
        355                 360                 365

Leu Gly Asn Glu Val Ser Asp Glu Glu Cys Leu Lys Arg Val Gly Leu
    370                 375                 380

Ser Ala Val Pro Ala Asp Ala Cys Ser Gly Ala Gln Lys Ala Val Gly
385                 390                 395                 400

Tyr Ile Cys Lys Cys Ser Gly Gly Arg Gly Ala Ile Arg Glu Phe Ala
                405                 410                 415

Glu His Ile Phe Leu Leu Ile Glu Lys Val Asn Asn Ser Cys Gln Lys
            420                 425                 430
```

<210> SEQ ID NO 58
<211> LENGTH: 434
<212> TYPE: PRT
<213> ORGANISM: Homo sapiens

<400> SEQUENCE: 58

```
Met Asp Ser Val Glu Lys Gly Ala Ala Thr Ser Val Ser Asn Pro Arg
1               5                   10                  15

Gly Arg Pro Ser Arg Gly Arg Pro Lys Leu Gln Arg Asn Ser Arg
            20                  25                  30

Gly Gly Gln Gly Arg Gly Val Glu Lys Pro Pro His Leu Ala Ala Leu
        35                  40                  45

Ile Leu Ala Arg Gly Gly Ser Lys Gly Ile Pro Leu Lys Asn Ile Lys
    50                  55                  60

His Leu Ala Gly Val Pro Leu Ile Gly Trp Val Leu Arg Ala Ala Leu
65                  70                  75                  80

Asp Ser Gly Ala Phe Gln Ser Val Trp Val Ser Thr Asp His Asp Glu
                85                  90                  95

Ile Glu Asn Val Ala Lys Gln Phe Gly Ala Gln Val His Arg Arg Ser
            100                 105                 110

Ser Glu Val Ser Lys Asp Ser Ser Thr Ser Leu Asp Ala Ile Ile Glu
        115                 120                 125

Phe Leu Asn Tyr His Asn Glu Val Asp Ile Val Gly Asn Ile Gln Ala
    130                 135                 140

Thr Ser Pro Cys Leu His Pro Thr Asp Leu Gln Lys Val Ala Glu Met
145                 150                 155                 160

Ile Arg Glu Glu Gly Tyr Asp Ser Val Phe Ser Val Val Arg Arg His
                165                 170                 175

Gln Phe Arg Trp Ser Glu Ile Gln Lys Gly Val Arg Glu Val Thr Glu
            180                 185                 190

Pro Leu Asn Leu Asn Pro Ala Lys Arg Pro Arg Arg Gln Asp Trp Asp
        195                 200                 205

Gly Glu Leu Tyr Glu Asn Gly Ser Phe Tyr Phe Ala Lys Arg His Leu
    210                 215                 220

Ile Glu Met Gly Tyr Leu Gln Gly Gly Lys Met Ala Tyr Tyr Glu Met
```

```
                225                 230                 235                 240
Arg Ala Glu His Ser Val Asp Ile Asp Val Asp Ile Asp Trp Pro Ile
                    245                 250                 255

Ala Glu Gln Arg Val Leu Arg Tyr Gly Tyr Phe Gly Lys Glu Lys Leu
                260                 265                 270

Lys Glu Ile Lys Leu Leu Val Cys Asn Ile Asp Gly Cys Leu Thr Asn
                275                 280                 285

Gly His Ile Tyr Val Ser Gly Asp Gln Lys Glu Ile Ile Ser Tyr Asp
                290                 295                 300

Val Lys Asp Ala Ile Gly Ile Ser Leu Leu Lys Lys Ser Gly Ile Glu
305                 310                 315                 320

Val Arg Leu Ile Ser Glu Arg Ala Cys Ser Lys Gln Thr Leu Ser Ser
                325                 330                 335

Leu Lys Leu Asp Cys Lys Met Glu Val Ser Val Ser Lys Leu Ala
                340                 345                 350

Val Val Asp Glu Trp Arg Lys Glu Met Gly Leu Cys Trp Lys Glu Val
                355                 360                 365

Ala Tyr Leu Gly Asn Glu Val Ser Asp Glu Glu Cys Leu Lys Arg Val
                370                 375                 380

Gly Leu Ser Gly Ala Pro Ala Asp Ala Cys Ser Thr Ala Gln Lys Ala
385                 390                 395                 400

Val Gly Tyr Ile Cys Lys Cys Asn Gly Gly Arg Gly Ala Ile Arg Glu
                405                 410                 415

Phe Ala Glu His Ile Cys Leu Leu Met Glu Lys Val Asn Asn Ser Cys
                420                 425                 430

Gln Lys

<210> SEQ ID NO 59
<211> LENGTH: 336
<212> TYPE: PRT
<213> ORGANISM: Mus musculus

<400> SEQUENCE: 59

Met Ala Pro Ala Arg Glu Asn Val Ser Leu Phe Phe Lys Leu Tyr Cys
1               5                   10                  15

Leu Thr Val Met Thr Leu Val Ala Ala Tyr Thr Val Ala Leu Arg
                20                  25                  30

Tyr Thr Arg Thr Thr Ala Glu Glu Leu Tyr Phe Ser Thr Thr Ala Val
                35                  40                  45

Cys Ile Thr Glu Val Ile Lys Leu Leu Ile Ser Val Gly Leu Leu Ala
                50                  55                  60

Lys Glu Thr Gly Ser Leu Gly Arg Phe Lys Ala Ser Leu Ser Glu Asn
65                  70                  75                  80

Val Leu Gly Ser Pro Lys Glu Leu Ala Lys Leu Ser Val Pro Ser Leu
                85                  90                  95

Val Tyr Ala Val Gln Asn Asn Met Ala Phe Leu Ala Leu Ser Asn Leu
                100                 105                 110

Asp Ala Ala Val Tyr Gln Val Thr Tyr Gln Leu Lys Ile Pro Cys Thr
                115                 120                 125

Ala Leu Cys Thr Val Leu Met Leu Asn Arg Thr Leu Ser Lys Leu Gln
                130                 135                 140

Trp Ile Ser Val Phe Met Leu Cys Gly Gly Val Thr Leu Val Gln Trp
145                 150                 155                 160

Lys Pro Ala Gln Ala Thr Lys Val Val Val Ala Gln Asn Pro Leu Leu
```

```
            165                 170                 175
Gly Phe Gly Ala Ile Ala Ile Ala Val Leu Cys Ser Gly Phe Ala Gly
            180                 185                 190

Val Tyr Phe Glu Lys Val Leu Lys Ser Ser Asp Thr Ser Leu Trp Val
            195                 200                 205

Arg Asn Ile Gln Met Tyr Leu Ser Gly Ile Val Thr Leu Ala Gly
            210                 215                 220

Thr Tyr Leu Ser Asp Gly Ala Glu Ile Gln Glu Lys Gly Phe Phe Tyr
225                 230                 235                 240

Gly Tyr Thr Tyr Val Trp Phe Val Ile Phe Leu Ala Ser Val Gly
                245                 250                 255

Gly Leu Tyr Thr Ser Val Val Lys Tyr Thr Asp Asn Ile Met Lys
            260                 265                 270

Gly Phe Ser Ala Ala Ala Ile Val Leu Ser Thr Ile Ala Ser Val
            275                 280                 285

Leu Leu Phe Gly Leu Gln Ile Thr Leu Ser Phe Ala Leu Gly Ala Leu
            290                 295                 300

Leu Val Cys Val Ser Ile Tyr Leu Tyr Gly Leu Pro Arg Gln Asp Thr
305                 310                 315                 320

Thr Ser Ile Gln Gln Glu Ala Thr Ser Lys Glu Arg Ile Ile Gly Val
                325                 330                 335
```

```
<210> SEQ ID NO 60
<211> LENGTH: 337
<212> TYPE: PRT
<213> ORGANISM: Homo sapiens

<400> SEQUENCE: 60

Met Ala Ala Pro Arg Asp Asn Val Thr Leu Leu Phe Lys Leu Tyr Cys
1               5                   10                  15

Leu Ala Val Met Thr Leu Met Ala Ala Val Tyr Thr Ile Ala Leu Arg
            20                  25                  30

Tyr Thr Arg Thr Ser Asp Lys Glu Leu Tyr Phe Ser Thr Thr Ala Val
            35                  40                  45

Cys Ile Thr Glu Val Ile Lys Leu Leu Leu Ser Val Gly Ile Leu Ala
        50                  55                  60

Lys Glu Thr Gly Ser Leu Gly Arg Phe Lys Ala Ser Leu Arg Glu Asn
65                  70                  75                  80

Val Leu Gly Ser Pro Lys Glu Leu Leu Lys Leu Ser Val Pro Ser Leu
                85                  90                  95

Val Tyr Ala Val Gln Asn Asn Met Ala Phe Leu Ala Leu Ser Asn Leu
            100                 105                 110

Asp Ala Ala Val Tyr Gln Val Thr Tyr Gln Leu Lys Ile Pro Cys Thr
            115                 120                 125

Ala Leu Cys Thr Val Leu Met Leu Asn Arg Thr Leu Ser Lys Leu Gln
130                 135                 140

Trp Val Ser Val Phe Met Leu Cys Ala Gly Val Thr Leu Val Gln Trp
145                 150                 155                 160

Lys Pro Ala Gln Ala Thr Lys Val Val Glu Gln Asn Pro Leu Leu
            165                 170                 175

Gly Phe Gly Ala Ile Ala Ile Ala Val Leu Cys Ser Gly Phe Ala Gly
            180                 185                 190

Val Tyr Phe Glu Lys Val Leu Lys Ser Ser Asp Thr Ser Leu Trp Val
            195                 200                 205
```

```
Arg Asn Ile Gln Met Tyr Leu Ser Gly Ile Ile Val Thr Leu Ala Gly
            210                 215                 220

Val Tyr Leu Ser Asp Gly Ala Glu Ile Lys Glu Lys Gly Phe Phe Tyr
225                 230                 235                 240

Gly Tyr Thr Tyr Tyr Val Trp Phe Val Ile Phe Leu Ala Ser Val Gly
                245                 250                 255

Gly Leu Tyr Thr Ser Val Val Val Lys Tyr Thr Asp Asn Ile Met Lys
            260                 265                 270

Gly Phe Ser Ala Ala Ala Ala Ile Val Leu Ser Thr Ile Ala Ser Val
        275                 280                 285

Met Leu Phe Gly Leu Gln Ile Thr Leu Thr Phe Ala Leu Gly Thr Leu
    290                 295                 300

Leu Val Cys Val Ser Ile Tyr Leu Tyr Gly Leu Pro Arg Gln Asp Thr
305                 310                 315                 320

Thr Ser Ile Gln Gln Gly Glu Thr Ala Ser Lys Glu Arg Val Ile Gly
                325                 330                 335

Val
```

<210> SEQ ID NO 61
<211> LENGTH: 31
<212> TYPE: DNA
<213> ORGANISM: Artificial sequence
<220> FEATURE:
<223> OTHER INFORMATION: CaMV35Sfwd

<400> SEQUENCE: 61
gaacatatgg tggattgatg tgatctactc c                          31

<210> SEQ ID NO 62
<211> LENGTH: 24
<212> TYPE: DNA
<213> ORGANISM: Artificial sequence
<220> FEATURE:
<223> OTHER INFORMATION: CaMV35Srev

<400> SEQUENCE: 62
aattctcgag gaattcggcc gagg                                  24

<210> SEQ ID NO 63
<211> LENGTH: 19
<212> TYPE: RNA
<213> ORGANISM: Artificial sequence
<220> FEATURE:
<223> OTHER INFORMATION: siRNA

<400> SEQUENCE: 63
ggccauucgu uacuagcaa                                        19

<210> SEQ ID NO 64
<211> LENGTH: 19
<212> TYPE: RNA
<213> ORGANISM: Artificial sequence
<220> FEATURE:
<223> OTHER INFORMATION: siRNA

<400> SEQUENCE: 64
gugguucguu gggaaauga                                        19

<210> SEQ ID NO 65
<211> LENGTH: 19
<212> TYPE: RNA
<213> ORGANISM: Artificial sequence

```
<220> FEATURE:
<223> OTHER INFORMATION: siRNA

<400> SEQUENCE: 65
ccgucugugu gaaauuggu                                                        19

<210> SEQ ID NO 66
<211> LENGTH: 19
<212> TYPE: RNA
<213> ORGANISM: Artificial sequence
<220> FEATURE:
<223> OTHER INFORMATION: siRNA

<400> SEQUENCE: 66
cgguaguagu gcuuguugu                                                        19

<210> SEQ ID NO 67
<211> LENGTH: 19
<212> TYPE: RNA
<213> ORGANISM: Artificial sequence
<220> FEATURE:
<223> OTHER INFORMATION: siRNA

<400> SEQUENCE: 67
cugccaugga uauugucaa                                                        19

<210> SEQ ID NO 68
<211> LENGTH: 19
<212> TYPE: RNA
<213> ORGANISM: Artificial sequence
<220> FEATURE:
<223> OTHER INFORMATION: siRNA

<400> SEQUENCE: 68
gccuuugguc cugaagaaa                                                        19

<210> SEQ ID NO 69
<211> LENGTH: 20
<212> TYPE: DNA
<213> ORGANISM: Artificial sequence
<220> FEATURE:
<223> OTHER INFORMATION: Primer

<400> SEQUENCE: 69
agcaagagtg ctcgtgttgc                                                       20

<210> SEQ ID NO 70
<211> LENGTH: 20
<212> TYPE: DNA
<213> ORGANISM: Artificial sequence
<220> FEATURE:
<223> OTHER INFORMATION: Primer

<400> SEQUENCE: 70
acccgacgtc gtacgtttcc                                                       20

<210> SEQ ID NO 71
<211> LENGTH: 20
<212> TYPE: DNA
<213> ORGANISM: Artificial sequence
<220> FEATURE:
<223> OTHER INFORMATION: Primer

<400> SEQUENCE: 71
atccgtcgga atgtagttcc                                                       20
```

```
<210> SEQ ID NO 72
<211> LENGTH: 19
<212> TYPE: DNA
<213> ORGANISM: Artificial sequence
<220> FEATURE:
<223> OTHER INFORMATION: Primer

<400> SEQUENCE: 72
tactcgtcgg taccctcgt                                               19

<210> SEQ ID NO 73
<211> LENGTH: 20
<212> TYPE: DNA
<213> ORGANISM: Artificial sequence
<220> FEATURE:
<223> OTHER INFORMATION: Primer

<400> SEQUENCE: 73
aggtccttcg cgacaatatc                                              20

<210> SEQ ID NO 74
<211> LENGTH: 20
<212> TYPE: DNA
<213> ORGANISM: Artificial sequence
<220> FEATURE:
<223> OTHER INFORMATION: Primer

<400> SEQUENCE: 74
acggaatcac gaatgacgtt                                              20

<210> SEQ ID NO 75
<211> LENGTH: 21
<212> TYPE: DNA
<213> ORGANISM: Artificial sequence
<220> FEATURE:
<223> OTHER INFORMATION: Primer

<400> SEQUENCE: 75
accgtgaaac agtggattgg a                                            21

<210> SEQ ID NO 76
<211> LENGTH: 22
<212> TYPE: DNA
<213> ORGANISM: Artificial sequence
<220> FEATURE:
<223> OTHER INFORMATION: Primer

<400> SEQUENCE: 76
ctgggatggt gtacgtcaat gt                                           22

<210> SEQ ID NO 77
<211> LENGTH: 20
<212> TYPE: DNA
<213> ORGANISM: Artificial sequence
<220> FEATURE:
<223> OTHER INFORMATION: Primer

<400> SEQUENCE: 77
aggtccttcg cgacaatatc                                              20

<210> SEQ ID NO 78
<211> LENGTH: 20
<212> TYPE: DNA
<213> ORGANISM: Artificial sequence
<220> FEATURE:
<223> OTHER INFORMATION: Primer
```

<400> SEQUENCE: 78
acggaatcac gaatgacgtt                                               20

<210> SEQ ID NO 79
<211> LENGTH: 4433
<212> TYPE: DNA
<213> ORGANISM: Artificial sequence
<220> FEATURE:
<223> OTHER INFORMATION: BSJ-25 vector

<400> SEQUENCE: 79

| gatatcatcg actaattcga gctcggtacc cggggatcct ctagagtcga cctgcaggca | 60 |
| tgcaagcttc agaagcgtgc tatcgaactc aaccagggac gtgcggcaca aatgggcatc | 120 |
| cttgctctca tggtgcacga acagttggga gtctctatcc ttccttaaaa atttaatttt | 180 |
| cattagttgc agtcactccg ctttggtttc acagtcagga ataacactag ctcgtcttca | 240 |
| ccatggatgc caatctcgcc tattcatggt gtataaaagt tcaacatcca aagctagaac | 300 |
| ttttggaaag agaaagaata tccgaatagg gcacggcgtg ccgtattgtt ggagtggact | 360 |
| agcagaaagt gaggaaggca caggatgagt tttctcgaga cataccttca gcgtcgtctt | 420 |
| cactgtcaca gtcaactgac agtaatcgtt gatccggaga gattcaaaat tcaatctgtt | 480 |
| tggacctgga taagacacaa gagcgacatc ctgacatgaa cgccgtaaac agcaaatcct | 540 |
| ggttgaacac gtatcctttt gggggcctcc gctacgacgc tcgctccagc tggggcttcc | 600 |
| ttactataca cagcgcgcat atttcacggt tgccagatgt caagatggcc aagttgacca | 660 |
| gtgccgttcc ggtgctcacc gcgcgcgacg tcgccggagc ggtcgagttc tggaccgacc | 720 |
| ggctcgggtt ctcccgggac ttcgtggagg acgacttcgc cggtgtggtc gggacgacg | 780 |
| tgaccctgtt catcagcgcg gtccaggacc aggtggtgcc ggacaacacc ctggcctggg | 840 |
| tgtgggtgcg cggcctggac gagctgtacg ccgagtggtc ggaggtcgtg tccacgaact | 900 |
| tccgggacgc ctccgggccg gccatgaccg agatcggcga gcagccgtgg gggcgggagt | 960 |
| tcgccctgcg cgacccggcc ggcaactgcg tgcacttcgt ggccgaggag caggactgaa | 1020 |
| ccttccttaa aaatttaatt ttcattagtt gcagtcactc cgctttggtt tcacagtcag | 1080 |
| gaataacact agctcgtctt caccatggat gccaatctcg cctattcatg gtgtataaaa | 1140 |
| gttcaacatc caaagctaga acttttggaa agagaaagaa tatccgaata gggcacggcg | 1200 |
| tgccgtattg ttggagtgga ctagcagaaa gtgaggaagg cacaggatga gttttctcga | 1260 |
| ggccggtctc cctatagtga gtcgtattaa tttcgataag ccaggttaac ctgcattaat | 1320 |
| gaatcggcca acgcgcgggg agaggcggtt tgcgtattgg gcgctcttcc gcttcctcgc | 1380 |
| tcactgactc gctgcgctcg tcgttcggc tgcggcgagc ggtatcagct cactcaaagg | 1440 |
| cggtaatacg gttatccaca gaatcagggg ataacgcagg aaagaacatg tgagcaaaag | 1500 |
| gccagcaaaa ggccaggaac cgtaaaaagg ccgcgttgct ggcgtttttc cataggctcc | 1560 |
| gcccccctga cgagcatcac aaaaatcgac gctcaagtca gaggtggcga aacccgacag | 1620 |
| gactataaag ataccaggcg tttccccctg gaagctccct cgtgcgctct cctgttccga | 1680 |
| ccctgccgct taccggatac ctgtccgcct ttctcccttc gggaagcgtg gcgctttctc | 1740 |
| aatgctcacg ctgtaggtat ctcagttcgg tgtaggtcgt tcgctccaag ctgggctgtg | 1800 |
| tgcacgaacc cccgttcag cccgaccgct gcgccttatc cggtaactat cgtcttgagt | 1860 |
| ccaacccggt aagacacgac ttatcgccac tggcagcagc cactggtaac aggattagca | 1920 |

```
gagcgaggta tgtaggcggt gctacagagt tcttgaagtg gtggcctaac tacggctaca    1980
ctagaaggac agtatttggt atctgcgctc tgctgaagcc agttaccttc ggaaaaagag    2040
ttggtagctc ttgatccggc aaacaaacca ccgctggtag cggtggtttt tttgtttgca    2100
agcagcagat tacgcgcaga aaaaaaggat ctcaagaaga tcctttgatc ttttctacgg    2160
ggtctgacgc tcagtggaac gaaaactcac gttaagggat tttggtcatg agattatcaa    2220
aaaggatctt cacctagatc cttttaaatt aaaaatgaag ttttaaatca atctaaagta    2280
tatatgagta aacttggtct gacagttacc aatgcttaat cagtgaggca cctatctcag    2340
cgatctgtct atttcgttca tccatagttg cctgactccc cgtcgtgtag ataactacga    2400
tacgggaggg cttaccatct ggccccagtg ctgcaatgat accgcgagac ccacgctcac    2460
cggctccaga tttatcagca ataaaccagc cagccggaag ggccgagcgc agaagtggtc    2520
ctgcaacttt atccgcctcc atccagtcta ttaattgttg ccgggaagct agagtaagta    2580
gttcgccagt taatagtttg cgcaacgttg ttgccattgc tacaggcatc gtggtgtcac    2640
gctcgtcgtt tggtatggct tcattcagct ccggttccca acgatcaagg cgagttacat    2700
gatcccccat gttgtgcaaa aaagcggtta gctccttcgg tcctccgatc gttgtcagaa    2760
gtaagttggc cgcagtgtta tcactcatgg ttatggcagc actgcataat tctcttactg    2820
tcatgccatc cgtaagatgc ttttctgtga ctggtgagta ctcaaccaag tcattctgag    2880
aatagtgtat gcggcgaccg agttgctctt gcccggcgtc aatacgggat aataccgcgc    2940
cacatagcag aactttaaaa gtgctcatca ttggaaaacg ttcttcgggg cgaaaactct    3000
caaggatctt accgctgttg agatccagtt cgatgtaacc cactcgtgca cccaactgat    3060
cttcagcatc ttttactttc accagcgttt ctgggtgagc aaaaacagga aggcaaaatg    3120
ccgcaaaaaa gggaataagg gcgacacgga aatgttgaat actcatactc ttcctttttc    3180
aatattattg aagcatttat cagggttatt gtctcatgag cggatacata tttgaatgta    3240
tttagaaaaa taaacaaata ggggttccgc gcacatttcc ccgaaaagtg ccacctgacg    3300
tctaagaaac cattattatc atgacattaa cctataaaaa taggcgtatc acgaggccct    3360
ttcgtctcgc gcgtttcggt gatgacggtg aaaacctctg acacatgcag ctcccggaga    3420
cggtcacagc ttgtctgtaa gcggatgccg ggagcagaca agcccgtcag ggcgcgtcag    3480
cgggtgttgg cgggtgtcgg ggctggctta actatgcggc atcagagcag attgtactga    3540
gagtgcacca tatggtggat tgatgtgatc tactccaaaa atatcaaaga tacagtctca    3600
gaagaccaaa gggcaattga acttttcaa caaagggtaa tatccggaaa cctcctcgga    3660
ttccattgcc cagctatctg tcactttatt gtgaagatag tggaaaagga aggtggctcc    3720
tacaaatgcc atcattgcga taaggaaag gccatcgttg aagatgcctc tgccgacagt    3780
ggtcccaaag atgacccccc acccacgagg agcatcgtgg aaaaagaaga cgttccaacc    3840
acgtcttcaa agcaagtgga ttgatgtgat ctactccaaa aatatcaaag atacagtctc    3900
agaagaccaa agggcaattg agacttttca acaagggta atatccggaa acctcctcgg    3960
attccattgc ccagctatct gtcactttat tgtgaagata gtggaaaagg aagtggctc    4020
ctacaaatgc catcattgcg ataaaggaaa ggccatcgtt gaagatgcct ctgccgacag    4080
tggtcccaaa gatggacccc cacccacgag gagcatcgtg gaaaaagaag acgttccaac    4140
cacgtcttca aagcaagtgg attgatgtga tatctccact gacgtaaggg atgacgcaca    4200
atcccactat ccttcgcaag acccttcctc tatataagga agttcatttc attcggagag    4260
gtacgtattt ttacaacaat taccaacaac aacaacaaac aacaacaaca ttcattttta    4320
```

-continued

```
cattctacaa ctacatctag aactagtgga tccaaggaga tataacaatg aagactaatc    4380
tttttctctt tctcatcttt tcacttctcc tatcattatc ctcggccgaa ttc           4433

<210> SEQ ID NO 80
<211> LENGTH: 819
<212> TYPE: DNA
<213> ORGANISM: Cauliflower mosaic virus

<400> SEQUENCE: 80
catatggtgg attgatgtga tctactccaa aaatatcaaa gatacagtct cagaagacca      60
aagggcaatt gagacttttc aacaaagggt aatatccgga aacctcctcg gattccattg     120
cccagctatc tgtcacttta ttgtgaagat agtggaaaag gaaggtggct cctacaaatg     180
ccatcattgc gataaaggaa aggccatcgt tgaagatgcc tctgccgaca gtggtcccaa     240
agatggaccc ccacccacga ggagcatcgt ggaaaaagaa gacgttccaa ccacgtcttc     300
aaagcaagtg gattgatgtg atctactcca aaaatatcaa agatacagtc tcagaagacc     360
aaagggcaat tgagactttt caacaaaggg taatatccgg aaacctcctc ggattccatt     420
gcccagctat ctgtcacttt attgtgaaga tagtggaaaa ggaaggtggc tcctacaaat     480
gccatcattg cgataaagga aaggccatcg ttgaagatgc ctctgccgac agtggtccca     540
agatggaccc cccacccacg aggagcatcg tggaaaaaga agacgttcca accacgtctt     600
caaagcaagt ggattgatgt gatatctcca ctgacgtaag ggatgacgca caatcccact     660
atccttcgca agaccctttcc tctatataag gaagttcatt tcattcggag aggtacgtat     720
ttttacaaca attaccaaca acaacaacaa acaacaacaa cattacattt tacattctac     780
aactacatct agaactagtg gatccaagga gatataaca                           819

<210> SEQ ID NO 81
<211> LENGTH: 66
<212> TYPE: DNA
<213> ORGANISM: Tobacco mosaic virus

<400> SEQUENCE: 81
atgaagacta atcttttctct ctttctcatc ttttcacttc tcctatcatt atcctcggcc     60
gaattc                                                                66
```

N-GLYCOSYLATION IN TRANSFORMED PHAEODACTYLUM TRICORNUTUM

FIELD OF THE INVENTION

The present invention is directed to methods for improving the N-glycosylation pattern of proteins in *Phaeodactylum tricornutum* in order to produce in these microalgae glycoproteins having N-glycan profiles similar to those of glycoproteins produced by animal cells, especially human cells, which can be used as human or animal therapeutic agents.

BACKGROUND OF THE INVENTION

Pharmaceutical proteins are produced as recombinant proteins by expression in eukaryotic expression systems. After the synthesis of the protein backbone, the recombinant protein is submitted to further post-translational processing including the attachment of sugar residues, a process known as glycosylation. However, eukaryotic organisms exhibit different glycosylation processing involving specific enzymes (glycosyltransferases and glycosidases), and so that the glycosylation patterns, even of the same protein, will be different depending on the eukaryotic cell in which the particular protein is being produced. Thus, the glycosylation pattern of pharmaceutical proteins expressed in eukaryotic host cells differs substantially from the glycosylation pattern of the natural proteins produced in humans and other mammals.

N-Glycosylation: a Major Post-Translational Modification of Secreted Proteins

N-glycosylation is a major post-translational modification step in the synthesis of proteins in eukaryotes. N-glycan processing in the secretory pathway is essential for proteins intended to be secreted or integrated into membranes. N-glycosylation starts when the protein is translated and translocated from the ribosome into the lumen of the endoplasmic reticulum (ER). In this processing, a dolicholphosphate oligosaccharide precursor ($Glc_3Man_9GlcNAc_2$-PP-dolichol) is initially assembled at the cytoplasmic face and finished in the luminal face of the ER membrane (BURDA AND AEBI, *Biochimica et Biophysica Acta*, vol. 1426, p: 239-257, 1999). This precursor is used by the oligosaccharyltransferase (OST) multisubunit complex that catalyses its transfer onto the asparagine residues of the consensus sequences Asn-X-Ser/Thr, when X is different than proline and aspartic acid, of a target protein (BURDA AND AEBI, above mentioned, 1999). The precursor is then deglucosylated/reglucosylated to ensure the quality control of the neosynthesised protein through the interaction with ER-resident chaperones calreticulin and calnexin. These ER events are crucial for proper folding and oligomerization of secreted proteins (HELENIUS AND AEBI, *Science*, vol. 291, p: 2364-2369, 2001), highly conserved in eukaryotes investigated so far. These steps lead to the formation of a limited set of high-mannose-type N-glycans (FIG. 1). In contrast, evolutionary adaptation of N-glycan processing in the Golgi apparatus has given rise to a large variety of organism-specific complex structures. Mannosidases located in this compartment first degrade the oligosaccharide precursor into high-mannose-type N-glycans ranging from $Man_9GlcNAc_2$ (Man-9) to $Man_5GlcNAc_2$ (Man-5). N-acetylglucosaminyltransferase I (GnT I) then transfers a first GlcNAc residue on the $\beta(1,3)$-mannose arm of $Man_5GlcNAc_2$ and opens the door to the synthesis of multiple structurally different complex-type N-glycans (FIG. 1). Then, the actions of α-mannosidase II and GnT II allow the synthesis of the core $GlcNAc_2Man_3GlcNAc_2$. The complex-type oligosaccharides arise from the transfer in the Golgi apparatus of monosaccharide residues onto the core $GlcNAc_2Man_3GlcNAc_2$ under the action of organism-specific glycosyltransferases. As a consequence, mature proteins leaving the secretory pathway harbour multiple organism-specific complex N-glycans allowing the protein to acquire a set of glycan-mediated biological functions. As illustration, N-glycans in mammals are maturated into poly-antennary, poly-sialylated structures harbouring an α(1,6)-linked fucose residue on the proximal N-acetylglucosamine of the core (core-α(1,6)-fucose) (FIG. 1).

Remodelling into Human-Like N-Glycans by Knock-in Strategies

Since glycosylation profiles differs between mammals and eukaryotic host cells, strategies have been developed for the in vivo remodelling of the protein N-linked glycan structures. These strategies include the knock-out of endogenous genes that are involved in the transfer of some specific monomers, and knock-in methodologies based on the expression in the host cells of mammalian enzymes. The knock-in approach results, by complementing the enzyme repertoire of the host cell, in the synthesis in the recombinant expression system of N-linked glycans similar to those found in mammalian cells. As illustration, the remodelling of plant N-glycans into mammalian-like N-glycans has been achieved by expressing a human $\beta(1,4)$-galactosyltransferase in plant cells. Targeted insertion of the human $\beta(1,4)$-galactosyltransferase in *Physcomitrella patens* has also been carried out leading to the addition of terminal $\beta(1,4)$-galactose to endogenous N-glycans. Human N-acetylglucosaminyltransferase III (GnT III) has also been successfully expressed in plants in order to in planta engineer endogenous N-glycans. This transferase is able to introduce $\beta(1,4)$-GlcNAc residue on the $\beta$-mannose of the core mammalian N-glycans (bisecting GlcNAc).

With the exception of IgG, human serum proteins require sialic acid on terminal positions of their N-glycans (FIG. 1). Most non-mammalian eukaryotic cells, such as plants, do not synthesize N-acetyl- and N-glycolylneuraminic acids (Neu5Ac and Neu5Gc), the two main mammalian sialic acids. As consequence, genetic manipulation has been developed for the in planta synthesis of sialylated proteins by expressing enzymes able to synthesise CMP-Neu5Ac, its Golgi transporter and the appropriate sialyltransferases (Paccalet et al., 2007, *Plant Biotechnology Journal*, vol. 5, p 12-25; Castilho et al., 2008, Plant Physiol., vol. 147 (11), p 331-339; Castilho et al., 2010, The journal of Biological Chemistry, vol. 285 (21), p 15923-30.

BRIEF DESCRIPTION OF DRAWINGS

The FIG. 1 shows the biosynthesis of N-linked glycans in mammals.

The FIG. 2 shows the affinodetection using concanavalin A (Con A) and immunodetection using antibodies raised against the core $\beta(1,2)$-xylose (anti-Xyl) and core α(1,3)-fucose (anti-Fuc) epitopes of proteins isolated from green onion used as a positive control (Lane 1) and from *Phaeodactylum tricornutum* (Lane 2).

Figure 3:
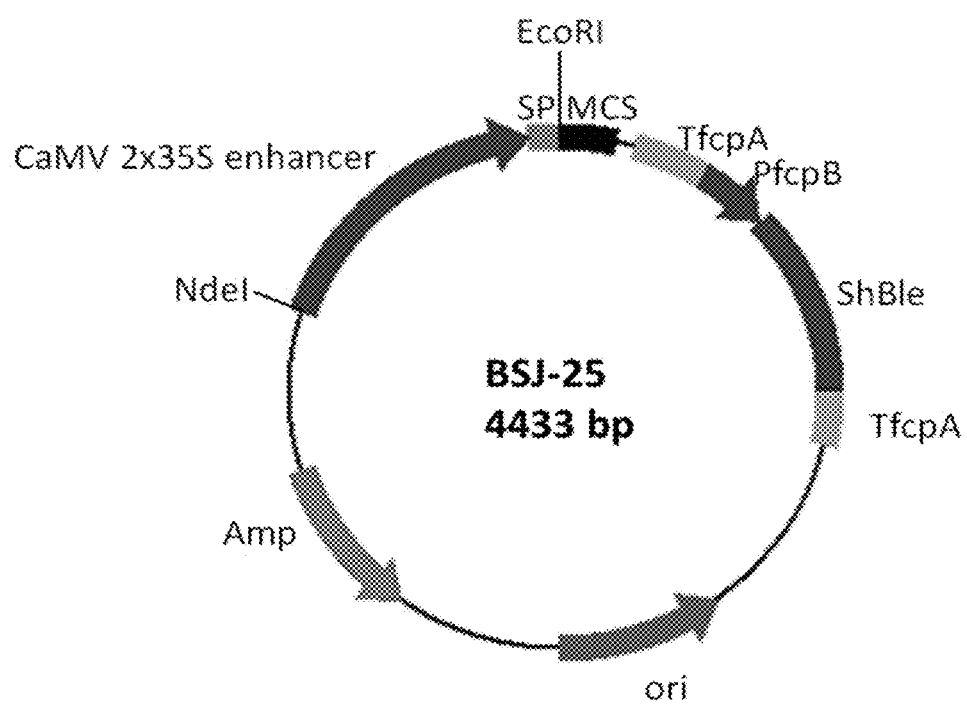

The FIG. 3 shows the transformation vector BSJ-25 (SEQ ID No79). The expression cassette is made up of a double cauliflower mosaic virus (CaMV) 35S promoter (SEQ ID No80), a tobacco mosaic virus-Ω sequence as translation enhancer and an *Arabidopsis* chitinase signal peptide (SP) (SEQ ID No81) which are placed upstream of the multiclonal site (MCS) and the sequence of FcpA terminator of *Phaeodactylum tricornutum* at the end. Selection marker, the bleomycin-resistant gene, ShBle is driven by the FcpB promoter. The construct also contains the ampicillin-resistant gene, Amp and the *Escherichia coli* replication origin.

Figure 4:
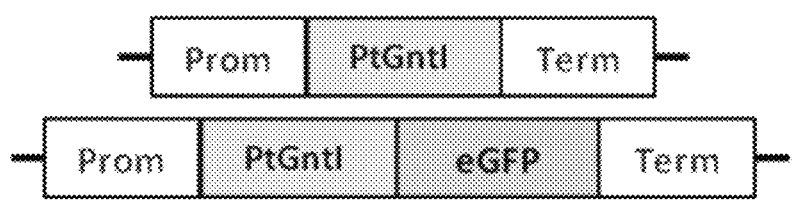

The FIG. 4 shows the expression cassette of *Phaeodactylum tricornutum* GnT I. The first cassette comprised the sequence coding for the endogenous GnT I placed under the control of endogenous regulatory sequences. In the second construction, the GnT I was fused to the Green Fluorescent Protein (GFP).

Figure 5:
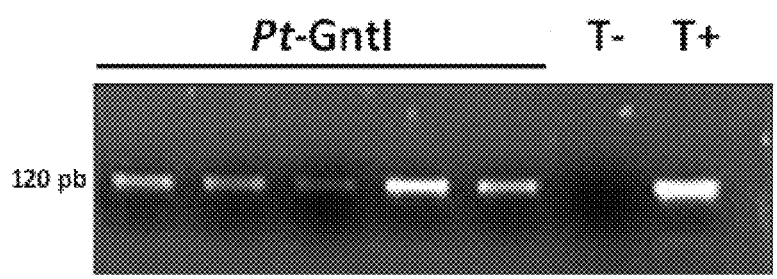

The FIG. 5 shows the screening of transformed microalgae with the sequence coding for the *Phaeodactylum tricornutum* GnT I (Pt-GnT I). Pt-GnT I: potentially transformed microalgae; T−: water amplification negative control; T+: PCR amplification realised on the transformation vector.

Figure 6:
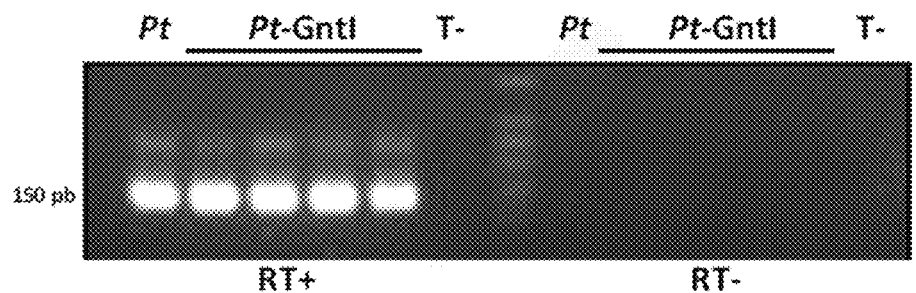

The FIG. 6 shows PCR amplifications of the H4 housekeeping gene realised on the cDNA obtained from the *P. tricornutum* lineages which where transformed with the sequence coding for the GnT I protein (Pt-GnT I). Pt: wild strain of *P. tricornutum*; T−: water amplification negative control; RT+: PCR amplification realised on the cDNA; RT−: Reverse Transcription negative control.

Figure 7:
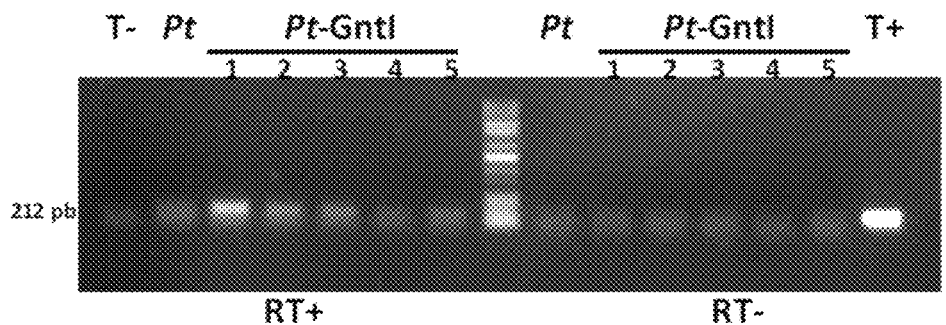

The FIG. 7 shows PCR amplification of GnT I realised on the cDNA obtained from *P. tricornutum* which were transformed with the sequence coding for the endogenous GnT I (Pt-GnT I). Pt: wild strain of *P. tricornutum*; T−: water amplification negative control; RT+: PCR amplification realised on the cDNA; RT−: Reverse Transcription negative control.

The FIG. 8 shows Q-PCR realised on a wild type *P. tricornutum* lineage and on a lineage expressing the GnT I transgene. A: Fusion curve of the amplicons; B: amplification profiles of the wild-type and transformed lineages of *P. tricornutum*. Pt-GnT I: amplification curves obtained for 3 dilutions of cDNA from the transformed lineage with the GnT I gene. Pt-wt: amplification curves obtained for 3 dilutions of cDNA from the wild-type lineage.

Figure 9:
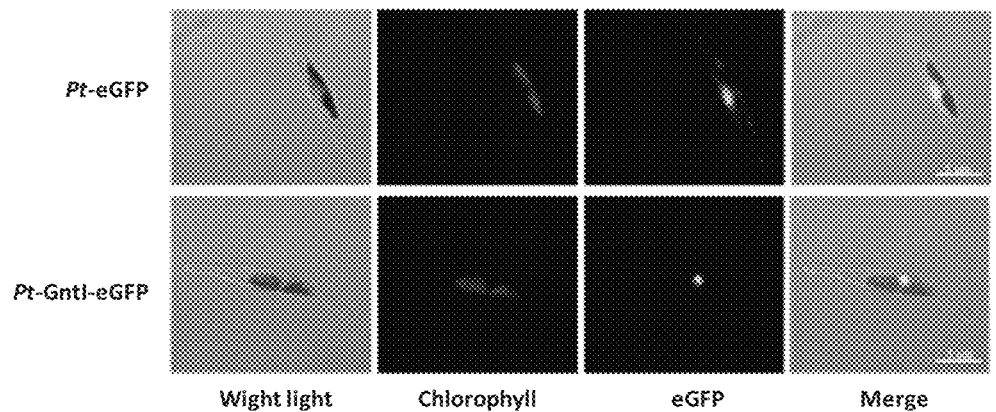

The FIG. 9 shows confocal microscopy observation of *P. tricornutum* microalgae which were transformed with the genes coding for a cytosolic Green Fluorescent Protein (Pt-eGFP) and a GnT I-eGFP fusion protein (Pt-GnT I-eGFP).

Figure 10:
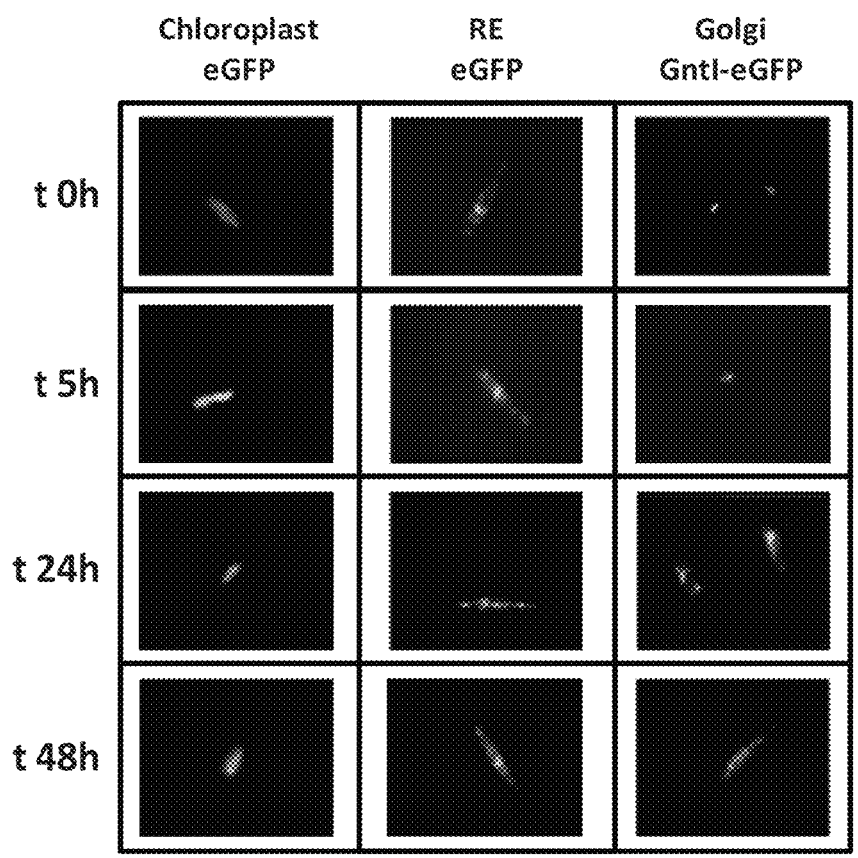

The FIG. 10 shows the fluorescence observed in the Chloroplast and Endoplasmic Reticulum of *P. tricornutum* microalgae which express the eGFP protein and the fluorescence observed in the Golgi apparatus of microalgae expressing GnT I-eGFP, after a culture of said microalgae in brefeldin A (an agent capable of dismantling the structure of the Golgi apparatus by blocking the transport from the Endoplasmic Reticulum to the Golgi apparatus).

Figure 11:
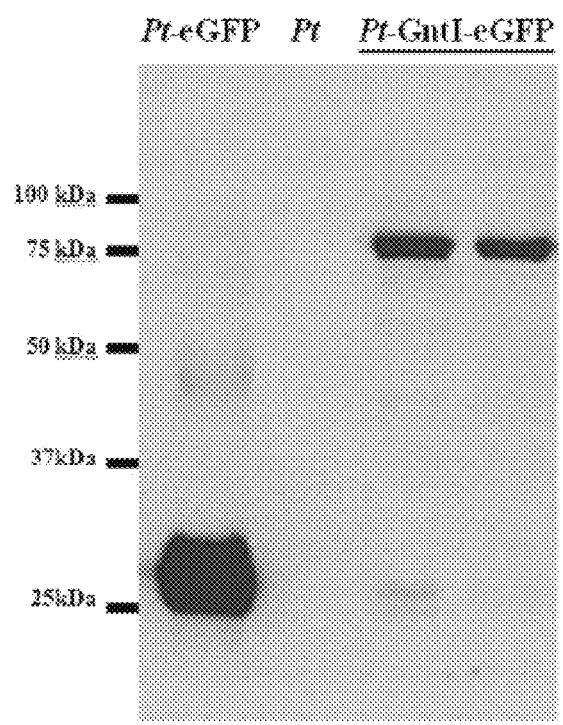

The FIG. 11 shows the detection of the GnT I-eGFP fusion protein by Western Blot. The Pt-eGFP sample corresponds to a protein extract from *P. tricornutum* which produce cytosolic eGFP protein. The negative sample (Pt) corresponds to protein extract from a non-transformed *P. tricornutum* microalga. Finally, the Pt-GnT I-eGFP correspond to protein extracts from two *P. tricornutum* clones which were transformed with a sequence coding for the GnT I-eGFP fusion protein and presenting fluorescence at the Golgi apparatus.

The FIG. 12 shows the constructs used for the expression of GnT I in *P. tricornutum*.

Figure 13A:
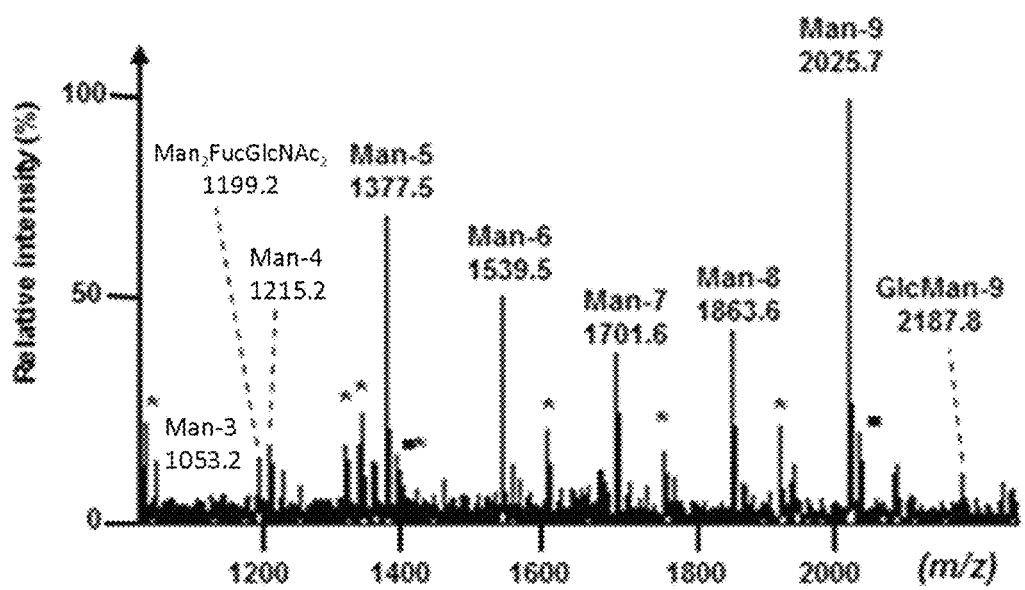
Figure 13B:
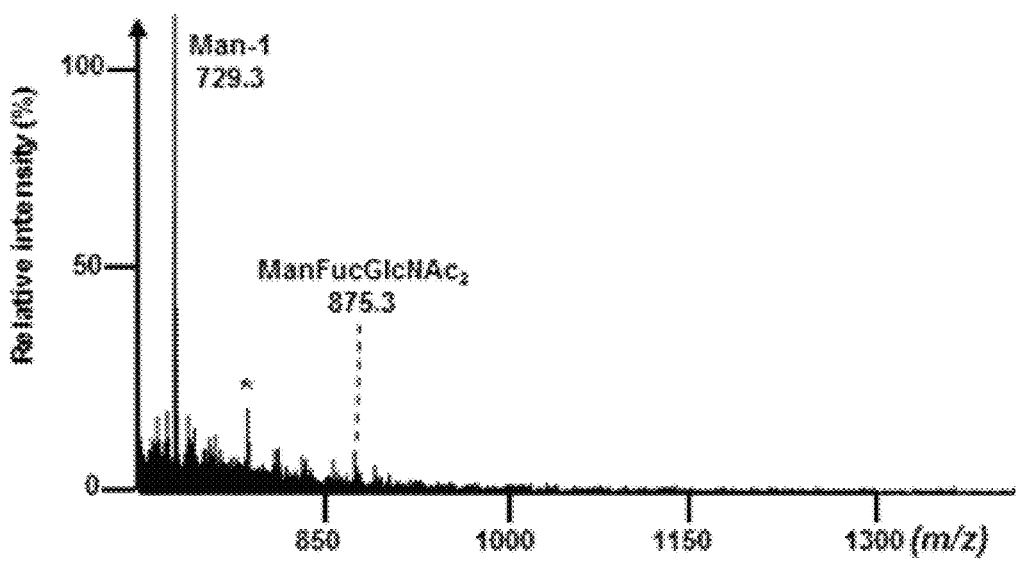
Figure 13C:
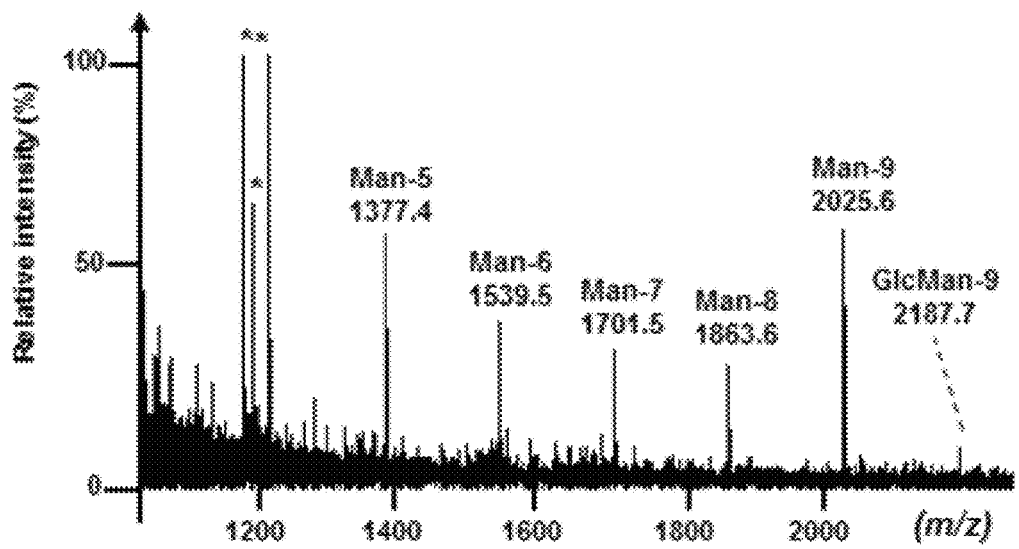

The FIG. 13 shows High mannose-type N-glycans are the main oligosaccharides N-linked to *P. tricornutum* proteins. (A) MALDI-TOF mass spectrum of N-linked glycans released by PNGase A from glycoproteins of *P. tricornutum* and labelled with 2-aminobenzamide (2-AB). (B) MALDI-TOF mass spectrum of the pool of N-glycans after treatment with Jack bean α-mannosidase. (C) MALDI-TOF mass spectrum of 2-AB-labelled N-linked glycans released by PNGase F from glycoproteins of *P. tricornutum*. Man-3 to Man-9: paucimannose and high mannose-type N-glycans $Man_3GlcNAc_2$ to $Man_9GlcNAc_2$. *: contaminants. ■: potassium adducts.

Figure 14A:
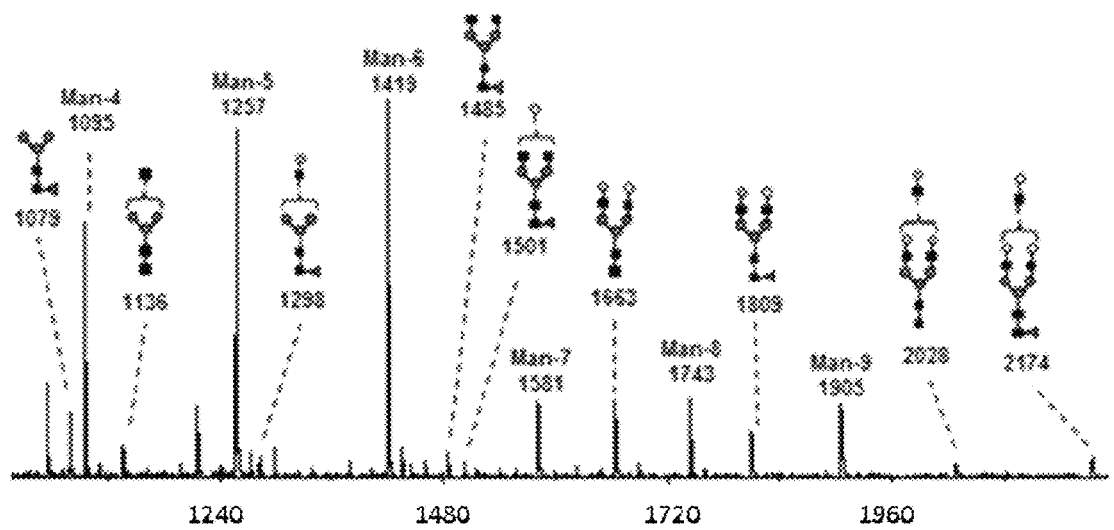
Figure 14B:
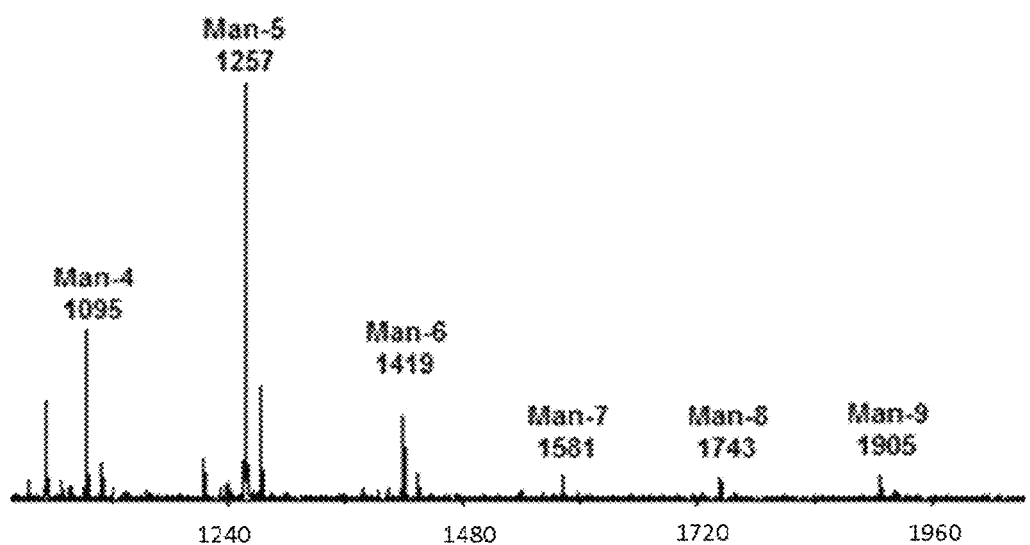
Figure 14C:
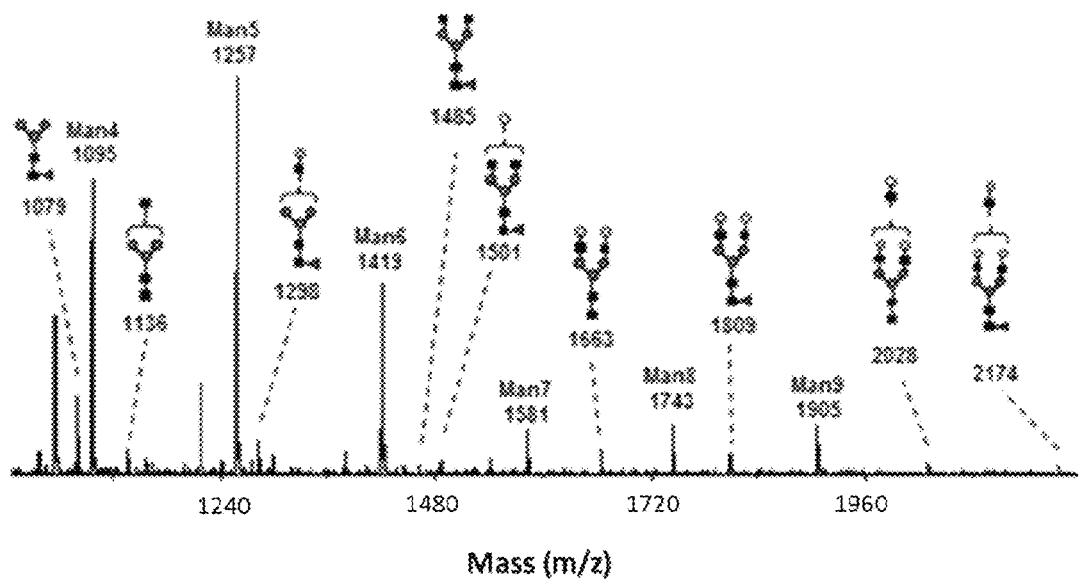

The FIG. 14 shows *P. tricornutum* GnT I complements N-glycan maturation deficiency in CHO Lec1 mutant. MALDI-TOF mass spectra of glycans N-linked to proteins extracted from CHO cells. (A) wild-type, (B) CHO Lec1 mutant and (C) transformant 4 of CHO Lec1 mutant complemented with *P. tricornutum* GnT I gene. Man-4 to Man-9: high mannose-type N-glycans $Man_4GlcNAc_2$ to $Man_9GlcNAc_2$. Symbols (70): black square with black outline: GlcNAc, grey circle with black outline: Man, white circle with black outline: Gal, grey triangle with black outline: Fucose.

SUMMARY OF THE INVENTION

A first aspect of the invention concerns a transformed *Phaeodactylum tricornutum* whose N-glycosylation pathway has been modified by the inactivation of at least one β-N-acetylglucosaminidase and/or the expression of at least one glycosylation enzyme encoded by a nucleic acid sequence operatively linked to a promoter, wherein
  (i) said nucleic acid sequence encodes an N-acetylglucosaminyltransferase I having the amino acid sequence SEQ ID No1, a fragment or a derivative thereof and said operatively linked promoter has a sequence identity of less 50% with SEQ ID No3 or a fragment thereof, and/or
  (ii) said nucleic acid sequence encodes an α-Mannosidase II having the amino acid sequence SEQ ID No5, a fragment or a derivative thereof and said operatively linked promoter has a sequence identity of less 50% with SEQ ID No7 or a fragment thereof.

In a preferred embodiment, said *P. Tricornutum* further comprises another nucleic acid sequence operatively linked to a promoter, said other nucleic acid sequence encoding a polypeptide that is expressed and glycosylated in the transformed *P. tricornutum*.

A second aspect of the invention concerns a method for producing a glycosylated polypeptide, said method comprising the steps of
  (i) Culturing a transformed *P. tricornutum* as disclosed previously,
  (ii) Purifying said polypeptide that is expressed and glycosylated in said transformed *P. tricornutum*.

In a preferred embodiment, said method comprises a further step (iii) of determining the glycosylation pattern of said polypeptide.

A third aspect of the invention concerns a use of a transformed *P. tricornutum* as disclosed previously for producing a glycosylated polypeptide.

DETAILED DESCRIPTION OF THE INVENTION

A gene encoding a putative N-acetylglucosaminyltransferase I (GnT I) has been predicted in the *Phaeodactylum tricornutum* (*P. tricornutum*) genome, but the inventors established that this putative GnT I does not exhibit any significant activity in *Phaeodactylum tricornutum* under standard culture conditions, as proteins extracted from

*Phaeodactylum tricornutum* did not exhibit any GlcNAcMan5GlcNAc2 glycosylation pattern and carry about 95-97% of high-mannose-type N-glycans ranging from $Man_9GlcNAc_2$ (Man-9) to $Man_5GlcNAc_2$ (Man-5).

However, the inventors surprisingly found in further experiments, presented in the following examples, that this putative GnT I was able to restore the maturation of N-linked glycans into complex-type N-glycans in CHO Lec1 mutants, defective in their endogenous GnT I.

Consequently, the inventors show that this putative GnT I has an enzymatic activity, which enzymatic activity can restore defective mammalian GnT I activity.

Moreover, The N-acetylglucosaminyltransferase I is not the only enzyme identified in the genome of *Phaeodactylum tricornutum* by the inventors. A further gene encoding an alpha-Mannosidase II (α-Man II) has been identified in the genome of *Phaeodactylum tricornutum*, whereas there was no detectable of α-Man II activity in *P. tricornutum* under standard culture conditions.

$GlcNAcMan_5GlcNAc_2$, the product of GnT I, is successively converted in the Golgi apparatus into $GlcNAcMan_4GlcNAc_2$ and then $GlcNAcMan_3GlcNAc_2$ by the action of the α-Man II, followed by the production of $GlcNAc_2Man_3GlcNAc_2$ under the action of GnT II.

Nevertheless, some organisms express β-N-acetylglucosaminidases, which are enzymes responsible for the degradation of GlcNAc-terminated N-glycans after their biosynthesis in the Golgi apparatus with the action of GnT I and Man II. Elimination of terminal GlcNAc by β-N-acetylglucosaminidases in the secretory system or in compartments where proteins accumulate can then convert these oligosaccharides into $Man_4GlcNAc_2$ and $Man_3GlcNAc_2$, thus annealing the Glycosylation pathway.

The inventors identified genes encoding putative β-N-acetylglucosaminidases in the genome of *Phaeodactylum tricornutum*: a first β-N-acetylglucosaminidase of amino acid sequence SEQ ID No9 is encoded by the nucleic acid sequence SEQ ID No10 (Accession number 45073), whereas a second β-N-acetylglucosaminidase of amino acid sequence SEQ ID No11 is encoded by the nucleic acid sequence SEQ ID No12 (Accession number 49563).

These putative genes may explain the absence of the detectable amount of $GlcNAcMan_5GlcNAc_2$, the product of GnT I, or $GlcNAcMan_4GlcNAc_2$ and $GlcNAcMan_3GlcNAc_2$, products of GnT I and α-Man II, on *P. tricornutum* proteins.

Therefore, a first object of the invention is a transformed *Phaeodactylum tricornutum* whose N-glycosylation pathway has been modified by the inactivation of at least one β-N-acetylglucosaminidase and/or the expression of at least one glycosylation enzyme encoded by a nucleic acid sequence operatively linked to a promoter, wherein
  (i) said nucleic acid sequence encodes an N-acetylglucosaminyltransferase I having the amino acid sequence SEQ ID No1, a fragment or a derivative thereof and said operatively linked promoter has a sequence identity of less 50% with SEQ ID No3 or a fragment thereof, and/or
  (ii) said nucleic acid sequence encodes an α-Mannosidase II having the amino acid sequence SEQ ID No5, a fragment or a derivative thereof and said operatively linked promoter has a sequence identity of less 50% with SEQ ID No7 or a fragment thereof.

In a first embodiment, said transformed *Phaeodactylum tricornutum* comprises a nucleic acid sequence operatively linked to a promoter, wherein:
  (i) said nucleic acid sequence encodes an N-acetylglucosaminyltransferase I having the amino acid sequence SEQ ID no1, a fragment or a derivative thereof; and
  (ii) said operatively linked promoter has a sequence identity of less 50% with SEQ ID no3 or a fragment thereof.

*Phaeodactylum tricornutum* is a microalga which belongs to the Bacillariophyceae class, to the Naviculales order, to the Phaeodactylaceae family and to the *Phaeodactylum* genus.

The term "nucleic acid sequence" used herein refers to DNA sequences (e.g., cDNA or genomic or synthetic DNA), as well as analogs of DNA containing non-natural nucleotide analogs, non-native internucleoside bonds, or both. Preferably, said nucleic acid sequence is a DNA sequence. This nucleic acid sequence can be in any topological conformation, like linear or circular.

The expression "Operatively linked" promoter refers to a linkage in which the promoter is contiguous with the gene of interest to control the expression of said gene.

The expression "fragment" with reference to SEQ ID No3 refers to a nucleic acid sequence of at least 100 nucleic acids of said SEQ ID No3, preferably of at least 150 nucleic acids of SEQ ID No3, most preferably of at least 200 nucleic acids of SEQ ID No3.

The term "transformed *Phaeodactylum tricornutum*" refers to a *P. tricornutum* wherein the nucleic acid sequence operatively linked to a promoter has been introduced in said microalgae by conventional methods of transformation, as described below, so as to express said nucleic acid molecule in the nucleus of said *P. tricornutum*.

Transformation of *P. tricornutum* can be carried out by conventional methods such as microparticles bombardment, electroporation, glass beads, polyethylene glycol (PEG), silicon carbide whiskers, or use of viruses or *agrobacterium*. Such a protocol is disclosed in the examples. The nucleic acid sequence may be introduced into *Phaeodactylum tricornutum* via a plasmid, virus sequences, double or simple strand DNA, circular or linear DNA. It is generally desirable to include into each nucleic acid sequence or vector at least one selectable marker to allow selection of *Phaeodactylum tricornutum* that have been stably transformed. Examples of such markers are antibiotic resistant genes such as sh ble gene enabling resistance to zeocin, nat or sat-1 genes enabling resistance to nourseothricin, bar gene enabling resistance to glufosinate.

N-acetylglucosaminyltransferase I, also known as GnT I or mannoside acetylglucosaminyltransferase I (MGAT I) is an enzyme from the N-glycosylation pathway, which is capable of adding an N-acetylglucosamine (GlcNAc) residue to $Man_5GlcNAc_2$ to produce a $GlcNAcMan_5GlcNAc_2$.

The N-acetylglucosaminyltransferase I having the amino acid sequence SEQ ID No1 corresponds to the "endogenous N-acetylglucosaminyltransferase" encoded by the nucleic acid sequence SEQ ID No2 present in the genome of wild-type *Phaeodactylum tricornutum*.

The expression "fragment" with reference to SEQ ID No1 refers to an amino acid sequence comprising at least SEQ ID No4 corresponding to the amino acid sequence of the catalytic site of N-acetylglucosaminyltransferase I having said SEQ ID No1.

The expression "catalytic site" refers to the amino acid sequence of an enzyme, said amino acid sequence being responsible for the enzymatic activity. Therefore, the catalytic site of the N-acetylglucosaminyltransferase I according to the invention corresponds to the amino acid sequence responsible for the addition of an N-acetylglucosamine (GlcNAc) residue to Man$_5$GlcNAc$_2$ to produce a GlcNAcMan$_5$GlcNAc$_2$.

As used herein the term "N-acetylglucosaminyltransferase I derivative" refers to an amino acid sequence capable of adding an N-acetylglucosamine (GlcNAc) residue to Man$_5$GlcNAc$_2$ to produce a GlcNAcMan$_5$GlcNAc$_2$ and having more than 85% of identity with amino acid sequence SEQ ID No1 or a fragment thereof, preferably more than 90% of identity with amino acid sequence SEQ ID No1 or a fragment thereof, and more preferably more than 95% of identity with amino acid sequence SEQ ID No1 or a fragment thereof.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously align according to the best alignment; this comparison is realized on segments of comparison in order to identify and compared the local regions of similarity. The best sequences alignment to perform comparison can be realized by using computer softwares using such algorithms (GAP, BESTFIT, BLAST P, BLAST N, FASTA, TFASTA in the Wisconsin Genetics software Package). To get the best local alignment, one can preferably used BLAST software, with the BLOSUM 62 matrix, or the PAM 30 matrix. The identity percentage between two sequences of amino acids is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

Many different promoters allowing the expression of a nucleic acid sequence in *Phaeodactylum tricornutum* are known from the skilled person. As an example of such promoters, one can cite the nuclear promoters such fcpA and fcpB from *Phaeodactylum tricornutum* disclosed in ZAVLASKAÏA et al. (*J. Phycol.*, vol. 36, p: 379-386, 2000). Nevertheless, this promoter has a sequence identity of less 50% with SEQ ID no3 corresponding to the sequence of 1047 pb nucleic acid sequence upstream of the ATG of nucleic acid sequence SEQ ID No2 present in the genome of wild-type *Phaeodactylum tricornutum*, preferably of less than 25% and most preferably of less than 10%.

In another preferred embodiment, said transformed *Phaeodactylum tricornutum* further comprises a nucleic acid sequence operatively linked to a promoter, wherein:
  (i) said nucleic acid sequence encodes an alpha-Mannosidase II having the amino acid sequence SEQ ID no5, a fragment or a derivative thereof; and
  (ii) said operatively linked promoter has a sequence identity of less 50% with SEQ ID no 7 or a fragment thereof.

In a second embodiment, said transformed *Phaeodactylum tricornutum* comprises a nucleic acid sequence operatively linked to a promoter, wherein:
  (i) said nucleic acid sequence encodes an alpha-Mannosidase II having the amino acid sequence SEQ ID no5, a fragment or a derivative thereof; and
  (ii) said operatively linked promoter has a sequence identity of less 50% with SEQ ID no 7 or a fragment thereof.

The expression "fragment" with reference to SEQ ID No7 refers to a nucleic acid sequence of at least 100 nucleic acids of said SEQ ID No7, preferably of at least 150 nucleic acids of SEQ ID No7, most preferably of at least 200 nucleic acids of SEQ ID No7.

α-Mannosidase II, also known as α-Man II, is an enzyme which catalyzes the first committed step in the biosynthesis of complex N-glycans. α-Man II is capable of hydrolysing the terminal (1→3)- and (1→6)-linked alpha-D-mannose residues in the mannosyl-oligosaccharide GlcNAcMan$_5$GlcNAc$_2$. GlcNAcMan$_5$GlcNAc$_2$, the product of GnT I, is successively converted in the Golgi apparatus into GlcNAcMan$_4$GlcNAc$_2$ and then GlcNAcMan$_3$GlcNAc$_2$ by action of the α-Man II.

The α-Mannosidase II having the amino acid sequence SEQ ID No5 corresponds to the "endogenous α-Mannosidase II" encoded by the nucleic acid sequence SEQ ID No6 present in the genome of wild-type *Phaeodactylum tricornutum*.

The expression "fragment" with reference to SEQ ID No5 refers to an amino acid sequence of at least SEQ ID No8 corresponding to the amino acid sequence of the luminal part of α-Man II, which comprises the catalytic site of α-Man II.

The expression "catalytic site" refers to the amino acid sequence of an enzyme, said amino acid sequence being responsible for the enzymatic activity. Therefore, the catalytic site of the α-Mannosidase II according to the invention corresponds to the amino acid sequence responsible for the conversion of GlcNAcMan$_5$GlcNAc$_2$, the product of GnT I, in the Golgi apparatus into GlcNAcMan$_4$GlcNAc$_2$ and then GlcNAcMan$_3$GlcNAc$_2$.

As used herein the term "α-Man II derivative" refers to an amino acid sequence capable of converting GlcNAcMan$_5$GlcNAc$_2$, the product of GnT I, in the Golgi apparatus into GlcNAcMan$_4$GlcNAc$_2$ and then GlcNAcMan$_3$GlcNAc$_2$ and having more than 85% of identity with amino acid sequence SEQ ID No5 or a fragment thereof, preferably more than 90% of identity with amino acid sequence SEQ ID No5 or a fragment thereof, and more preferably more than 95% of identity with amino acid sequence SEQ ID No5 or a fragment thereof.

Many different promoters allowing the expression of a nucleic acid sequence in *Phaeodactylum tricornutum* are known from the skilled person. As an example of such promoters, one can cite the nuclear promoters such fcpA and fcpB from *Phaeodactylum tricornutum* disclosed in ZAVLASKAÏA et al. (*J Phycol.*, vol. 36, p: 379-386, 2000). Nevertheless, this promoter has a sequence identity of less 50% with SEQ ID no7 corresponding to the sequence of 1000 pb nucleic acid sequence upstream of the ATG of nucleic acid sequence SEQ ID No6 present in the genome of wild-type *Phaeodactylum tricornutum*, preferably of less than 25% and most preferably of less than 10%.

In a third embodiment, said transformed *Phaeodactylum tricornutum* has at least one β-N-acetylglucosaminidase which has been inactivated, preferably said at least one β-N-acetylglucosaminidase being a β-N-acetylglucosaminidase of amino acid sequence SEQ ID No9 or a β-N-acetylglucosaminidase of amino acid sequence of SEQ ID No11.

In a preferred embodiment, both β-N-acetylglucosaminidases of amino acid sequences SEQ ID No9 and SEQ ID No11 have been inactivated.

The term "inactivated" with reference to β-N-acetylglucosaminidases refers to β-N-acetylglucosaminidases which do not present any enzymatic activity.

This type of enzyme is able to hydrolyze exclusively the GlcNAc residue attached to the α-1,3/1,6-linked mannose of the core pentasaccharide of N-glycans. It is noteworthy that this enzyme could not hydrolyze $Man_5GlcNAc$, but acted only further "downstream" on $GlcNAcMan_5GlcNAc_2$, $GlcNAcMan_4GlcNAc_2$, $GlcNAcMan_3GlcNAc_2$ or $GlcNAcMan_3GlcNAc_2$ substituted by fucose residues linked to the proximal GlcNAc.

By β-N-acetylglucosaminidase enzymatic activities, we mean the removal of the terminal GlcNAc residue linked to the mannoses of the core of complex-type glycans N-linked to proteins.

Such inactivation can be obtained by several ways known from the person skilled in the art. For example, methods of inactivation comprise gene silencing with RNA interference (miRNA, siRNA) which have been used in microalgae (Zhao T. et al 2009, The Plant Journal, vol. 58, p: 157-164; Molnar A. and al., 2009, The Plant Journal vol. 58, p: 165-174), as in *P. tricornutum* (De Riso V. et al., 2009, Nucleic Acids Research, p: 1-12). The inactivation of said β-N-acetylglucosaminidases can also be obtained by the knock out of the corresponding genes but also by the use of a method of inhibition of the enzymatic activity, for example by using antibody directed to the catalytic site of said β-N-acetylglucosaminidases.

The inactivation of β-N-acetylglucosaminidases can be confirmed by testing their enzymatic activity, which can be measured by techniques which are known from the skilled person in the art, for example by using one of the two different following tests of activity described in Léonard R. et al., 2006, The Journal of Biological Chemistry, Vol. 281, p: 4867-4875.

According to a first test, N-acetylglucosaminidases are incubated with the different substrates at 37° C. for 1-20 h. For experiments with p-nitrophenyl-GlcNAc, the substrate concentration is 5 mM in a total volume of 0.04 ml of 0.1 M citrate/phosphate buffer at pH 3-8. The reactions are terminated by the addition of 0.26 ml of 0.4 M glycine/NaOH buffer at pH 10.4, and absorbance at 405 nm is measured with a microtiter plate reader.

According to a second test, Pyridylaminated oligosaccharides are used at a final concentration of 0.1 mM in a total volume of 0.02 ml of 0.1 M citrate/phosphate buffer at pH 3-8. Incubation is terminated by the addition of 0.18 ml of 20 mM ice-cold sodium borate. Aliquots of 0.05 ml are analyzed by reverse-phase HPLC as described previously.

As used herein, a "transformed" *Phaeodactylum tricornutum* may also correspond to a *P. tricornutum*, wherein at least one β-N-acetylglucosaminidase has been inactivated.

In a preferred embodiment, said β-N-acetylglucosaminidases have been inactivated with the technique of RNA interference.

In a preferred embodiment, said transformed *Phaeodactylum tricornutum* having at least one β-N-acetylglucosaminidase which has been inactivated further comprises a nucleic acid sequence operatively linked to a promoter, wherein (i) said nucleic acid sequence encodes an N-acetylglucosaminyltransferase I having the amino acid sequence SEQ ID No1, a fragment or a derivative thereof, and (ii) said operatively linked promoter has a sequence identity of less 50% with SEQ ID No3 or a fragment thereof.

In another preferred embodiment, said transformed *Phaeodactylum tricornutum* having at least one β-N-acetylglucosaminidase which has been inactivated as disclosed previously further comprises a nucleic acid sequence operatively linked to a promoter, wherein (iii) said nucleic acid sequence encodes an α-Mannosidase II having the amino acid sequence SEQ ID No5, a fragment or a derivative thereof, and (iv) said operatively linked promoter has a sequence identity of less 50% with SEQ ID No7 or a fragment thereof.

Preferably, all the transformed *P. tricornutum* as described previously further comprises a further nucleic acid sequence operatively linked to a promoter, said further nucleic acid sequence encoding a polypeptide that is expressed and glycosylated in the transformed *P. tricornutum*.

The term "polypeptide" as used herein refers to an amino acid sequence comprising more than 50 amino acids which are linked by peptide bonds.

After transformation of *P. tricornutum*, transformants producing the desired polypeptide are selected. Selection can be carried out by one or more conventional methods comprising: enzyme-linked immunosorbent assay (ELISA), mass spectroscopy such as MALDI-TOF-MS, ESI-MS chromatography, characterization of cells using fluorescence activated cell sorter, spectrophotometer, fluorimeter, immunocytochemistry by exposing cells to an antibody having a specific affinity for the desired protein. Such methods are detailed in examples below.

The glycosylated polypeptides have at least one $GlcNAcMan_5GlcNAc_2$ structure. Preferably, said glycosylated polypeptides have at least one $GlcNAcMan_4GlcNAc_2$, $GlcNAcMan_3GlcNAc_2$ or $GlcNAc_2Man_3GlcNAc_2$.

Advantageously, the polypeptide expressed and glycosylated by the transformed *Phaeodactylum tricornutum* is a polypeptide of animal origin, preferably of mammalian origin, and most preferably of human origin.

In a still preferred embodiment, the polypeptide expressed and glycosylated by the transformed *P. tricornutum* of the invention is a polypeptide having a therapeutic interest. Preferably, said polypeptide is selected in the group comprising erythropoietin, cytokines such as interferons, antibodies and their fragments, coagulation factors, hormones, beta-glucocerebrosidase, pentraxin-3, anti-TNFs, acid α-glucosidase, α-L-iduronidase and derivatives thereof.

An antibody is an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively. Each heavy chain is comprised of a N-term heavy chain variable region (abbreviated herein as HCVR) and a heavy chain constant region. The heavy chain constant region is comprised of three domains (CH1, CH2, and CH3) for IgG, IgD, and IgA; and 4 domains (CH1, CH2, CH3, and CH4) for IgM and IgE. Each light chain is comprised of a N-term light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions. The functional ability of the antibody to bind a particular antigen depends on the variable regions of each light/heavy chain pair, and is largely determined by the CDRs.

The term "antibody", as used herein, refers to a monoclonal antibody per se. A monoclonal antibody can be a human antibody, chimeric antibody and/or humanized antibody.

The term "antibody fragments" as used herein refers to antibody fragments that bind to the particular antigens of said antibody. For example, antibody fragments capable of binding to particular antigens include Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or ScFv (e.g., by molecular biology techniques) fragments, are encompassed by the invention.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

The term "Cytokines" refers to signalling proteins which are released by specific cells of the immune system to carry a signal to other cells in order to alter their function. Cytokines are immunomodulating agents and are extensively used in cellular communication. The term cytokines encompasses a wide range of polypeptide regulators, such as interferons, interleukins, chemokins or Tumor Necrosis Factor.

The term "Coagulation factors" refers to the plasma proteins which interact with platelets in a complex cascade of enzyme-catalyzed reactions, leading to the formation of fibrin for the initiation of a blood clot in the blood coagulation process. Coagulation factors, at the number of 13, are generally serine proteases, but also comprise glycoproteins (Factors VIII and V) or others types of enzyme, such as transglutaminase (Factor XIII).

The term "Hormones" refers to chemical messengers secreted by specific cells in the plasma or the lymph to produce their effects on other cells of the organism at a distance from their production sites. Most hormones initiate a cellular response by initially combining with either a specific intracellular or cell membrane associated receptor protein. Common known hormones are, for example, insulin for the regulation of energy and glucose in the organism, or the Growth Hormone which stimulates growth and cell reproduction and regeneration.

In another preferred embodiment, the invention relates to a transformed *P. tricornutum* as described above, further comprising another nucleic acid sequence operatively linked to a promoter, wherein said nucleic acid sequence encodes an N-acetylglucosaminyltransferase II, a fragment or a derivative thereof.

N-acetylglucosaminyltransferase II, also known as GnT II or mannoside acetylglucosaminyltransferase II (MGAT II) is an enzyme from the N-glycosylation pathway, which is capable of adding an N-acetylglucosamine (GlcNAc) residue to GlcNAcMan$_3$GlcNAc$_2$, product of α-Man II, to produce a GlcNAc$_2$Man$_3$GlcNAc$_2$ Examples of GnT II, also known as mannosyl (alpha-1, 6-)-glycoprotein beta-1,2-N-acetylglucosaminyltransferase (MGAT 2), include GnT II from *Mus musculus* (SEQ ID No13. Accession number NP_666147), from *Homo sapiens* (SEQ ID No14, Accession number NP_002399) or from *Phaeodactylum tricornutum* (SEQ ID No5).

Preferably, N-acetylglucosaminyltransferase I 1 has an amino acid sequence of SEQ ID No5, a fragment or a derivative thereof and said operatively linked promoter has a sequence identity of less 50% with SEQ ID No7 or a fragment thereof.

In still another preferred embodiment, said N-acetylglucosaminyltransferase II comprises the amino acid sequence SEQ ID No15 and said operatively linked promoter has a sequence identity of less 50% with SEQ ID no 7 or a fragment thereof.

Inventors have noticed that α-Mannosidase II have an N-acetylglucosaminyltransferase II domain of amino acid sequence SEQ ID No15.

The expression "fragment" with reference to SEQ ID No5 and GnT II refers to an amino acid sequence of at least SEQ ID No15 corresponding to the amino acid sequence of the GnT II domain of α-Mannosidase II.

The expression "catalytic site" refers to the amino acid sequence of an enzyme, said amino acid sequence being responsible for the enzymatic activity. Therefore, the catalytic site of the GnT II according to the invention corresponds to the amino acid sequence responsible for the addition of an N-acetylglucosamine (GlcNAc) residue to GlcNAcMan$_3$GlcNAc$_2$ to produce a GlcNAc$_2$Man$_3$GlcNAc$_2$.

As used herein the term "GnT II derivative" refers to an amino acid sequence capable of adding an N-acetylglucosamine (GlcNAc) residue to GlcNAcMan$_3$GlcNAc$_2$, product of α-Man II, to produce a GlcNAc$_2$Man$_3$GlcNAc$_2$ and having more than 85% of identity with the amino acid sequence SEQ ID No5 or a fragment thereof, preferably more than 90% of identity with amino acid sequence SEQ ID No5 or a fragment thereof, and more preferably more than 95% of identity with amino acid sequence SEQ ID No5 or a fragment thereof.

In another preferred embodiment, the invention relates to a transformed *P. tricornutum* as described above, further comprising another nucleic acid sequence operatively linked to a promoter, said nucleic acid sequence encoding at least an enzyme of the human N-glycosylation pathway such as N-acetylglucosaminyltransferases III, IV, V, VI, and glycosyltransferases such as galactosyltransferases, fucosyltransferases or sialyltransferases. Said enzymes are expressed in said transformed *P. tricornutum* and enable the N-glycosylation of a polypeptide.

In another preferred embodiment, said transformed *P. tricornutum* as described above, further comprising another nucleic acid sequence operatively linked to a promoter comprises a nucleic acid sequence encoding N-acetylglucosaminyltransferases III, IV, V and VI.

In still another preferred embodiment said transformed *P. tricornutum* as described above, further comprising another nucleic acid sequence operatively linked to a promoter comprises a nucleic acid sequence encoding glycosyltransferases comprising galactosyltransferases, fucosyltransferases and sialyltransferases.

GnT III, GnT IV, GnT V, GnT VI, fucosyltransferase, galactosyltransferase (GalT) and sialyltransferases (ST) are well known from one of skilled in the art.

Examples of GnT III, also known as mannosyl (beta-1, 4-)-glycoprotein beta-1,4-N-acetylglucosaminyltransferase (MGAT 3), include GnT III from *Mus musculus* (SEQ ID No17, Accession number NP_034925) or from *Homo sapiens* (SEQ ID No18, Accession number NP_002400). Preferably, said N-acetylglucosaminyltransferase III (GnT III) corresponds to SEQ ID No18 (Accession number NP_02400).

Examples of GnT IV, also known as mannosyl (alpha-1, 3-)-glycoprotein beta-1,4-N-acetylglucosaminyltransferase (MGAT4), include GnT IV isozyme A from *Mus musculus* (SEQ ID No19, Accession number NP_776295), isozyme B from *Mus musculus* (SEQ ID No20, Accession number NP_666038), isozyme C from *Mus musculus* (SEQ ID No21, Accession number NP_080519), GnT IV isozyme A from *Homo sapiens* (SEQ ID No22, Accession number NP_036346), GnT IV isozyme B from *Homo sapiens* (isoform 1, SEQ ID 23, Accession number NP_055090 or isoform 2, SEQ ID No24, Accession number NP_463459) or GnT IV isozyme C from *Homo sapiens* (SEQ ID No25, Accession number NP_037376).

Examples of GnT V, include GnT V from *Mus musculus* (SEQ ID No26, Accession number NP_660110), GnT V isozyme B from *Mus musculus* (SEQ ID No27, Accession number NP_766536), GnT V from *Homo sapiens* (SEQ ID No28, Accession number NP 002401), GnT V isozyme B from *Homo sapiens* (isoform 1, SEQ ID No29, Accession number NP_653278 or isoform 2, SEQ ID No30, Accession number NP_945193).

Example of GnT VI includes GnT VI from *Gallus gallus* (SEQ ID No31, Accession number NP_990012).

Fucosyltransferases are well known from the skilled person and include, as an example alpha (1.6) fucosyltransferase (fucosyltransferase 8 (FUT8)), like FUT8 from *Mus musculus* (SEQ ID No32, Accession number NP_058589) or FUT8 from *Homo sapiens* (SEQ ID No33, Accession number Q9BYC5). Preferably, said fucosyltransferase corresponds to SEQ ID No33 (Accession number Q9BYC5).

Galactosyltransferase are well known from the skilled person and include, as an example, one beta-(1,4)-galactosyltransferase (B4GALT1), like B4GALT1 from *Homo sapiens* (SEQ ID No34, Accession number. NP_001488), or B4GALT1 from *Mus musculus* (SEQ ID No35, Accession number CAM14782). Preferably, said galactosyltransferase corresponds to SEQ ID No34 (Accession number NP_001488).

Sialyltransferase are well known from the skilled person and include, as an example Alpha 2,6 Sialyltransferase (ST6 beta-galactosamide alpha-2,6-sialyltranferase 1 (ST6GAL1) or beta galactoside alpha 2,6 sialyltransferase 2 (ST6GAL2)), like ST6GAL2 from *Mus musculus* (SEQ ID No36, Accession number NP_766417) or ST6GAL1 from *Homo sapiens* (isoform a, SEQ ID 37, Accession number NP_775323 or isoform b, SEQ ID No38, Accession number NP_775324), or Alpha 2,3 Sialyltransferase (ST3 beta-galactoside alpha-2,3-sialyltransferase 6 (ST3GAL6), ST3 beta-galactoside alpha-2,3-sialyltransferase 1 (ST3GAL1), ST3 beta-galactoside alpha-2,3-sialyltransferase 2 (ST3GAL2), ST3 beta-galactoside alpha-2,3-sialyltransferase 3 (ST3GAL3), like ST3GAL1 from *Mus musculus* (SEQ ID No39, Accession number NP_033203) or from *Homo sapiens* (SEQ ID No40, Accession number NP_003024), ST3GAL2 from *Homo sapiens* (SEQ ID No41 Accession number NP_008858), ST3GAL3 from *Homo sapiens* (isoform a, SEQ ID No42, Accession number NP_777623, isoform b, SEQ ID No43, Accession number NP_777624, isoform c, SEQ ID No44, Accession number NP_777625, isoform f, SEQ ID No45, Accession number NP_777628, isoform j, SEQ ID No46, Accession number NP_006270, isoform d, SEQ ID No47, Accession number NP_777626, isoform e, SEQ ID No48, Accession number NP 777627, isoform i, SEQ ID No49, Accession number NP_777631, isoform g, SEQ ID No50, Accession number NP_777629, isoform h, SEQ ID No51, Accession number NP_777630), or ST3GAL6 from *Homo sapiens* (SEQ ID No52, Accession number NP_006091).

For a glycosyltransferase to function satisfactorily in the Golgi apparatus, it is necessary for the enzyme to be provided with sufficient concentrations of an appropriate nucleotide sugar, which is the high-energy donor of the sugar moiety added to a nascent glycoprotein. In humans, the full range of nucleotide sugar precursors are generally synthesized in the cytosol and transported into the Golgi apparatus, where they are attached to the core oligosaccharide by glycosyltransferases. The Applicant observed in microalgae a sufficient concentration of GlcNAc, mannose, fucose and galactose but not of sialic acid.

Therefore, for a sialyltransferase to function satisfactorily in the Golgi apparatus, it is necessary to express in the microalgae one or more enzymes needed for sialic acid synthesis, its activation and its transport within the Golgi apparatus among UDP-GlcNAc 2-epimerase, GlcNAc 2-epimerase, GlcNAc-6P 2-epimerase, NeuAc synthase. NeuAc-9P synthase, CMP-NeuAc synthase and CMP-sialic acid transporter (see for example works done in plants: Misaki R et al. Biochem Biophys Res Commun. 2006 Jan. 27; 339 (4): 1184-9; Paccalet T et al. Plant Biotechnol J. 2007 January; 5(1): 16-25). Castihlo et al., 2008 and Castilho et al., 2010 as described above).

UDP-GlcNAc 2-epimerase, which is also known as glucosamine (UDP-N-acetyl)-2-epimerase/N-acetylmannosamine kinase (GNE), is well known from the skilled person and include, as an example GNE from *Mus musculus* (SEQ ID No53, Accession number NP_056643) or GNE from *Homo sapiens* (SEQ ID No54, Accession number NP_005467). Preferably, said GNE corresponds to SEQ ID No54 (Accession number NP_005467).

GlcNAc 2-epimerase is well known from the skilled person and includes, as an example, the renin binding protein (RENBP) from *Homo sapiens* (SEQ ID No55, Accession number NP_002901).

NeuAc-9-P synthase, also called N-acetylneuraminic acid synthase (NANS), is well known from the skilled person and include, as an example, NANS from *Homo sapiens* (SEQ ID No56, Accession number NP_061819).

CMP-NeuAc synthase, which is also known as cytidine monophospho-N-acetylneuraminic acid synthetase (CMAS), is well known from the skilled person and include, as an example CMAS from *Mus musculus* (SEQ ID No57, Accession number NP_034038) or from *Homo sapiens* (SEQ ID No58, Accession number NP_061156). Preferably, said CMAS corresponds to SEQ ID No58 (Accession number NP_061156).

CMP-sialic acid transporters are also well known from the skilled person and include, as an example, solute carrier family 35 (CMP-sialic acid transporter), member A1 (SLC35A1) from *Mus musculus* (SEQ ID No59, Accession number NP_036025) or from *Homo sapiens* (SEQ ID No60, Accession number NP_006407). Preferably, said CMP-sialic acid transporter corresponds to SLC35A1 from *Homo sapiens* (SEQ ID No60, Accession number NP_006407).

The added transporter protein conveys a nucleotide sugar from the cytosol into the Golgi apparatus, where the nucleotide sugar may be reacted by the glycosyltransferase, e.g. to elongate an N-glycan. The reaction liberates a nucleoside diphosphate or monophosphate, UDP, GDP, or CMP. As accumulation of a nucleoside diphosphate inhibits the further activity of a glycosyltransferase, it is frequently also desirable to provide an expressed copy of a gene encoding a nucleotide diphosphatase. The diphosphatase (specific for UDP or GDP as appropriate) hydrolyzes the diphosphonucleoside to yield a nucleoside monophosphate and inorganic phosphate. The nucleoside monophosphate does not inhibit the glycosyltransferase and in any case is exported from the Golgi by an endogenous cellular system.

Another object of the invention is a method for producing a glycosylated polypeptide, said method comprising the steps of:
(i) Culturing a transformed *P. tricornutum* as described here above;
(ii) Purifying said polypeptide expressed and glycosylated in said transformed *P. tricornutum*.

In a preferred embodiment, said method for producing a glycosylated polypeptide comprises a former step of transforming a *Phaeodactylum tricornutum* so as to obtain a *P. tricornutum* as defined previously.

Methods which can be employed for the transformation of *P. tricornutum* are described here above. Such transformation, culture of *P. tricornutum* and purification of glycosylated polypeptides are also exemplified below.

Advantageously, the method of the invention further comprises a step (iii) of determining the glycosylation pattern of said polypeptide.

This glycosylation pattern can be determined by method well known from the skilled person. As an example, preliminary informations about N-glycosylation of the recombinant glycoprotein can be obtained by affino- and immunoblotting analysis using specific probes such as lectins (CON A; ECA; SNA; MAA . . . ) and specific N-glycans antibodies (anti-β1,2-xylose; anti-α-1,3-fucose; anti-Neu5Gc, anti-Lewis . . . ). This is made according to FITCHETTE et al., (Methods Mol. Biol., vol. 355, p: 317-342, 2007) and could be completed by deglycosylation assays.

To investigate the detailed N-glycan profile of recombinant protein, N-linked oligosaccharides is then released from the protein in a non specific manner using enzymatic digestion or chemical treatment (FITCHETTE et al., above mentioned, 2007; SEVENO et al., *Anal. Biochem.*, vol. 379(1), p: 66-72, 2008). The resulting mixture of reducing oligosaccharides can be profiled by HPLC and/or mass spectrometry approaches (ESI-MS-MS and MALDI-TOF essentially) (BARDOR et al., *Curr Opin Struct Biol.*, vol. 16 (5), p: 576-583, 2006; SEVENO et al., above mentioned, 2008). These strategies, coupled to exoglycosidase digestion, enable N-glycan identification and quantification (SEVENO et al., above mentioned, 2008).

Another alternative to study N-glycosylation profile of recombinant protein is to work directly on its glycopeptides after protease digestion of the protein, purification and mass spectrometry analysis of the glycopeptides as disclosed in BARDOR et al. (*Plant Biotechnol. J.*, vol. 1 (6), p: 451-462, 2003).

Another object of the invention relates to the use of a transformed *P. tricornutum* as defined previously for producing a glycosylated polypeptide.

In the following, the invention is described in more detail with reference to methods. Yet, no limitation of the invention is intended by the details of the examples. Rather, the invention pertains to any embodiment which comprises details which are not explicitly mentioned in the examples herein, but which the skilled person finds without undue effort.

EXAMPLES

Example 1

No Significant GnT-I Activity was Detected in *Phaeodactylum tricornutum*

Figure 1:
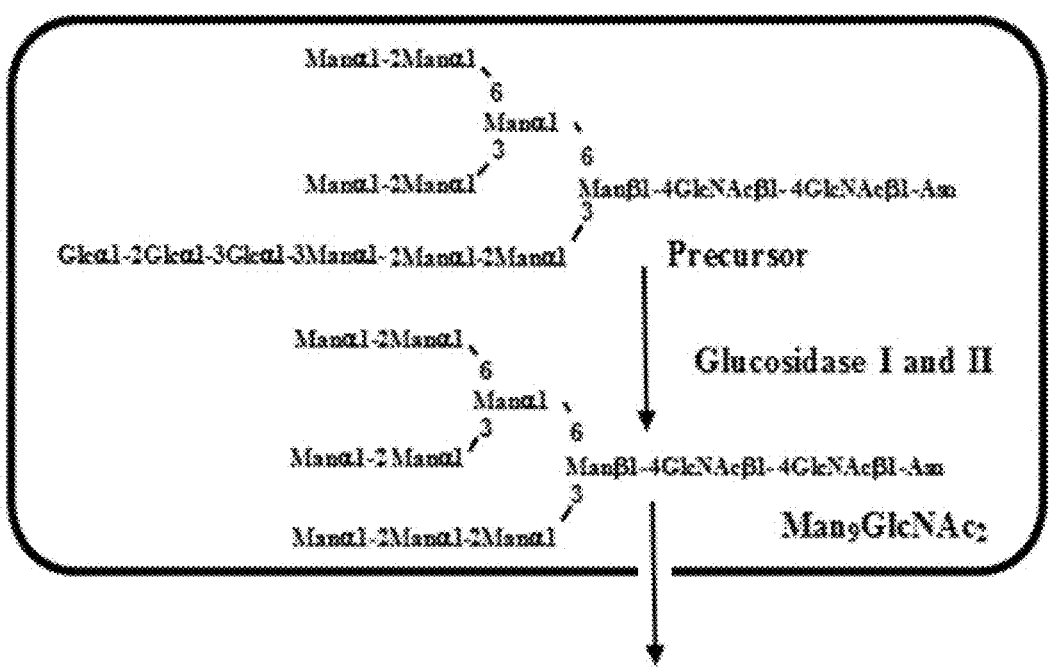
Figure 1:
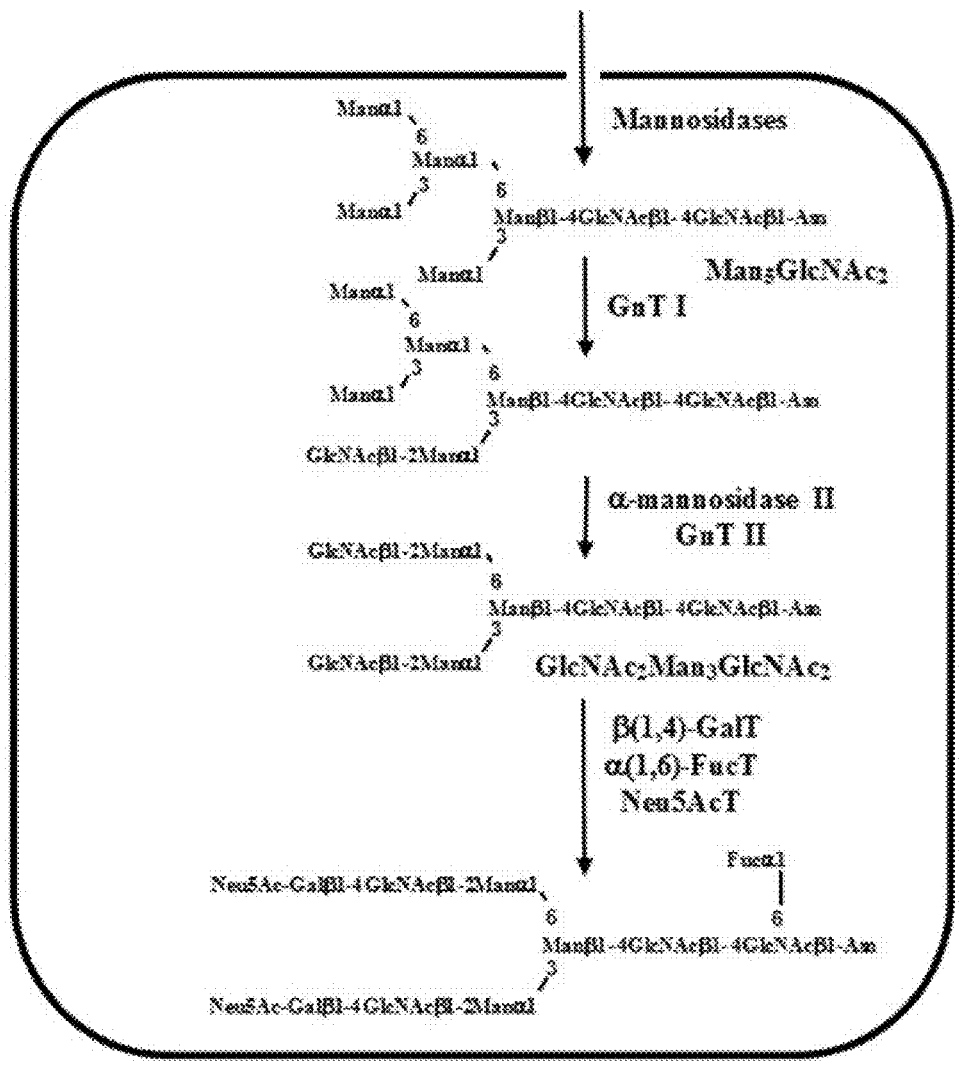

A gene encoding a putative GnT-I was predicted in the *P. tricornutum* genome (Pt54844; http://genome.jgi-psf.org/Phatr2/Phatr2.home.html) (SEQ ID No2). In eukaryotes, this enzyme is involved in the N-glycan maturation into complex-type N-glycan by transfer of a terminal GlcNAc onto Man-5 (FIG. 1). This putative GnT I sequence SEQ ID No2 is predicted to be a type II protein with a luminal part sharing high structural homologies with the catalytic domain of the rabbit GnT I.

In order to determinate if this gene encodes for an active GnT I, the glycosylation pattern of *P. tricornutum* proteins was analyzed.

*Phaeodactylum tricornutum* was cultivated using a standard batch culture method using a scale-up from 2 to 10 L glass carboys in sterilized Conway media (WALNE, L. Fish Invest Serie II, vol. 25(4), p: 1-53, 1966) with seawater (salinity=3.3-3.4%), 1 μm-filtered and aerated with a 2% $CO_2$/air mixture to maintain the pH in a range of 7.5-8.1. Sodium metasilicate was added to the media to the 40 mg/L final concentration.

*Phaeodactylum tricornutum* were grown at 22-23° C. under continuous illumination (280-350 μmol photons $m^2 s^{-1}$). The concentrated culture (about $20 \cdot 10^6$ cells/mL) is first centrifuged at 5,000 g for 20 min at 4° C. and the pellet was then lyophilised.

Two grams of lyophilised microalgae were grind in presence of sand in a mortar using a 750 mM Tris-HCl pH 8 buffer containing 15% (w/v) of sucrose, 2% (v/v) of β-mercaptoethanol and 1 mM phenylmethylsulfonylfluoride and then centrifuged at 4° C. for 30 min at 11,500 g. Proteins from the supernatant were then precipitated with 90% ammonium sulfate during 2 hours at room temperature. The pellet was solubilized in water and then, dialysed against water overnight at 4° C. Finally, the total protein extract was ultra-centrifuged at 100 000 g for 1 hour at 4° C. and resuspended in the smallest volume of water, prior to protein quantification and further analyses. Protein quantification was performed on the total protein extracts from *Phaeodactylum tricornutum* using the BCA protein assay kit from PIERCE according to the manufacturer's instructions.

Structural analysis of glycans N-linked to *P. tricornutum* proteins was then investigated by western-blot analysis on a total protein extract using probes specific for glycan epitopes. For this analysis, 50 μg of total proteins were separated by SDS-PAGE. Onion proteins were used as a control. The separated proteins were transferred onto nitrocellulose membrane and stained with Ponceau Red in order to control transfer efficiency. Affinodetection using concanavalin A was performed by incubation with the lectin at 25 µg·mL$^{-1}$ during 2 h at RT in TBS-T, complemented with 1 mM CaCl$_2$ and 1 mM MgCl$_2$. After washing with TBS-T complemented with CaCl$_2$ and MgCl$_2$ (6 times, 5 minutes), binding of this lectin was detected using horseradish peroxidase diluted at 50 µg·mL$^{-1}$, 1 h at RT in TBS-T complemented with 1 mM CaCl$_2$ and 1 mM MgCl$_2$. After washing with the same TBS-T and then TBS, final development of the blots was performed by using 4-chloro-1-naphtol as previously described (FITCHETTE et al., Methods in Molecular Biology published by Humana Press, USA (Totowa, N.J.), p: 317-342, 2006).

Immunodetection using home-made specific core-β(1,2)-xylose and core-α(1,3)-fucose antibodies (1:1,000 in TBS containing 1% of gelatin, 2 h, RT) was also performed. After washing with TBS-T (6 times, 5 minutes), binding of antibodies was detected using a secondary horseradish peroxidase-conjugated goat anti-rabbit IgG antibody diluted at 1:3,000 in TBS containing 1% gelatin for 90 min at RT (Bio-Rad). Final development of the blots was performed by using 4-chloro 1-naphtol as previously described (FITCHETTE et al., above mentioned, 2006).

Figure 2:
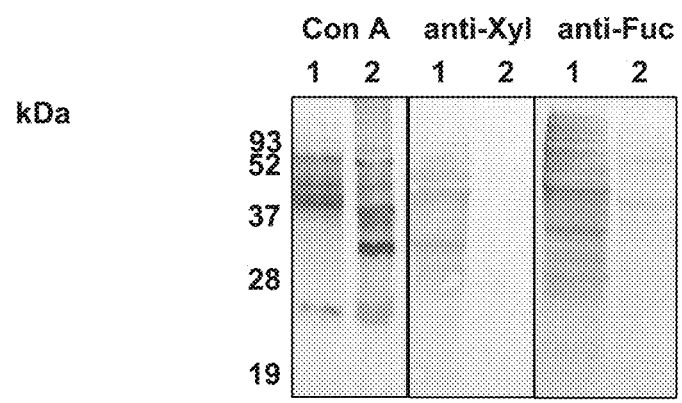

The results are presented in FIG. 2 showing affinodetection using concanavalin A (Con A) and immunodetection using antibodies raised against the core β(1,2)-xylose (anti-Xyl) and core α(1,3)-fucose (anti-Fuc) epitopes of proteins isolated from green onion as a positive control (Lane 1) and from Phaeodactylum tricornutum grown in standard conditions (Lane 2)

The results show that the proteins expressed in Phaeodactylum tricornutum do not exhibit any β(1,2)-xylose (anti-Xyl) and core α(1,3)-fucose (anti-Fuc) epitopes. Nevertheless, Phaeodactylum tricornutum proteins exhibit high-mannose sequences as revealed by Con A binding, a lectin specific for high-mannose sequences. The presence of high-mannose sequences in Phaeodactylum tricornutum proteins was also confirmed by deglycosylation assays using peptide N-glycosidase F (PNGase F) and Endoglycosidase H (Endo H) (data not shown).

In order to determine the specific glycosylation pattern of Phaeodactylum tricornutum proteins, said proteins were digested prior to mass spectrometry analysis.

Total proteins were digested by successive treatments with pepsin and PNGase A as previously described in FITCHETTE et al. (above mentioned, 2006). 4 mg of proteins were digested with 6 mg of pepsin in 2 mL of 10 mM HCl, pH 2.2, at 37° C. for 48 h. After neutralization with 1 M ammonium hydroxide, the solution was heated for 5 min at 100° C. and lyophilized. Glycopeptides were then deglycosylated overnight at 37° C. with PNGase A (10 mU, BOEHRINGER MANNHEIM) in a 100 mM sodium acetate buffer, pH 5.0. N-Glycans were purified by successive elution through an AG 50W-X2 column (BIO-RAD) and a C18 cartridge (VARIAN) according to FITCHETTE et al. (above mentioned, 2006). The purified N-glycans were then labelled by 2-aminobenzamide (2-AB) using the optimized protocol described in BIGGE et al. (Anal Biochem, vol. 230, p: 229-238, 1995). Then, labelled N-glycans were detected with an UV light and eluted using water. The eluted labelled N-glycans were finally lyophilised prior to exoglycosidase digestion and MALDI-TOF mass spectrometry analysis. For exoglycosidase digestion, 200 milliunits of Jack bean α-mannosidase (SIGMA-ALDRICH) were desalted by ultrafiltration using a Centricon and incubated overnight at 37° C. with approximately 50 pmoles of 2-AB labelled N-glycan mixture. Then, the 2-AB labelled N-glycans was directly analysed by matrix assisted laser desorption ionisation-time of flight (MALDI-TOF) mass spectrometry on a Voyager DE-Pro MALDI-TOF instrument (APPLIED BIOSYSTEMS) equipped with a 337 nm nitrogen laser. Mass spectra were performed in the reflector delayed extraction mode using 2,5-dihydroxybenzoic acid (SIGMA-ALDRICH) as matrix. The matrix, freshly dissolved at 5 mg/mL in a 70:30 acetonitrile/0.1% TFA, was mixed with the water solubilized oligosaccharides in a ratio 1:1 (v/v). These spectra were recorded in a positive mode, using an acceleration voltage of 20,000 V with a delay time of 100 ns. They were smoothed once and externally calibrated using commercially available mixtures of peptides and proteins (APPLIED BIOSYSTEMS). In this study, the spectra have been externally calibrated using des-Arg$^1$-bradykinin (904.4681 Da), angiotensin I (1296.6853), Glu$^1$-fibrinopeptide B (1570.6774 Da), ACTH$_{18-39}$ (2465.1989 Da) and bovine insulin (5730.6087 Da). 1000 Laser shots were accumulated for each spectrum and several spectra were accumulated (between 5 to 10 spectra) in order to obtain a good signal to noise ratio.

The results in FIG. 13 have shown that the major ions (95-97%) for the resulting pool of labeled N-glycans correspond to (M+Na)$^+$ ions of 2-AB derivatives of Hexose$_{5-9}$GlcNAc$_2$. Nevertheless, no derivatives GlcNAc-Hexose$_5$GlcNAc$_2$ was detected.

Consequently, we show that P. tricornutum does not exhibit a significant GnT I activity.

Example 2

A Putative GnT I Detected in P. Tricornutum GnT I Complement CHO$^{\Delta GnT-I}$ Cells Even if no detectable GnT I activity was identify in Phaeodactylum tricornutum, we try to express the nucleic acid sequence corresponding to the P. tricornutum putative GnT I full-length sequence (Pt54844) (SEQ ID No2) in CHO Lec1 mutant, which is mutated on its endogenous GnT I. Said P. tricornutum sequence was expressed in the CHO mutant in fusion with a V5 epitope to monitor the expression of the fusion protein in transformants.

On the basis of the detection of this epitope with anti-V5 antibodies, we show that most of the CHO transformants were found to express the V5 fusion protein (data not shown). Two cell lines expressing the V5 fusion protein were selected for N-linked glycan analysis.

Proteins from these lines as well as from wild-type and Lec1 CHO cells were isolated and their N-linked glycans were released by treatment with PNGase F followed by MALDI-TOF mass spectrometry analysis.

The results shown that the CHO Lec1 mutant accumulates high-mannose-type N-glycans, in contrast to wild-type CHO cells which exhibited both high-mannose-type and complex-type N-glycans. Surprisingly, the proteins from the CHO Lec1 mutant expressing V5 fusion protein carry both high-mannose-type and a complete set of complex N-glycans identical to the one observed in wild-type CHO cells (FIG. 14).

Finally, these results show that even if no GnT I activity was significantly detectable in P. tricornutum, the expression of the Pt54844 gene was able to restore the biosynthesis of complex N-glycans in mammalian cells.

In conclusion, Pt54844 gene encodes for a functional transferase designed as Pt GnT I.

Example 3

Expression of GnT I in *Phaeodactylum tricornutum* and Validation by RT-PCR

The Pt54844 gene disclosed previously (SEQ ID No2) was cloned under of an enhanced promoter of Cauliflower Mosaic Virus in a pPha-T1 based vector called BSJ-25 vector. As a control, vectors comprising GnT I from *Arabidopsis thaliana* (AtGnT I, At4g38240) and GnT I from human cell (hGnT I, MGAT1) were also constructed. BSJ-25 (SEQ ID No79) was derived from pPha-T1 (Zaslayskaia and Lippmeier, 2000, J. Phycol. vol. 36(2), p: 379-386.) vector by replacing the FcpA promoter of the expression cassette by the double enhanced Cauliflower Mosaic Virus (CaMV35S) (SEQ ID No80) fused to the plant signal peptide. For this, pPha-T1 containing bleomycin-resistance cassette driven by FcpB promoter was digested with Nde1 and EcoR1 to remove the FcpA promoter. This construct was designated as "pPha-T1-PfcpA deleted". The double enhanced Cauliflower Mosaic Virus 35S promoter of the expression cassette was amplified by PCR with forward primer, CaMV35Sfwd (5'-GAACATATGGTGGATTGAT-GTGATCTACTCC-3') (SEQ ID No61) and reverse primer, CaMV35Srev (5'-AATTCTCGAGGAATTCGGCCGAGG-3') (SEQ ID No62) on the PS1 construct (Kotzer et al., 2004, J Cell Sci, vol. 117(Pt 26), p: 6377-89). PS1 construct contains a double Cauliflower Mosaic Virus 35S promoter (SEQ ID No80), a tobacco Mosaic Virus—Ω sequence as translation enhancer fused to the tobacco chitinase signal peptide of SEQ ID No81 (Haseloff et al., 1997, Proc Natl Acad Sci USA, vol. 94(6), p: 2122-7.; Batoko et al., 2000, Plant Cell, vol. 12(11), p: 2201-18). The PCR product was digested by Nde1 and EcoR1 and then was cloned into "pPha-T1-PfcpA deleted" to generate BSJ-25 vector.

To resume, the expression cassette of BSJ-25 vector contain a double CaMV promoter, a translational enhancer, a signal peptide, a multi-cloning site and the FcpA terminator (FIG. 3). The GnT I gene from various origin has been introduced in this vector using enzymatic digestion from the multi-cloning site and the inserts had been cloned between the signal peptide and the terminator sequence.

Specific vectors expressing the abovementioned genes in fusion to Green Fluorescent Protein (GFP) were also constructed to investigate the cellular localisation in the Golgi apparatus of the corresponding fusion proteins.

The constructs can be seen in FIG. 12.

Said vectors were used to transform *Phaeodactylum tricornutum*.

Transformation of *Phaeodactylum tricornutum* was carried out as described by Zaslayskaia et al. (2000, J. Phycol. Vol. 36(2), p: 379-386). *P. tricornutum* 1.8.6 are cultivated (flask or agar plate 10%) in sterile sea water (0.22 μm filtered) enriched with 0.1% (v/v) of the nutritive medium (Conway) and 0.1% (v/v) of a silica solution (0.4 g/ml). All the cultures are maintained at 20° C. under continuous lighting in sterile conditions. For genetic transformation, cultures of microalgae in exponential phase of growth are counted and concentrated by centrifugation, diluted in sterile sea water and approximately $10^8$ cells were inoculated as a plaque of 2.5 cm of diameter on the surface of the medium agar plate. Five hundred micrograms or gold microcarrier (0.6 μm of particle size) was coated with 1 μg of vector DNA in the presence of 1.25M of $CaCl_2$ and 20 μM of spermidin.

The transformation was carried out with the BIORAD PDS-1000/He biolistic particle delivery system for particles bombardment. Experiments are performed under a hood. The bombardment was performed at 900 and 1100 psi under a negative pressure of 27 Hg with different target distance (6-8 cm). After bombardment, cells transformed were suspended in 600 μL of nutritive sea water and were cultivated 1 day under illumination at 20° C. Transformed cells were spread on agar plate medium containing 100 μg·$mL^{-1}$ of Zeocin and incubated to grown 3 or 4 weeks under continuous light.

The presence of transcripts for the recombinant GnT I was then monitored by reverse transcription PCR(RT-PCR). Microalgae pellet were resuspended in 1.2 mL of Trizol (INVITROGEN) and homogenized in 2 mL Lysing Matrix E by 10 Fastprep-24 run (6.5 m/s, 60 sec, MP BIOMEDICALS). 300 μL of chloroform were added to the supernatant, vigorously homogenized and incubated 3 min at room temperature. After a 15 min centrifugation at 4° C., the aqueous was mixed with 1 volume of absolute ethanol and the RNA were purified by RNEASY MINI kit (QIAGEN). The purified RNA were eluted in 50 μL of RNase-free water, dosed with NanoDrop (THERMO SCIENTIFIC) and were digested by RQ1 DNase (PROMEGA). After second purification by RNEASY MINI kit and Nanodrop quantification, RNA were conserved at −80° C.

Reverse Transcription (RT) was performed on 1 μg of purified RNA. The first cDNA strand was synthesised by 200 units of M-MLV RT RNase H minus (PROMEGA) with oligodT primers. Two μL of cDNA were used for PCR with GoTaq polymerase (PROMEGA) in 50 μL. The annealing was performed with specific primers of GnT I and actin sequence.

The results confirmed the expression of transcripts for the recombinant GnT in the selected recombinants (data not shown).

The glycosylation pattern of proteins expressed in said transformants is then performed as disclosed previously. Simultaneously, the cellular localisation of the fusion proteins is investigated by observing the GFP fluorescence of GnT I-GFP fusion proteins by confocal microscopy.

Another set of tests were run in order to demonstrate the expression and localization of endogenous GnT I in transformed *Phaeodactylum tricornutum*.

Example 4

Expression of Endogenous GnT I and Validation by RT-PCR and Q-PCR

1) Constructions Comprising the Sequence of GnT I

Different constructs comprising the sequence coding for the endogenous GnT I from *Phaeodactylum tricornutum* were realised with the cloning vector pPHA-T1 built by Zavlaskaïa et al. (2000) for the genetic transformation of *Phaeodactylum tricornutum*, said vector including sequences of *P. tricornutum* promoters fcpA and fcpB (fucoxanthin-chlorophyll a/c-binding proteins A and B) and the terminator of fcpA. It contains a selection cassette with the gene she ble and a MCS flanking the fcpA promoter.

Said constructs are schematised in FIG. 4.

The first cassette comprised the sequence coding for the endogenous GnT I placed under the control of endogenous regulatory sequences. In the second construction, the GnT I was fused to the Green Fluorescent Protein (GFP).

The endogenous GnT I sequence of *Phaeodactylum tricornutum* was cloned in an expression vector with regulatory sequences from said microalgae. The GnT I was cloned alone or fused to the Green Fluorescent Protein (eGFP). The expression of said fusion protein enabled to visualise the expression and localization of the GnT I in the microalgae.

The vectors used for the transformation of *Phaeodactylum tricornutum* also comprised a selection cassette comprising a zeocin resistance gene. They enabled the genetic transformation of the Pt186 *Phaeodactylum tricornutum* strain.

The obtained clones were isolated and cultured in order to be analysed.

The transformation of *Phaeodactylum tricornutum* was realized as described previously.

2) Screening of Transformed Microalgae

The clones obtained after the transformation of the Pt186 *Phaeodactylum tricornutum* strain were isolated on fresh culture medium. The insertion of the construction comprising a gene coding for GnT I in the genome of the microalga was verified by PCR amplification with a set of specific primers for the transgene (SEQ ID No69 for the vector and SEQ ID No70 for the GnT I).

The PCR reaction was carried out in a final volume of 50 µl consisting of 1× PCR buffer, 0.2 mM of each dNTP, 5 µM of each primer, 20 ng of template DNA and 1.25 U of Taq DNA polymerase (Taq DNA polymerase, ROCHE). Thirty cycles were performed for the amplification of template DNA. Initial denaturation was performed at 94° C. for 3 min. Each subsequent cycle consisted of a 94° C. (1 min) melting step, a 55° C. (1 min) annealing step, and a 72° C. (1 min) extension step. Samples obtained after the PCR reaction were run on agarose gel (1%) stained with ethidium bromide.

The results are shown on FIG. 5 and present the screening obtained for 5 different lineages of potentially transformed *Phaeodactylum tricornutum*. The amplification of a specific sequence of 120 bp from the transgene obtained for the positive control (plasmidic DNA) was also found in the 5 analysed clones. The clones of the microalga therefore did integrate the genetic construction comprising the gene coding for the endogenous GnT I.

3) Screening of Microalgae Expressing the GnT I a) Analysis of the Expression of GnT I by RT-PCR A transcriptomic analysis was realised on transformed clones with the sequence coding for the *P. tricornutum* GnT I. The total RNAs from the different clones were purified. The corresponding cDNA were synthesized then analysed by Reverse Transcription PCR amplification according to the instructions as disclosed in Example 3 with specific primers for the transgene (SEQ ID No71 and SEQ ID No72) and with the H4 housekeeping gene (SEQ ID No73 and SEQ ID No74).

The results of the amplifications realised with specific primers from the H4 housekeeping gene are presented in FIG. 6. The absence of amplification for the RT-samples enables to validate that the samples did not contain genomic DNA.

The amplifications realised on the RT+ samples enabled to obtain amplicons at 150 bp which were homogenous between all the Pt-GnT I clones. This study therefore enabled to validate the experimental conditions.

The Pt-GnT I clones were then analysed with primers enabling the highlight of the expression of GnT I (see FIG. 7).

The FIG. 7 represents the RT-PCR results obtained for the expression of GnT I in the *P. tricornutum* transformed clones. The absence of amplification in the RT-samples validates the quality of the samples. Furthermore, the amplification fragment of 212 bp with a higher intensity than the one of the wild type strain is obtained for the clones 1 and 3. This difference of signal corresponds to a surexpression of GnT I. Therefore, the inventors were able to identify microalgae clones which surexpressed the GnT I. A thinner analysis of the expression of GnT I was proceeded by quantitative PCR (Q-PCR).

b) Analysis of the Expression of GnT I by Q-PCR

A lineage from transformed *P. tricornutum* with a construction comprising the GnT I gene was selected by RT-PCR. The expression of GnT I was then analysed by Q-PCR as disclosed in Siaut et al., 2007, Molecular toolbox for studying diatom biology in *Phaeodactylum tricornutum*, Gene 406 (1-2): 23-35, by using primers directed to the transgene (SEQ ID No75 and SEQ ID No76) and the H4 housekeeping gene (SEQ ID No 77 and SEQ ID No78).

Figure 8A:
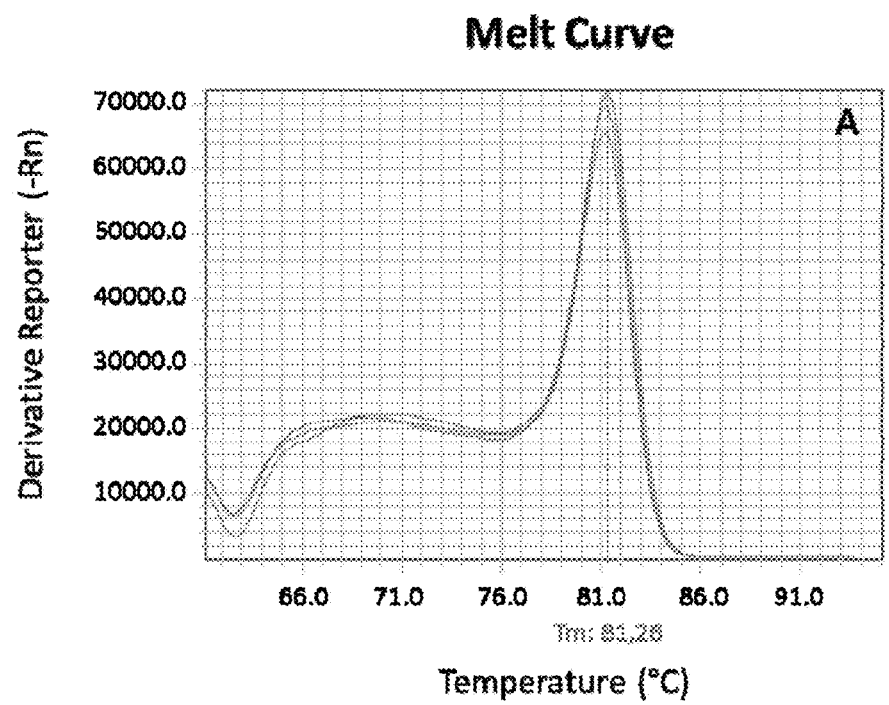

The FIG. 8A corresponds to a fusion curve. It enables to verify that only one PCR product has been amplified. The presence of one peak shows that only one amplification fragment was obtained. The dissociation temperature of 81.2° C. shows a strong specificity of the amplicon-primers association.

Figure 8B:
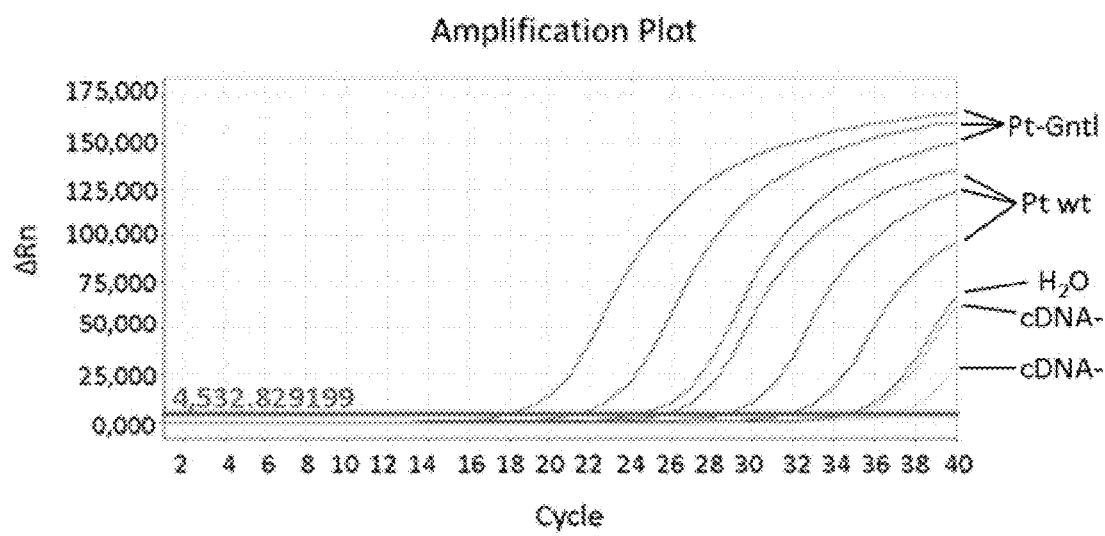

The FIG. 8B presents the detection profile of GnT I in the transformed cells (Pt-GnT I) and the wild-type cells (Pt-wt). For each strain, 3 dilutions of cDNA were analysed. The results were expressed in number of cycles compared to the relative values of detection of the GnT I amplicon.

The 3 sigmoids corresponding to negative controls (cDNA- and water) show a late detection, which is indicative of a non-significative amplification of GnT I.

The analysis of the transformed lineage with GnT I showed a detection which was significantively earlier than the wild-type cells. The data obtained were normalized with a housekeeping gene H4. The normalisation compared to the housekeeping gene by using the comparative Ct method also called as $2^{-[delta][delta]Ct}$ ($\Delta\Delta$CT method) revealed a clear difference of expression profile between the strain expressing the GnT I transgene and the wild-type cells ($\Delta\Delta$CT=7).

Example 5

Display of the Expression and Localisation of the GnT I-eGFP Protein

1) By Confocal Microscopy

The clones of the *P. tricornutum* microalgae which were transformed with a sequence coding for a GnT I-eGFP fusion protein were analyzed by confocal microscopy with standard parameters. The FIG. 9 presents the results of said analysis.

The observations realized clearly show a difference of fluorescence localization between the microalgae expressing a cytosolic eGFP and the GnT I-eGFP fusion protein. In that case, the fluorescence is much more localised and is presented under the form of a bowl or a bean. This marking is typical of the Golgi apparatus in *P. tricornutum* microalgae.

The inventors therefore demonstrated that the endogenous GnT I was expressed and localized in the suitable cell compartment.

2) By Analysis after Treatment of the Culture with Brefeldin A and Epifluorescence Microscopy In order to validate those results, the inventors analyzed the clones expressing a GnT I-eGFP fusion protein after a treatment of the culture of the transformed microalgae with brefeldin A compared to microalgal strain of *P. tricornutum* expressing eGFP in the chloroplast, in the endoplasmic reticulum or in the Golgi apparatus after a culture with brefeldin A (FIG. 10).

The brefeldin A is a molecule presenting a particularity of dismantling the structure of the Golgi apparatus in the cells. Therefore, it is possible to confirm the localization of the fusion protein which is produced in *P. tricornutum* microalgae. The cells were incubated with 50 µM of brefeldin A and the observations were conducted with an epifluorescence microscopy on a period of 48 hours.

The FIG. 10 presents the results which were obtained. No fluorescence variation was observed in the *P. tricornutum* microalgae expressing eGFP in the chloroplast or in the Endoplasmic Reticulum after a culture with brefeldin A. In the microalgae expressing the GnT I-eGFP fusion protein, small fluorescent vesicles rapidly appeared (after 5 hours on the picture), which is indicative of the effect of brefeldin A on the Golgi apparatus. Said effect became more and more visible after 24 and 48 hours of culture with a marking spreading to the whole cell. The Golgi marking which was very targeted almost disappeared.

This analysis enabled to validate that the GnT I-eGFP fusion protein is expressed and localized in the Golgi apparatus of transformed *P. tricornutum* microalgae.

3) Immunoblotting Analysis by Western Blot

Aliquotes of wild-type and transformed cells of *P. tricornutum* culture at exponential phase of growth are collected and cells are separated from the culture medium by centrifugation (10 minutes, 2150 g, 20° C.). Cell pellets are resuspended in Tris-HCl 0.15 M pH 8, saccharose 15%, SDS 0.5%, PMSF 1 mM, protease inhibitor cocktail 1% (SIGMA) and sonicated for 30 min. Cell suspensions obtained are centrifuged (60 minutes, 15000 g, 4° C.) to remove cell debris and supernatants correspond to the intracellular fraction.

Ten µL of intracellular fractions from Pt-eGFP, Pt-GntI-eGFP transformed and wild-type cells are separated by SDS-PAGE using a 12% polyacrylamide gel. The separated proteins are transferred onto nitrocellulose membrane and stained with Ponceau Red in order to control transfer efficiency. The nitrocellulose membrane is blocked overnight in milk 5% dissolved in TBS for immunodetection. Immunodetection is then performed using horseradish peroxidase-conjugated anti-GFP (Santa Cruz, sc-9996-HRP) (1:2000 in TBS-T containing milk 1% for 2 h at room temperature). Membranes are then washed with TBS-T (6 times, 5 minutes, room temperature) followed by a final wash with TBS (5 minutes, room temperature). Final development of the blots is performed by chemiluminescence method.

The total protein extracts from wild-type *P. tricornutum* microalgae, from *P. tricornutum* microalgae expressing the eGFP protein (Pt-eGFP) and from *P. tricornutum* microalgae expressing the GnT I-eGFP fusion protein (Pt-GnT I-eGFP) were analyzed by Western Blot with anti-GFP antibodies which were coupled to peroxidase.

The FIG. 11 presents the results obtained for the detection of the GnT I-eGFP fusion protein by Western Blot. The figure shows a detection at around 28 kDa for the cytosolic eGFP and around 75 kDa for the clones which were transformed with a sequence coding for the GnT I-eGFP fusion protein, which theoretical size corresponds to 77 kDa.

The presence of the fusion protein in the protein samples from transformed microalgae is therefore demonstrated. The absence of degradation is a proof that the fusion protein is stable.

This analysis therefore demonstrates that it is possible to express the *P. tricornutum* endogenous GnT I sequence and that said protein is addressed to the suitable cell compartment, i.e. the Golgi apparatus.

Example 6

Glycosylation Pattern of Proteins Expressed in Transformed *P. Tricornutum* with Endogenous GnT I In order to investigate the presence in *P. tricornutum* proteins of complex-type N-glycans carrying terminal GlcNAc, we treat the protein extract with a β1,4-galactosyltransferase, an enzyme able to transfer a galactose residue onto terminal GlcNAc residues, and then we analyze by affinoblotting the resulting protein preparation either with RCA 120 or ECA, which are lectins that bind specifically to Galβ1-4GlcNAc sequences according to a strategy previously reported (Bardor et al., 2003, *Plant Biotech J*, vol. 1, 451-462). Alternatively, the glycosylation pattern of proteins expressed in transformed *P. tricornutum* with endogenous GnT I is study by approaches which has been mentioned above.

Example 7

Expression of α-Man II in *Phaeodactylum tricornutum*

A gene encoding a putative α-Man II was predicted in the *P. tricornutum* genome (Pt52108).

The Pt52108 gene (SEQ ID No6) is cloned under of an enhanced promoter of Cauliflower Mosaic Virus in a pPha-T1 based vector called BSJ-25 vector. As a control, vectors comprising α-Man II from *Arabidopsis thaliana* (NP_196999) and from human cell (Q16706 or AAC50302) are also constructed. BSJ-25 is derived from pPha-T1 vector (Zaslayskaia and Lippmeier, 2000, J. Phycol. vol. 36(2), p: 379-386) by replacing the FcpA promoter of the expression cassette by the double enhanced Cauliflower Mosaic Virus (CaMV35S) fused to the plant signal peptide. For this, pPha-T1 containing bleomycin-resistance cassette driven by FcpB promoter is digested with Nde1 and EcoR1 to remove the FcpA promoter. This construct was designated as "pPha-T1-PfcpA deleted". The double enhanced Cauliflower Mosaic Virus 35S promoter of the expression cassette is amplified by PCR with forward primer, CaMV35Sfwd (5'-GAACATATGGTGGATTGATGTGATCTACTCC-3') (SEQ ID No61) and reverse primer, CaMV35Srev (5'-AATTCTCGAGGAATTCGGCCGAGG-3') (SEQ ID No62) on the PS1 construct (Kotzer et al., 2004, J Cell Sci, vol. 117(Pt 26), p: 6377-89). PS1 construct contains a double Cauliflower Mosaic Virus 35S promoter, a tobacco Mosaic Virus—Ω sequence as translation enhancer fused to the tobacco chitinase signal peptide (Haseloff et al., 1997, Proc Natl Acad Sci USA, vol. 94(6), p: 2122-7.; Batoko et al., 2000, Plant Cell, vol. 12(11), p: 2201-18). The PCR product is digested by Nde1 and EcoR1 and then is cloned into "pPha-T1-PfcpA deleted" to generate BSJ-25 vector.

To resume, the expression cassette of BSJ-25 vector contain a double CaMV promoter, a translational enhance, a signal peptide, a multi-cloning site and the FcpA terminator (FIG. 3).

Specific vectors expressing the abovementioned genes in fusion to Green Fluorescent Protein (GFP) are also constructed to investigate the cellular localisation in the Golgi apparatus of the corresponding fusion proteins.

Said vectors are used to transform *Phaeodactylum tricornutum*.

Transformation of *Phaeodactylum tricornutum* is carried out as disclosed previously in the example of expression of GnT I in *Phaeodactylum tricornutum*.

The presence of transcripts for the recombinant α-Man II is then monitored by reverse transcription PCR(RT-PCR). Microalgae pellet are resuspended in 1.2 mL of Trizol (INVITROGEN) and homogenized in 2 mL Lysing Matrix E by 10 Fastprep-24 run (6.5 m/s, 60 sec, MP BIOMEDICALS). 300 µL of chloroform are added to the supernatant, vigorously homogenized and incubated 3 min at room temperature. After a 15 min centrifugation at 4° C., the aqueous is mixed with 1 volume of absolute ethanol and the RNAs were purified by RNEASY MINI kit (QIAGEN). The purified RNAs are eluted in 50 µL of RNase-free water, dosed with NanoDrop (Thermo SCIENTIFIC) and are digested by RQ1 DNase (PROMEGA). After second purification by RNEASY MINI kit and Nanodrop quantification, RNAs are conserved at −80° C.

Reverse Transcription (RT) is performed on 1 µg of purified RNA. The first cDNA strand is synthesised by 200 units of M-MLV RT RNase H minus (PROMEGA) with oligodT primers. Two µL of cDNA are used for PCR with GoTaq polymerase (PROMEGA) in 50 µL. The annealing is performed with specific primers of GnT I and actin sequence.

The results confirm the expression of transcripts for the recombinant α-Man II in the selected recombinants (data not shown).

The glycosylation pattern of proteins expressed in said transformants is then performed as disclosed previously. Simultaneously, the cellular localisation of the fusion proteins is investigated by observing the GFP fluorescence of GnT I-GFP fusion proteins by confocal microscopy.

Example 8

Glycosylation Pattern of Proteins Expressed in Transformed *P. Tricornutum* with Endogenous Alpha Man II The glycosylation pattern of proteins expressed in transformed *P. tricornutum* with endogenous alpha Man II is studying by HPLC and Mass spectrometry approaches as mentioned above.

Example 9

Inactivation of N-acetylglucosaminidases in *Phaeodactylum tricornutum* with RNA Interference a) By the Use of Vectors This example is based on the use of constructs containing antisense RNA or inverted-repeat RNA for the inactivation of β-N-acetylglucosaminidase expression as described in De Riso V. et al., 2009, Nucleic Acids Research, p: 1-12.

For the generation of a β-N-acetylglucosaminidase vector, two fragments from the β-N-acetylglucosaminidase cDNA are amplified with specific primers, wherein one of the fragments is longer than the other fragment and also contains the total sequence of the shorter fragment. The two obtained fragments are then digested with restriction enzymes which can also be used for the linearization of the vector.

For the antisense construct, one of the two fragments obtained is inserted into the vector in the antisense orientation.

For the inverted-repeat construct, fragments are ligated in sense and antisense orientations in the integration site of the vector.

Said vectors are then used together or separately by choosing one vector to transform *Phaeodactylum tricornutum*. Transformation of *Phaeodactylum tricornutum* is carried out as described in example 3.

b) By the Use of siRNAs

The gene silencing of β-N-acetylglucosaminidases can also be obtained with the transformation of *Phaeodactylum tricornutum* with the use of siRNAs specific of at least one gene encoding a β-N-acetylglucosaminidase in said microalga (1 µg for each siRNA). Transformation of *Phaeodactylum tricornutum* is carried out as described in example 3.

siRNAs used for the transformation of *Phaeodactylum tricornutum* have the following sequences:

siRNAs specific of a first β-N-acetylglucosaminidase of amino acid sequence SEQ ID No9 which is encoded by the nucleic acid sequence SEQ ID No10

```
siRNA1(β-N-acetylglucosaminidase SEQ ID No 10)
                                    SEQ ID No 63
GGCCAUUCGUUACUAGCAA siRNA2(β-N-acetylglucosaminidase SEQ ID No 10)
                                    SEQ ID No 64
GUGGUUCGUUGGGAAAUGA siRNA3(β-N-acetylglucosaminidase SEQ ID No 10)
                                    SEQ ID No 65
CCGUCUGUGUGAAAUUGGU
``` siRNAs specific of a second β-N-acetylglucosaminidase of amino acid sequence SEQ ID No11 which is encoded by the nucleic acid sequence SEQ ID No12

```
siRNA1(β-N-acetylglucosaminidase SEQ ID No 12)
                                    SEQ ID No 66
CGGUAGUAGUGCUUGUUGU siRNA2(β-N-acetylglucosaminidase SEQ ID No 12)
                                    SEQ ID No 67
CUGCCAUGGAUAUUGUCAA siRNA3(β-N-acetylglucosaminidase SEQ ID No 12)
                                    SEQ ID No 68
GCCUUUGGUCCUGAAGAAA
```

Example 10

Expression and Glycosylation of a Polypeptide in Transformed *P. tricornutum*

As explained previously, polypeptides of interest to be expressed and glycosylated in transformed *P. tricornutum* according to the invention are proteins of therapeutic interest. We choose the erythropoietin to exemplify the expression and glycosylation of such proteins in transformed *P. tricornutum* according to the invention. However, the invention is not limited to said erythropoietin and could be applied to any protein of therapeutic interest which needs to be glycosylated to present the adequate glycosylation pattern.

a) Expression Construct for Erythropoietin

The vector used for the expression of Erythropoietin comprises a nucleic acid sequence operably linked to a promoter, said nucleic acid sequence encoding Erythropoietin. Said vector preferably contains a selectable marker distinct from the selectable markers present on the BSJ-25 vector according to the example 3.

b) Transformation of *P. tricornutum*

Transformed *P. tricornutum* of example 3 are also transformed with a vector according to step a).

c) Glycosylation Pattern Analysis of Expressed and Glycosylated Erythropoietin

The glycosylation pattern of Erythropoietin that is expressed and glycosylated in the transformed *P. tricornutum* according to the invention is described in the example 1.

---

The invention claimed is:

1. A transformed *Phaeodactylum tricornutum*, whose N-glycosylation pathway has been modified by inactivation of terminal N-acetylglucosamine residue removal activity of at least one β-N-acetylglucosaminidase.

2. The transformed *P. tricornutum* of claim 1, further comprising a nucleic acid sequence operatively linked to a promoter, wherein said nucleic acid sequence encodes an N-acetylglucosaminyltransferase II corresponding to an amino acid sequence capable of adding an N-acetylglucosamine residue to GlcNAcMan$_3$GlcNAc$_2$ to produce GlcNAcMan$_3$GlcNAc$_2$, and having more than 85% of identity with the amino acid sequence SEQ ID NO: 5.

3. The transformed *P. tricornutum* of claim 2, wherein
   (i) said N-acetylglucosaminyltransferase II comprises the amino acid sequence SEQ ID NO: 15, and
   (ii) said operatively linked promoter has a sequence identity of less 50% with SEQ ID NO: 7 or a fragment thereof.

4. The transformed *P. tricornutum* of claim 1, wherein said *P. Tricornutum* further comprises another nucleic acid sequence operatively linked to a promoter, said another nucleic acid sequence encoding a polypeptide that is expressed and glycosylated in the transformed *P. tricornutum*.

5. The transformed *P. tricornutum* of claim 4, wherein said glycosylated polypeptide has at least one GlcNAcMan$_5$GlcNAc$_2$ structure.

6. The transformed *P. tricornutum* of claim 4, wherein said polypeptide is selected from the group consisting of erythropoietin, cytokines, antibodies and their fragments, coagulation factors, hormones, beta-glucocerebrosidase, pentraxin-3, anti-TNFs, acid α-glucosidase, α-L-iduronidase and derivatives thereof.

7. The transformed *P. tricornutum* of claim 1, wherein said *P. tricornutum* further comprises another nucleic acid sequence operatively linked to a promoter, said another nucleic acid sequence encoding at least one enzyme selected among N-acetylglucosaminyltransferase III, IV, V and VI.

8. The transformed *P. tricornutum* of claim 7, wherein said *P. tricornutum* further comprises another nucleic acid sequence operatively linked to a promoter, said nucleic acid sequence encoding at least one glycosyltransferase enzyme selected from the group consisting of galactosyltransferases, fucosyltransferases and sialyltransferases.

* * * * *